US005721354A

United States Patent [19]

Spaete et al.

[11] Patent Number: 5,721,354

[45] Date of Patent: Feb. 24, 1998

[54] HUMAN CYTOMEGALOVIRUS DNA SEQUENCES

[75] Inventors: Richard Spaete, Belmont; Tai-An Cha, San Ramon, both of Calif.

[73] Assignee: Aviron, Mountain View, Calif.

[21] Appl. No.: 414,926

[22] Filed: Mar. 31, 1995

[51] Int. Cl.[6] .................................................. C07H 21/04

[52] U.S. Cl. .................................. 536/23.72; 424/230.1; 435/5; 435/172.3; 435/252.3; 435/320.1; 435/69.3

[58] Field of Search ............................ 424/230.1; 435/5, 435/69.3, 172.3, 252.3, 320.1; 536/23.1

[56] References Cited

U.S. PATENT DOCUMENTS 5,075,213 12/1991 Pande et al. ................................ 435/5

OTHER PUBLICATIONS

Robson et al, Primate Cytomegalovirus Assembly Protein: Genome Location and Nucleotide Sequence, J. Virology 63(2). 1989. 669–676, see Abstract.

Pande et al., Human Cytomegalovirus strain Towne pp. 65 gene nucleotide sequence, Virology 182(1). 1991. 220–228. see Abstract.

Pande et al., Human Cytomegalovirus strain Towne pp. 28 gene sequence comparison to pp. 28 of HCMV AD169, Virology 184(2). 1991. 762–767. see Abstract and Fig. 3.

Chou, *J. Infect. Dis.* 162:738–42 (1990).

Pritchett, *J. Virol* 36:152–61 (1980).

Lehner, *J Clin Microbiol* 29:2494–2502 (1991).

Fries, *J. Infect Dis* 169:769–74 (1994).

Quinnan, *Annals of Int Med* 101:478–83 (1984).

Plotkin, *Lancet* 1:528–30 (1984).

Plotkin, *J Infect Dis* 159:860–65.

Huang, *Yale J Biol and Med* 49:29–43 (1976).

Kilpatrick, *J Virol* 18:1095–1105 (1976).

LaFemina, "Structural Organization of the DNA Molecules from Human Cytomegalovirus Animal Virus Genetics", Field, B.N. and R. Joenish, eds., Academic Press, NY 1980, pp. 52–53.

Chandler,*J Gen Virol* 67:2179–92 (1986).

Zaia, *J Clin Microbiol* 28:2602–07 (1990).

Spaete, *Virology* 167:207–25 (1988).

Chou, *J Infect Dis* 163:1229–34 (1991).

Marshall & Plotkin, Cytomegalovirus Vaccines, The Human Herpesviruses, Roizman, B., R.J. Whitley, and C. Lopez, eds., Raven Press, NY (1993) pp. 381–95.

Alford & Britt, Cytomegalovirus Vaccines, The Human Herpesviruses, Roizman, B., R.J. Whitley, and C. Lopez, eds., Raven Press, NY (1993) pp. 227–55.

*Primary Examiner*—Donald E. Adams
*Assistant Examiner*—Hankyel T. Park
*Attorney, Agent, or Firm*—Luann Cserr; Tracy Dunn

[57] ABSTRACT

Provided are novel Toledo and Towne human cytomegalovirus DNA sequences (HCMV) and proteins encoded thereby. The sequences are useful in methods and compositions for detecting HCMV infections and in immunogenic compositions for preventing HCMV infections.

5 Claims, 53 Drawing Sheets

UL133 →

```
        10         20         30         40         50         60
CGCTGTAGGG ATAAATAGTG CGATGGCGTT TGTGGGAGAA CGCAGTAGCG ATGGGTTGCG
GCGACATCCC TATTTATCAC GCTACCGCAA ACACCCTCTT GCGTCATCGC TACCCAACGC

        70         80         90        100        110        120
ACGTGCACGA TCCTTCGTGG CAATGCCAAT GGGGCGTTCC CACGATTATC GTGGCCTGGA
TGCACGTGCT AGGAAGCACC GTTACGGTTA CCCCGCAAGG GTGCTAATAG CACCGGACCT

       130        140        150        160        170        180
TAACATGCGC GGCTTTAGGA ATTTGGTGTT TGGCGGGATC GTCGGCGGAT GTCTCTTCGG
ATTGTACGCG CCGAAATCCT TAAACCACAA ACCGCCCTAG CAGCCGCCTA CAGAGAAGCC

       190        200        210        220        230        240
GACCCGGCAT CGCAGCCGTA GTCGGCTGTT CTGTTTTCAT GATTTTCCTC TGCGCGTATC
CTGGGCCGTA GCGTCGGCAT CAGCCGACAA GACAAAAGTA CTAAAAGGAG ACGCGCATAG

       250        260        270        280        290        300
TCATCCGTTA CCGGGAATTC TTCAAAGACT CCGTAATCGA CCTCCTTACC TGCCGATGGG
AGTAGGCAAT GGCCCTTAAG AAGTTTCTGA GGCATTAGCT GGAGGAATGG ACGGCTACCC

       310        320        330        340        350        360
TTCGCTACTG CAGCTGCAGC TGTAAGTGCA GCTGCAAATG CATCTCGGGC CCCTGTAGCC
AAGCGATGAC GTCGACGTCG ACATTCACGT CGACGTTTAC GTAGAGCCCG GGGACATCGG

       370        380        390        400        410        420
GCTGCTGTTC AGCGTGTTAC AAGGAGACGA TGATTTACGA CATGGTCCAA TACGGTCATC
CGACGACAAG TCGCACAATG TTCCTCTGCT ACTAAATGCT GTACCAGGTT ATGCCAGTAG

       430        440        450        460        470        480
GACGGCGTCC CGGACACGGC GACGATCCCG ACAGGGTGAT CTGCGAGATA GTCGAGAGTC
CTGCCGCAGG GCCTGTGCCG CTGCTAGGGC TGTCCCACTA GACGCTCTAT CAGCTCTCAG
```

FIG._1A-1

```
      490        500        510        520        530        540
CCCCGGTTTC GGCGCCGACG GTGTCCGTCC CCCCGCCGTC GGAGGAGTCC CACCAGCCCG
GGGGCCAAAG CCGCGGCTGC CACAGGCAGG GGGGCGGCAG CCTCCTCAGG GTGGTCGGGC

UL134
      550        560        570        580        590        600
TCATCCCACC GCAGCCGCCA GCACCGACAT CGGAACCCAA ACCGAAGAAA GGTAGGGCGA
AGTAGGGTGG CGTCGGCGGT CGTGGCTGTA GCCTTGGGTT TGGCTTCTTT CCATCCCGCT

      610        620        630        640        650        660
AAGATAAACC GAAGGGTAGA CCGAAAGACA AACCTCCGTG CGAACCGACG GTGAGTTCAC
TTCTATTTGG CTTCCCATCT GGCTTTCTGT TTGGAGGCAC GCTTGGCTGC CACTCAAGTG

      670        680        690        700        710        720
AACCACCGTC GCAGCCGACG GCAATGCCCG GCGGTCCGCC CGACGCGCCT CCCCCCGCCA
TTGGTGGCAG CGTCGGCTGC CGTTACGGGC CGCCAGGCGG GCTGCGCGGA GGGGGGCGGT

      730        740        750        760        770        780
TGCCGCAGAT GCCACCCGGC GTGGCCGAGG CGGTACAAGC TGCCGTGCAG GCGGCCGTGG
ACGGCGTCTA CGGTGGGCCG CACCGGCTCC GCCATGTTCG ACGGCACGTC CGCCGGCACC

                                             UL133
      790        800        810        820        830        840
CCGCGGCTCT ACAACAACAG CAGCAGCATC AGACCGGAAC GTAACCCGCC CCCGGTGCGA
GGCGCCGAGA TGTTGTTGTC GTCGTCGTAG TCTGGCCTTG CATTGGGCGG GGGCCACGCT

      850        860        870        880        890        900
TAAGGAATTT TCCGACTTGG CGCACATCTC CTTCCTCAAT GTTTGGACAA TAAACACATT
ATTCCTTAAA AGGCTGAACC GCGTGTAGAG GAAGGAGTTA CAAACCTGTT ATTTGTGTAA

                                             UL135
      910        920        930        940        950        960
CCTTGCCAAA AAATGACGTT TCCAGAAATC CAAGGCATAA ATGTCCGTAC ACCGGCCCTT
GGAACGGTTT TTTACTGCAA AGGTCTTTAG GTTCCGTATT TACAGGCATG TGGCCGGGAA
```

FIG._1A-2

```
       970        980        990       1000       1010       1020
CCCAACACGG AGTTTGAGAT TCCAAGCAGG AGAGAAGATC ATGGTGTGGA TATGGCTCGG
GGGTTGTGCC TCAAACTCTA AGGTTCGTCC TCTCTTCTAG TACCACACCT ATACCGAGCC

      1030       1040       1050       1060       1070       1080
CATCGGGCTC CTCGGCGGTA CCGGACTGGC TTCCCTGGTC CTGGCCATTT CCTTATTTAC
GTAGCCCGAG GAGCCGCCAT GGCCTGACCG AAGGGACCAG GACCGGTAAA GGAATAAATG
                                             UL134

      1090       1100       1110       1120       1130       1140
CCAGCGCCGA GGCCGCAAGC GATCCGACGA GACTTCGTCG CGAGGCCGGC TCCCGGGTGC
GGTCGCGGCT CCGGCGTTCG CTAGGCTGCT CTGAAGCAGC GCTCCGGCCG AGGGCCCACG

      1150       1160       1170       1180       1190       1200
TGCTTCTGAT AAGCGTGGTG CCTGCGCGTG CTGCTATCGA AATCCGAAAG AAGACGTCGT
ACGAAGACTA TTCGCACCAC GGACGCGCAC GACGATAGCT TTAGGCTTTC TTCTGCAGCA

      1210       1220       1230       1240       1250       1260
CGAGCCGCTG GATCTGGAAC TGGGGCTCAT GCGGGTGGAC ACCCACCCGC CGACGCCGCA
GCTCGGCGAC CTAGACCTTG ACCCCGAGTA CGCCCACCTG TGGGTGGGCG GCTGCGGCGT

      1270       1280       1290       1300       1310       1320
GGTGCCGCGG TGTACGTCGC TCTACATAGG AGAGGATGGT CTGCCGATAG ATAAACCCGA
CCACGGCGCC ACATGCAGCG AGATGTATCC TCTCCTACCA GACGGCTATC TATTTGGGCT

      1330       1340       1350       1360       1370       1380
GTTTCCTCCG GCGCGGTTCG AGATCCCCGA CGTATCCACG CCGGGAACGC CGACCAGCAT
CAAAGGAGGC CGCGCCAAGC TCTAGGGGCT GCATAGGTGC GGCCCTTGCG GCTGGTCGTA

      1390       1400       1410       1420       1430       1440
CGGCCGATCT CCGTCGCATT GCTCCTCGTC GAGCTCTTTG TCGTCCTCGA CCAGCGTCGA
GCCGGCTAGA GGCAGCGTAA CGAGGAGCAG CTCGAGAAAC AGCAGGAGCT GGTCGCAGCT
```

FIG._1B-1

```
      1450       1460       1470       1480       1490       1500
CACGGTGCTG TATCAGCCGC CGCCATCCTG GAAGCCACCT CCGCCGCCCG GGCGCAAGAA
GTGCCACGAC ATAGTCGGCG GCGGTAGGAC CTTCGGTGGA GGCGGCGGGC CCGCGTTCTT

      1510       1520       1530       1540       1550       1560
GCGGCCGCCT ACGCCGCCGG TCCGGGCCCC CACCACGCGG CTGTCGTCGC ACAGACCCCC
CGCCGGCGGA TGCGGCGGCC AGGCCCGGGG GTGGTGCGCC GACAGCAGCG TGTCTGGGGG

      1570       1580       1590       1600       1610       1620
GACGCCGATA CCCGCGCCGC GTAAGAACCT GAGCACGCCG CCCACCAAGA AAACGCCGCC
CTGCGGCTAT GGGCGCGGCG CATTCTTGGA CTCGTGCGGC GGGTGGTTCT TTTGCGGCGG

      1630       1640       1650       1660       1670       1680
GCCCACGAAA CCCAAGCCGG TCGGCTGGAC ACCGCCGGTG ACACCCAGGC CCTTCCCGAA
CGGGTGCTTT GGGTTCGGCC AGCCGACCTG TGGCGGCCAC TGTGGGTCCG GGAAGGGCTT

      1690       1700       1710       1720       1730       1740
AACGCCGACG CCACAAAAGC CGCCGCGGAA TCCGAGACTA CCGCGCACCG TCGGTCTGGA
TTGCGGCTGC GGTGTTTTCG GCGGCGCCTT AGGCTCTGAT GGCGCGTGGC AGCCAGACCT

      1750       1760       1770       1780       1790       1800
GAATCTCTCG AAGGTGGGAC TCTCGTGTCC CTGTCCCCGA CCCCGCACGC CGACGGAGCC
CTTAGAGAGC TTCCACCCTG AGAGCACAGG GACAGGGGCT GGGGCGTGCG GCTGCCTCGG

      1810       1820       1830       1840       1850       1860
GACCACGCTG CCTATCGTGT CGGTTTCCGA GCTAGCCCCG CCTCCTCGAT GGTCGGACAT
CTGGTGCGAC GGATAGCACA GCCAAAGGCT CGATCGGGGC GGAGGAGCTA CCAGCCTGTA
```

FIG._1B-2

```
      1870       1880       1890       1900       1910       1920
CGAGGAACTC TTGGAACAGG CGGTGCAGAG CGTCATGAAG GACGCCGAGT CGATGCAGAT
GCTCCTTGAG AACCTTGTCC GCCACGTCTC GCAGTACTTC CTGCGGCTCA GCTACGTCTA

UL135 1930       1940       1950       1960       1970       1980
GACCTGAGAC CGAAAGAGCG AGCGCGTCCG TTGTACAGTT GTATAGCAGC ACACGCCTTC
CTGGACTCTG GCTTTCTCGC TCGCGCAGGC AACATGTCAA CATATCGTCG TGTGCGGAAG

      1990       2000       2010       2020 UL136 2030       2040
CCTCTTTTTC ACCGCAGCTA AGAGAGAGAA AGAGAGTATG TCAGTCAAGG GCGTGGAGAT
GGAGAAAAAG TGGCGTCGAT TCTCTCTCTT TCTCTCATAC AGTCAGTTCC CGCACCTCTA

      2050       2060       2070       2080       2090       2100
GCCAGAAATG ACGTGGGACT TGGACGTTAG AAATAAATGG CGGCGTCGAA AGGCCCTGAG
CGGTCTTTAC TGCACCCTGA ACCTGCAATC TTTATTTACC GCCGCAGCTT TCCGGGACTC

      2110       2120       2130       2140       2150       2160
TCGCATTCAC CGGTTCTGGG AATGTCGGCT ACGGGTGTGG TGGCTGAGTG ACGCCGGCGT
AGCGTAAGTG GCCAAGACCC TTACAGCCGA TGCCCACACC ACCGACTCAC TGCGGCCGCA

      2170       2180       2190       2200       2210       2220
AAGAGAAACC GACCCACCGC GTCCCCGACG CCGCCCGACT TGGATGACCG CGGTGTTTCA
TTCTCTTTGG CTGGGTGGCG CAGGGGCTGC GGCGGGCTGA ACCTACTGGC GCCACAAAGT

      2230       2240       2250       2260       2270       2280
CGTTATCTGT GCCGTTTTGC TTACGCTTAT GATTATGGCC ATCGGCGCGC TCATCGCGTA
GCAATAGACA CGGCAAAACG AATGCGAATA CTAATACCGG TAGCCGCGCG AGTAGCGCAT

      2290       2300       2310       2320       2330       2340
CTTAAGATAT TACCACCAGG ACAGTTGGCG AGACATGCTC CACGATCTAT TTTGCGGCTG
GAATTCTATA ATGGTGGTCC TGTCAACCGC TCTGTACGAG GTGCTAGATA AAACGCCGAC
```

FIG._1C-1

```
      2350       2360       2370       2380       2390       2400
TCATTATCCC GAGAAGTGCC GTCGGCACCA CGAGCGGCAG AGAAGGAGAC GGCAAGCCAT
AGTAATAGGG CTCTTCACGG CAGCCGTGGT GCTCGCCGTC TCTTCCTCTG CCGTTCGGTA

      2410       2420       2430       2440       2450       2460
GGATGTGCCC GACCCGGAAC TCGGCGACCC GGCCCGCCGG CCGTTGAACG GAGCTATGTA
CCTACACGGG CTGGGCCTTG AGCCGCTGGG CCGGGCGGCC GGCAACTTGC CTCGATACAT

      2470       2480       2490       2500       2510       2520
CTACGGCAGC GGCTGTCGCT TCGACACGGT GGAAATGGTG GACGAGACGA GACCCGCGCC
GATGCCGTCG CCGACAGCGA AGCTGTGCCA CCTTTACCAC CTGCTCTGCT CTGGGCGCGG

      2530       2540       2550       2560       2570       2580
GCCGGCGCTG TCATCGCCCG AAACCGGCGA CGATAGCAAC GACGACGCGG TTGCCGGCGG
CGGCCGCGAC AGTAGCGGGC TTTGGCCGCT GCTATCGTTG CTGCTGCGCC AACGGCCGCC

      2590       2600       2610       2620       2630       2640
AGGTGCTGGC GGGGTAACAT CACCCGCGAC TCGTACGACG TCGCCGAACG CACTGCTGCC
TCCACGACCG CCCCATTGTA GTGGGCGCTG AGCATGCTGC AGCGGCTTGC GTGACGACGG
                     UL137
      2650       2660       2670       2680       2690       2700
AGAATGGATG GATGCGGTGC ATGTGGCGGT CCAAGCCGCC GTTCAAGCGA CCGTGCAAGT
TCTTACCTAC CTACGCCACG TACACCGCCA GGTTCGGCGG CAAGTTCGCT GGCACGTTCA

      2710       2720       2730 UL136 2740       2750       2760
AAGTGGCCCG CGGGAGAACG CCGTATCTCC CGCTACGTAA GAGGGTTGAG GGGGCCGTTC
TTCACCGGGC GCCCTCTTGC GGCATAGAGG GCGATGCATT CTCCCAACTC CCCCGGCAAG

      2770       2780       2790       2800       2810       2820
CCGCGCGAGT GCTGTACAAA AGAGAGAGAC TGGGACGTAG ATCCGGACAG AGGACGGTCA
GGCGCGCTCA CGACATGTTT TCTCTCTCTG ACCCTGCATC TAGGCCTGTC TCCTGCCAGT
```

FIG._1C-2

```
UL138     2830       2840       2850       2860       2870       2880
CCATGGACGA TCTGCCGCTG AATGTCGGGT TACCCATCAT CGGCGTGATG CTCGTGCTGA
GGTACCTGCT AGACGGCGAC TTACAGCCCA ATGGGTAGTA GCCGCACTAC GAGCACGACT

          2890       2900       2910       2920       2930       2940
TCGTGGCCAT CCTCTGCTAT CTGGCTTACC ACTGGCACGA CACCTTCAAA CTGGTGCGCA
AGCACCGGTA GGAGACGATA GACCGAATGG TGACCGTGCT GTGGAAGTTT GACCACGCGT
UL137
          2950       2960       2970       2980       2990       3000
TGTTTCTGAG CTACCGCTGG CTGATCCGCT GTTGCGAGCT GTACGGGGAG TACGAGCGCC
ACAAAGACTC GATGGCGACC GACTAGGCGA CAACGCTCGA CATGCCCCTC ATGCTCGCGG

          3010       3020       3030       3040       3050       3060
GGTTCGCGGA CCTGTCGTCT CTGGGCCTCG GCGCCGTACG GCGGGAGTCG GACAGACGAT
CCAAGCGCCT GGACAGCAGA GACCCGGAGC CGCGGCATGC CGCCCTCAGC CTGTCTGCTA

          3070       3080       3090       3100       3110       3120
ACCGTTTCTC CGAACGGCCC GACGAGATCT TGGTCCGTTG GGAGGAAGTG TCTTCCCAGT
TGGCAAAGAG GCTTGCCGGG CTGCTCTAGA ACCAGGCAAC CCTCCTTCAC AGAAGGGTCA

          3130       3140       3150       3160       3170       3180
GCAGCTACGC GTCGTCGCGG ATAACAGACC GCCGTGTGGG TTCATCGTCT TCGTCGTCGG
CGTCGATGCG CAGCAGCGCC TATTGTCTGG CGGCACACCC AAGTAGCAGA AGCAGCAGCC

          3190       3200       3210       3220       3230       3240
TCCACGTCGC TAGCCAGAGA AACAGCGTGC CTCCGCCGGA CATGGCGGTG ACGGCGCCGC
AGGTGCAGCG ATCGGTCTCT TTGTCGCACG GAGGCGGCCT GTACCGCCAC TGCCGCGGCG

          3250       3260       3270       3280       3290       3300
TGACCGACGT CGATCTGTTG AAACCCGTGA CGGGATCCGC GACGCAGTTC ACCACCGTAG
ACTGGCTGCA GCTAGACAAC TTTGGGCACT GCCCTAGGCG CTGCGTCAAG TGGTGGCATC
```

FIG._1D-1

```
      3310       3320       3330       3340       3350       3360
CCATGGTACA TTATCATCAA GAGTACACGT GAATGAGAAA AAGAAAAAAG AGGGGAGCGG
GGTACCATGT AATAGTAGTT CTCATGTGCA CTTACTCTTT TTCTTTTTTC TCCCCTCGCC
                                UL138

      3370       3380       3390       3400       3410       3420
ATCGCGATAA TGTCGCTTTG ACATTCTCTG CTCGATCTAC TCAGCGTCTG CACGAAACGG
TAGCGCTATT ACAGCGAAAC TGTAAGAGAC GAGCTAGATG AGTCGCAGAC GTGCTTTGCC

      3430       3440       3450       3460       3470       3480
CATCCGCACG GAGGCGAGCC CAAGCGTATC TGCAGCAAGC GGTTCTTTCC CTCGGTGATG
GTAGGCGTGC CTCCGCTCGG GTTCGCATAG ACGTCGTTCG CCAAGAAAGG GAGCCACTAC

      3490       3500       3510       3520       3530       3540
GTGGCAGCAT CGGTGGCGGG AGCTTGTTCG GACGATGGAC GGTGAGGAGT CCCTGGCGAT
CACCGTCGTA GCCACCGCCC TCGAACAAGC CTGCTACCTG CCACTCCTCA GGGACCGCTA

      3550       3560       3570       3580       3590       3600
CAGGCGGCTC CCGGGTGTGG AGTTCAACGG GTGGTAATGG TGGCGGTGAT CGGTGTTAGA
GTCCGCCGAG GGCCCACACC TCAAGTTGCC CACCATTACC ACCGCCACTA GCCACAATCT

      3610       3620       3630       3640       3650       3660
AAACGGTGGC CCTGGCAAAC ATATATCTAC TGTAAACCCT CTGCTCTGTT AATAAAAAGC
TTTGCCACCG GGACCGTTTG TATATAGATG ACATTTGGGA GACGAGACAA TTATTTTTCG

      3670       3680       3690       3700       3710       3720
ACACTTTTCA CATGAGTTCG TAATTTTATT GTGTAGTGGA AATTTTTACG TCATTGGGAA
TGTGAAAAGT GTACTCAAGC ATTAAAATAA CACATCACCT TTAAAAATGC AGTAACCCTT

      3730       3740       3750       3760       3770       3780
ACCCCAGAAT GAAAGAGTAT AATGTGCATA TCACCGGGGG TTCCCTGTCA GTACGAATGT
TGGGGTCTTA CTTTCTCATA TTACACGTAT AGTGGCCCCC AAGGGACAGT CATGCTTACA
```

FIG._1D-2

```
      3790       3800       3810       3820       3830       3840
ACACAACGCG GGTTACATTA CGATAAACTT TCCGGTAAAA CGATGCCGAT ACAGCGTGTA
TGTGTTGCGC CCAATGTAAT GCTATTTGAA AGGCCATTTT GCTACGGCTA TGTCGCACAT

      3850       3860       3870       3880       3890       3900
TAACGCTGAT TGTTACGACA AACGAGTTGG TATATCCATT ATATAGTAAC GAACATGCTG
ATTGCGACTA ACAATGCTGT TTGCTCAACC ATATAGGTAA TATATCATTG CTTGTACGAC
                                                          UL139
      3910       3920       3930       3940       3950       3960
TGGATATTAG TTTTATTTGC ACTCGCCGCA TCGGCGAGTG AAACCACTAC AGGTACCAGC
ACCTATAATC AAAATAAACG TGAGCGGCGT AGCCGCTCAC TTTGGTGATG TCCATGGTCG

      3970       3980       3990       4000       4010       4020
TCTAATTCCA GTCAATCTAC TAGTGCTACC GCCAACACGA CCGTATCGAC ATGTATTAAT
AGATTAAGGT CAGTTAGATG ATCACGATGG CGGTTGTGCT GGCATAGCTG TACATAATTA

      4030       4040       4050       4060       4070       4080
GCCTCTAACG GCAGTAGCTG GACAGTACCA CAGCTCGCGC TGCTTGCCGC TAGCGGCTGG
CGGAGATTGC CGTCATCGAC CTGTCATGGT GTCGAGCGCG ACGAACGGCG ATCGCCGACC

      4090       4100       4110       4120       4130       4140
ACATTATCTG GACTCCTTCT CTTATTTACC TGCTGCTTTT GCTGCTTTTG GCTAGTACGT
TGTAATAGAC CTGAGGAAGA GAATAAATGG ACGACGAAAA CGACGAAAAC CGATCATGCA

      4150       4160       4170       4180       4190       4200
AAAATCTGCA GCTGCTGCGG CAACTCCTCC GAGTCAGAGA GCAAAACAAC CCACGCGTAC
TTTTAGACGT CGACGACGCC GTTGAGGAGG CTCAGTCTCT CGTTTTGTTG GGTGCGCATG

      4210       4220       4230       4240       4250       4260
ACCAATGCCG CATTCACTTC TTCCGACGCA ACGTTACCCA TGGGCACTAC AGGGTCGTAC
TGGTTACGGC GTAAGTGAAG AAGGCTGCGT TGCAATGGGT ACCCGTGATG TCCCAGCATG
```

FIG._1E-1

```
      4270       4280       4290       4300       4310       4320
ACTCCCCCAC AGGACGGCTC ATTTCCACCT CCGCCTCGGT GACGTAGGCT AAACCGAAAC
TGAGGGGGTG TCCTGCCGAG TAAAGGTGGA GGCGGAGCCA CTGCATCCGA TTTGGCTTTG
                                                UL139

      4330       4340       4350       4360       4370       4380
CCACGTTGAA CCTAACGCGG TTTCGGAAGG CCTGAGACGT CACTTTCACA ATGACGTCCG
GGTGCAACTT GGATTGCGCC AAAGCCTTCC GGACTCTGCA GTGAAAGTGT TACTGCAGGC

      4390       4400       4410       4420       4430       4440
TATACACGTT CATCATAAAA CACCGTAGAG GCTAAGGCTT CGGTAGGGAG AGACCTCAAC
ATATGTGCAA GTAGTATTTT GTGGCATCTC CGATTCCGAA GCCATCCCTC TCTGGAGTTG

                                                UL140
      4450       4460       4470       4480       4490       4500
TGTTCCTGAT GAGCACCCGT GCTCTCATCT CTTCAGACTT GTCATGACCC CCGCTCAGAC
ACAAGGACTA CTCGTGGGCA CGAGAGTAGA GAAGTCTGAA CAGTACTGGG GGCGAGTCTG

      4510       4520       4530       4540       4550       4560
TAACGCGACT ACCACCGTGC ACCCGCACGA CGCAAAAAAC GGCAGCGGCG GTAGTGCCCT
ATTGCGCTGA TGGTGGCACG TGGGCGTGCT GCGTTTTTTG CCGTCGCCGC CATCACGGGA

      4570       4580       4590       4600       4610       4620
GCCGACCCTC GTCGTTTTCG GCTTTATCGT TACGCTACTT TTCTTTCTCT TTATGCTCTA
CGGCTGGGAG CAGCAAAAGC CGAAATAGCA ATGCGATGAA AAGAAAGAGA AATACGAGAT

      4630       4640       4650       4660       4670       4680
CTTTTGGAAC AACGACGTGT TCCGTAAGCT GCTCCGTGCG CTTGGATCCA GCGCTGTTGC
GAAAACCTTG TTGCTGCACA AGGCATTCGA CGAGGCACGC GAACCTAGGT CGCGACAACG

      4690       4700       4710       4720       4730       4740
GACCGCTTCG ACGCGTGGCA AGACGAGGTC ATCTACCGTC GTCCATCACG TCGTTCCCAG
CTGGCGAAGC TGCGCACCGT TCTGCTCCAG TAGATGGCAG CAGGTAGTGC AGCAAGGGTC
```

FIG._1E-2

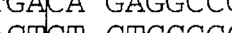

```
      4750       4760       4770       4780       4790       4800
AGCGACGACG AGAGTCGTAC TAACAGCGTG TCATCGTACG TTCTTTTATC ACCCGCGTCC
TCGCTGCTGC TCTCAGCATG ATTGTCGCAC AGTAGCATGC AAGAAAATAG TGGGCGCAGG

      4810       4820 UL140 4830       4840       4850       4860
GATGGCGGTT TTGACAACCC GGCACTGACA GAGGCCGTCG ACAGCGTGGA CGACTGGGCG
CTACCGCCAA AACTGTTGGG CCGTGACTGT CTCCGGCAGC TGTCGCACCT GCTGACCCGC

      4870       4880       4890       4900       4910       4920
ACCACCTCGG TTTTCTACGC CACGTCCGAC GAAACGGCGG ACGCCGAGCG CCGAGACTCG
TGGTGGAGCC AAAAGATGCG GTGCAGGCTG CTTTGCCGCC TGCGGCTCGC GGCTCTGAGC

      4930       4940       4950       4960       4970       4980
CAGCAACTGC TCATCGAGCT TCCGCCGGAG CCGCTCCCGC CCGACGTGGT GGCGGCCATG
GTCGTTGACG AGTAGCTCGA AGGCGGCCTC GGCGAGGGCG GGCTGCACCA CCGCCGGTAC

      4990       5000       5010       5020       5030       5040
CAGAAAGCAG TGAAACGCGC TGTACAGAAC GCACTACGAC ACAGCCACGA CTCTTGGCAG
GTCTTTCGTC ACTTTGCGCG ACATGTCTTG CGTGATGCTG TGTCGGTGCT GAGAACCGTC

      5050       5060       5070       5080       5090       5100 UL141
CTTCATCAGA CCCTGTGACG CCAGATGAAC GTTCCTTCTT AAACATCCGA GGTAGCAATG
GAAGTAGTCT GGGACACTGC GGTCTACTTG CAAGGAAGAA TTTGTAGGCT CCATCGTTAC

      5110       5120       5130       5140       5150       5160
AGACAGGTCG CGTACCGCCG GCGACGCGAG AGTTCCTGCG CGGTGCTGGT CCACCACGTC
TCTGTCCAGC GCATGGCGGC CGCTGCGCTC TCAAGGACGC GCCACGACCA GGTGGTGCAG

      5170       5180       5190       5200       5210       5220
GGCCGCGACG GCGACGGCGA GGGGGAGGCA GCAAAAAAGA CCTGCAAAAA AACCGGACGC
CCGGCGCTGC CGCTGCCGCT CCCCCTCCGT CGTTTTTTCT GGACGTTTTT TTGGCCTGCG
```

FIG._1F-1

```
      5230       5240       5250       5260       5270       5280
TCAGTTGCGG GCATCCCGGG CGAGAAGCTG CGTCGCACGG TGGTCACCAC CACGCCGGCC
AGTCAACGCC CGTAGGGCCC GCTCTTCGAC GCAGCGTGCC ACCAGTGGTG GTGCGGCCGG

      5290       5300       5310       5320       5330       5340
CGACGTTTGA GCGGCCGACA CACGGAGCAG GAGCAGGCGG GCATGCGTCT CTGTGAAAAA
GCTGCAAACT CGCCGGCTGT GTGCCTCGTC CTCGTCCGCC CGTACGCAGA GACACTTTTT

      5350       5360       5370       5380       5390       5400
GGGAAGAAAA GAATCATCAT GTGCCGCCGG GAGTCGCTCC GAACTCTGCC GTGGCTGTTC
CCCTTCTTTT CTTAGTAGTA CACGGCGGCC CTCAGCGAGG CTTGAGACGG CACCGACAAG

      5410       5420       5430       5440       5450       5460
TGGGTGCTGT TGAGCTGCCC GCGACTCCTC GAATATTCTT CCTCTTCGTT CCCCTTCGCC
ACCCACGACA ACTCGACGGG CGCTGAGGAG CTTATAAGAA GGAGAAGCAA GGGGAAGCGG

      5470       5480       5490       5500       5510       5520
ACCGCTGACA TTGCCGAAAA GATGTGGGCC GAGAATTATG AGACCACGTC GCCGGCGCCG
TGGCGACTGT AACGGCTTTT CTACACCCGG CTCTTAATAC TCTGGTGCAG CGGCCGCGGC

      5530       5540       5550       5560       5570       5580
GTGTTGGTCG CCGAGGGAGA GCAAGTTACC ATCCCCTGCA CGGTCATGAC ACACTCCTGG
CACAACCAGC GGCTCCCTCT CGTTCAATGG TAGGGGACGT GCCAGTACTG TGTGAGGACC

      5590       5600       5610       5620       5630       5640
CCCATGGTCT CCATTCGCGC ACGTTTCTGT CGTTCCCACG ACGGCAGCGA CGAGCTCATC
GGGTACCAGA GGTAAGCGCG TGCAAAGACA GCAAGGGTGC TGCCGTCGCT GCTCGAGTAG
```

FIG._1F-2

```
      5650       5660       5670       5680       5690       5700
CTGGACGCCG TCAAAGGCCA TCGGCTGATG AACGGACTCC AGTACCGCCT GCCGTACGCC
GACCTGCGGC AGTTTCCGGT AGCCGACTAC TTGCCTGAGG TCATGGCGGA CGGCATGCGG

      5710       5720       5730       5740       5750       5760
ACTTGGAATT TCTCGCAATT GCATCTCGGC CAAATATTCT CGCTTACTTT TAACGTATCG
TGAACCTTAA AGAGCGTTAA CGTAGAGCCG GTTTATAAGA GCGAATGAAA ATTGCATAGC

      5770       5780       5790       5800       5810       5820
ATGGACACAG CCGGCATGTA CGAATGCGTG CTACGCAACT ACAGCCACGG CCTCATCATG
TACCTGTGTC GGCCGTACAT GCTTACGCAC GATGCGTTGA TGTCGGTGCC GGAGTAGTAC

      5830       5840       5850       5860       5870       5880
CAACGCTTCG TAATTCTCAC GCAGCTGGAG ACGCTCAGCC GGCCCGACGA ACCTTGCTGC
GTTGCGAAGC ATTAAGAGTG CGTCGACCTC TGCGAGTCGG CCGGGCTGCT TGGAACGACG

      5890       5900       5910       5920       5930       5940
ACACCGGCGT TAGGTCGCTA CTCGCTGGGA GACCAGATCT GGTCGCCGAC GCCCTGGCGT
TGTGGCCGCA ATCCAGCGAT GAGCGACCCT CTGGTCTAGA CCAGCGGCTG CGGGACCGCA

      5950       5960       5970       5980       5990       6000
CTACGGAATC ACGACTGCGG AACGTACCGC GGCTTTCAAC GCAACTACTT CTATATCGGC
GATGCCTTAG TGCTGACGCC TTGCATGGCG CCGAAAGTTG CGTTGATGAA GATATAGCCG

      6010       6020       6030       6040       6050       6060
CGCGCCGACG CCGAGGATTG CTGGAAACCC GCATGTCCGG ACGAGGAACC CGACCGCTGT
GCGCGGCTGC GGCTCCTAAC GACCTTTGGG CGTACAGGCC TGCTCCTTGG GCTGGCGACA

      6070       6080       6090       6100       6110       6120
TGGACAGTGA TACAGCGTTA CCGGCTCCCC GGCGACTGCT ACCGTTCGCA GCCACACCCG
ACCTGTCACT ATGTCGCAAT GGCCGAGGGG CCGCTGACGA TGGCAAGCGT CGGTGTGGGC
```

FIG._1G-1

```
      6130       6140       6150       6160       6170       6180
CCGAAATTTT TACCGGTGAC GCCAGCACCG CCGGCCGACA TAGACACCGG GATGTCTCCC
GGCTTTAAAA ATGGCCACTG CGGTCGTGGC GGCCGGCTGT ATCTGTGGCC CTACAGAGGG

      6190       6200       6210       6220       6230       6240
TGGGCCACTC GGGGAATCGC GGCGTTTTTG GGGTTTTGGA GTATTTTTAC CGTATGTTTC
ACCCGGTGAG CCCCTTAGCG CCGCAAAAAC CCCAAAACCT CATAAAAATG GCATACAAAG

      6250       6260       6270       6280       6290       6300
CTATGCTACC TGTGTTATCT GCAGTGTTGT GGACGCTGGT GTCCCACGCC GGGAAGGGGA
GATACGATGG ACACAATAGA CGTCACAACA CCTGCGACCA CAGGGTGCGG CCCTTCCCCT

      6310       6320       6330       6340       6350       6360
CGACGAGGCG GTGAGGGCTA TCGACGCCTA CCGACTTACG ATAGTTACCC CGGTGTTAGA
GCTGCTCCGC CACTCCCGAT AGCTGCGGAT GGCTGAATGC TATCAATGGG GCCACAATCT

             UL141
      6370 →     6380       6390       6400       6410       6420
AAGATGAAGA GGTGAGAACA CGTATAAAAT AAAAAAATAA TATGTTAAAA AATGCAGTGT
TTCTACTTCT CCACTCTTGT GCATATTTTA TTTTTTTATT ATACAATTTT TTACGTCACA

                                   UL142
      6430       6440       6450 →     6460       6470       6480
GTGAAGTGTG AATAGTGTGA TTAAAATATG CGGATTGAAT GGGTGTGGTG GTTATTCGGA
CACTTCACAC TTATCACACT AATTTTATAC GCCTAACTTA CCCACACCAC CAATAAGCCT

      6490       6500       6510       6520       6530       6540
TACTTTGTGT CATCCGTTGG GAGCGAACGG TCATTATCCT ATCGTTACCA CTTGGAATCT
ATGAAACACA GTAGGCAACC CTCGCTTGCC AGTAATAGGA TAGCAATGGT GAACCTTAGA

      6550       6560       6570       6580       6590       6600
AATTCATCTA CCAACGTGGT TTGCAACGGA AACATTTCCG TGTTTGTAAA CGGCACCCTA
TTAAGTAGAT GGTTGCACCA AACGTTGCCT TTGTAAAGGC ACAAACATTT GCCGTGGGAT
```

FIG._1G-2

```
      6610       6620       6630       6640       6650       6660
GGTGTGCGGT ATAACATTAC GGTAGGAATC AGTTCGTCTT TATTAATAGG ACACCTTACT
CCACACGCCA TATTGTAATG CCATCCTTAG TCAAGCAGAA ATAATTATCC TGTGGAATGA

      6670       6680       6690       6700       6710       6720
ATACAAGTAT TGGAATCATG GTTCACACCC TGGGTCCAAA ATAAAAGTTA CAACAAACAA
TATGTTCATA ACCTTAGTAC CAAGTGTGGG ACCCAGGTTT TATTTTCAAT GTTGTTTGTT

      6730       6740       6750       6760       6770       6780
CCCCTAGGTG ACACTGAAAC GCTTTATAAT ATAGATAGCG AAAACATTCA TCGCGTATCT
GGGGATCCAC TGTGACTTTG CGAAATATTA TATCTATCGC TTTTGTAAGT AGCGCATAGA

      6790       6800       6810       6820       6830       6840
CAATATTTTC ACACAAGATG GATAAAATCT CTGCAAGAGA ATCACACTTG CGACCTCACA
GTTATAAAAG TGTGTTCTAC CTATTTTAGA GACGTTCTCT TAGTGTGAAC GCTGGAGTGT

      6850       6860       6870       6880       6890       6900
AACAGTACAC CTACCTATAC ATATCAAGTA AACGTGAACA ACACGAATTA CCTAACACTA
TTGTCATGTG GATGGATATG TATAGTTCAT TTGCACTTGT TGTGCTTAAT GGATTGTGAT

      6910       6920       6930       6940       6950       6960
ACATCCTCGG GATGGCAAGA CCGTCTAAAT TACACCGTCA TAAATAGTAC ACACTTTAAC
TGTAGGAGCC CTACCGTTCT GGCAGATTTA ATGTGGCAGT ATTTATCATG TGTGAAATTG

      6970       6980       6990       7000       7010       7020
CTCACAGAAT CGAACATAAC CAGCATTCAA AAATATCTCA ACACTACCTG CATAGAAAGA
GAGTGTCTTA GCTTGTATTG GTCGTAAGTT TTTATAGAGT TGTGATGGAC GTATCTTTCT

      7030       7040       7050       7060       7070       7080
CTCCGTAACT ACACCTTGGA GTCCGTATAC ACCACAACTG TGCCTCAAAA CATAACAACA
GAGGCATTGA TGTGGAACCT CAGGCATATG TGGTGTTGAC ACGGAGTTTT GTATTGTTGT
```

FIG._1H-1

```
      7090       7100       7110       7120       7130       7140
TCTCAACACG CAACAACCAC TATGCACACA ATACCTCCAA ATACAATAAC AATTCAAAAT
AGAGTTGTGC GTTGTTGGTG ATACGTGTGT TATGGAGGTT TATGTTATTG TTAAGTTTTA

      7150       7160       7170       7180       7190       7200
ACAACTCAAA GCCATACTGT ACAGACGCCG TCTTTTAACG ACACACATAA CGTGACGAAA
TGTTGAGTTT CGGTATGACA TGTCTGCGGC AGAAAATTGC TGTGTGTATT GCACTGCTTT

      7210       7220       7230       7240       7250       7260
CACACGTTAA ACATAAGCTA CGTTTTATCA CAAAAAACGA ATAACACAAC ATCACCGTGG
GTGTGCAATT TGTATTCGAT GCAAAATAGT GTTTTTTGCT TATTGTGTTG TAGTGGCACC

      7270       7280       7290       7300       7310       7320
ATATATGCCA TACCTATGGG CGCTACAGCC ACAATAGGCG CCGGTTTATA TATCGGGAAA
TATATACGGT ATGGATACCC GCGATGTCGG TGTTATCCGC GGCCAAATAT ATAGCCCTTT

                                 UL143      UL142
      7330       7340       7350       7360       7370       7380
CACTTTACGC CGGTTAAGTT CGTATACGAG GTATGGCGCG GTCAGTAAAG ACGATTCGGA
GTGAAATGCG GCCAATTCAA GCATATGCTC CATACCGCGC CAGTCATTTC TGCTAAGCCT

      7390       7400       7410       7420       7430       7440
TTCAACACAT ATACTCCCCA CGATCCTCGA ACACCTTACA GCATATGAGC AAAAAACAAG
AAGTTGTGTA TATGAGGGGT GCTAGGAGCT TGTGGAATGT CGTATACTCG TTTTTTGTTC

      7450       7460       7470       7480       7490       7500
AAAGTATAGC CACAATCACA TTTGGGCGAA TAACATGCTG TCATCCACTA GCGTCTATTA
TTTCATATCG GTGTTAGTGT AAACCCGCTT ATTGTACGAC AGTAGGTGAT CGCAGATAAT

      7510       7520       7530       7540       7550       7560
ATCTAATGTT TAACGGGAGC TGTACTGTCA CCGTTAAAAT ATCCATGGGA ATCAACGGGT
TAGATTACAA ATTGCCCTCG ACATGACAGT GGCAATTTTA TAGGTACCCT TAGTTGCCCA
```

FIG._1H-2

```
      7570       7580       7590       7600       7610       7620
CAACCAACGT CCATCAGCTT GTGATTGTGC TCCATCTGGG TAACCGCTGT CAGCCTTGGC
GTTGGTTGCA GGTAGTCGAA CACTAACACG AGGTAGACCC ATTGGCGACA GTCGGAACCG

UL143 7630       7640       7650       7660       7670       7680
GACAGGTGTA ATCACAGCTG TCACATAACT CACGAAGCCT CCAATCACAG CAGCACACAT
CTGTCCACAT TAGTGTCGAC AGTGTATTGA GTGCTTCGGA GGTTAGTGTC GTCGTGTGTA

      7690       7700       7710       7720       7730       7740
AGTCCTAACG CCATTGGCGT GTATAAAAGT TCGGAAAACT TGACGGTTGT ACGGCACGAC
TCAGGATTGC GGTAACCGCA CATATTTTCA AGCCTTTTGA ACTGCCAACA TGCCGTGCTG

      7750       7760       7770       7780       7790       7800
AAATCGATGT AGTGGTATGT TTTTCCAGCA GAGACCGTGT GCGGTCTCTT AGGTTCGCTA
TTTAGCTACA TCACCATACA AAAAGGTCGT CTCTGGCACA CGCCAGAGAA TCCAAGCGAT

      7810       7820       7830       7840       7850       7860
TACTGTGGCT GGAAACTGGT TACCTGTGAA GATGGCTAAC TATCCTGTTC TGTCCTGGAA
ATGACACCGA CCTTTGACCA ATGGACACTT CTACCGATTG ATAGGACAAG ACAGGACCTT

      7870       7880       7890       7900       7910       7920
AAACTTTTGG CGTCGTAGGT GGACTTTGCA GTATGCGGGT TAGTGAAGTT ATGTCATTTA
TTTGAAAACC GCAGCATCCA CCTGAAACGT CATACGCCCA ATCACTTCAA TACAGTAAAT

      7930       7940       7950       7960       7970       7980
TTTACGTTTA CGATCTCGTA TTACAAACCG CGGAGAGGAT GATACCGTTC GGCCCCATGA
AAATGCAAAT GCTAGAGCAT AATGTTTGGC GCCTCTCCTA CTATGGCAAG CCGGGGTACT

      7990       8000       8010 UL144 8020       8030       8040
GTTATTTTTA TTCTTCCGGT AGGAGGCATG AAGCCTCTGA TAATGCTCAT CTGCTTTGCT
CAATAAAAAT AAGAAGGCCA TCCTCCGTAC TTCGGAGACT ATTACGAGTA GACGAAACGA
```

FIG._1I-1

```
      8050       8060       8070       8080       8090       8100
GTGATATTAT TGCAGCTTGG AGTGACTAAA GTGTGTCAGC ATAATGAAGT GCAACTGGGC
CACTATAATA ACGTCGAACC TCACTGATTT CACACAGTCG TATTACTTCA CGTTGACCCG

      8110       8120       8130       8140       8150       8160
AATGAGTGCT GCCCTCCGTG TGGTTCGGGA CAAAGAGTTA CTAAAGTATG CACGGATTAT
TTACTCACGA CGGGAGGCAC ACCAAGCCCT GTTTCTCAAT GATTTCATAC GTGCCTAATA

      8170       8180       8190       8200       8210       8220
ACCAGTGTAA CGTGTACCCC TTGCCCCAAC GGCACGTATG TATCGGGACT TTACAACTGT
TGGTCACATT GCACATGGGG AACGGGGTTG CCGTGCATAC ATAGCCCTGA AATGTTGACA

      8230       8240       8250       8260       8270       8280
ACCGATTGCA CTCAATGTAA CGTCACTCAG GTCATGATTC GTAACTGCAC TTCCACCAAT
TGGCTAACGT GAGTTACATT GCAGTGAGTC CAGTACTAAG CATTGACGTG AAGGTGGTTA

      8290       8300       8310       8320       8330       8340
AATACCGTAT GCGCACCTAA GAACCATACG TACTTTTCCA CTCCAGGCGT CCAACATCAC
TTATGGCATA CGCGTGGATT CTTGGTATGC ATGAAAAGGT GAGGTCCGCA GGTTGTAGTG

      8350       8360       8370       8380       8390       8400
AAACAACGAC AGCAAAATCA TACCGCACAT ATAACCGTCA AACAAGGAAA AAGCGGTCGT
TTTGTTGCTG TCGTTTTAGT ATGGCGTGTA TATTGGCAGT TTGTTCCTTT TTCGCCAGCA

      8410       8420       8430       8440       8450       8460
CATACTCTAG CCTGGTTGTC TCTCTTTATC TTTCTTGTGG GTATCATACT TTTAATTCTC
GTATGAGATC GGACCAACAG AGAGAAATAG AAAGAACACC CATAGTATGA AAATTAAGAG

      8470       8480       8490       8500       8510       8520
TATCTTATAG CCGCCTATCG GAGTGAGAGA TGCCAACAGT GTTGCTCAAT CGGCAAAATT
ATAGAATATC GGCGGATAGC CTCACTCTCT ACGGTTGTCA CAACGAGTTA GCCGTTTTAA
```

FIG._1I-2

```
           8530 UL144→ 8540        8550        8560        8570        8580
TTCTACCGCA CCCTGTAAGC TTCCTGTTGT TGTTTTTACA TCACGGTACG ATGAAGTCAC
AAGATGGCGT GGGACATTCG AAGGACAACA ACAAAAATGT AGTGCCATGC TACTTCAGTG

      8590        8600        8610        8620        8630        8640
ACAGATAATT ACAGATGAGC TGTTCATATT TTTTATTATT TTTTCCAATT CCTGCACTAA
TGTCTATTAA TGTCTACTCG ACAAGTATAA AAAATAATAA AAAAGGTTAA GGACGTGATT

      8650        8660        8670        8680        8690        8700
AAAAAGAAGC ACTTTACGGA ACCGTGTCTG AGTATCTGTG GGGAATTTAG GTACTTTTTG
TTTTTCTTCG TGAAATGCCT TGGCACAGAC TCATAGACAC CCCTTAAATC CATGAAAAAC

      8710        8720        8730        8740        8750        8760
CCGACGTCAG GAAAAATAAG TGTCGCCTAC ATAAGAGCCC GGTGCTATCG TGCTGTCACT
GGCTGCAGTC CTTTTTATTC ACAGCGGATG TATTCTCGGG CCACGATAGC ACGACAGTGA

      8770        8780        8790        8800        8810        8820
CTTTCTTGTT GCCTTCGATG TACGGCGTCC TGGCTCATTA CTACTCCTTC ATCAGTAGCC
GAAAGAACAA CGGAAGCTAC ATGCCGCAGG ACCGAGTAAT GATGAGGAAG TAGTCATCGG

      8830        8840        8850        8860        8870 UL145→ 8880
CCAGCGTTAT GGTTAATTTT AAGCATCATA ACGCCGTGCA GCTGTTATGT GCACGGACCC
GGTCGCAATA CCAATTAAAA TTCGTAGTAT TGCGGCACGT CGACAATACA CGTGCCTGGG

      8890        8900        8910        8920        8930        8940
GAGACGCACT GCCGGATGGG AACGTTTAAC CCATCATGCG TCGTATCACG CGAACTACGG
CTCTGCGTGA CGGCCTACCC TTGCAAATTG GGTAGTACGC AGCATAGTGC GCTTGATGCC

      8950        8960        8970        8980        8990        9000
GGCATACGCC GTGTTGATGG CTACATCGCA AAGAAAGTCC CTAGTGTTAC ATCGATACAG
CCGTATGCGG CACAACTACC GATGTAGCGT TTCTTTCAGG GATCACAATG TAGCTATGTC
```

FIG._1J-1

```
      9010       9020       9030       9040       9050       9060
TGCCGTGACA GCCGTGGCCC TGCAGCTCAT GCCTGTTGAG ATCGTCCGCA AGCTAGATCA
ACGGCACTGT CGGCACCGGG ACGTCGAGTA CGGACAACTC TAGCAGGCGT TCGATCTAGT

      9070       9080       9090       9100       9110       9120
GTCGGACTGG GTGCGGGGTG CCTGGATCGT GTCAGAGACT TTTCCAACTA GCGACCCCAA
CAGCCTGACC CACGCCCCAC GGACCTAGCA CAGTCTCTGA AAAGGTTGAT CGCTGGGGTT

                                            UL145
      9130       9140       9150       9160       9170       9180
AGGAGTTTGG AGCGACGATG ACTCCTCGAT GGGTGGAAGT GATGATTGAT GATGAGAACC
TCCTCAAACC TCGCTGCTAC TGAGGAGCTA CCCACCTTCA CTACTAACTA CTACTCTTGG

      9190       9200       9210       9220       9230       9240
TGACAAGAAA GACGAGAGAG AAATTTAGAG CTGTCATTGT AGAATTAGTC TAGATTCCTG
ACTGTTCTTT CTGCTCTCTC TTTAAATCTC GACAGTAACA TCTTAATCAG ATCTAAGGAC

      9250       9260       9270       9280       9290       9300
ATAATAAACA GTATCGATTT TGAAACCTAA TTGACGTGTG ATCGATTTTT AAACCTCTGT
TATTATTTGT CATAGCTAAA ACTTTGGATT AACTGCACAC TAGCTAAAAA TTTGGAGACA

      9310       9320       9330       9340       9350       9360
GTTGTGTGAT TGATTGGTAT GTGGGGGGAT CCGATTTCAA AGGGGGGTAC TTATCGGGAA
CAACACACTA ACTAACCATA CACCCCCCTA GGCTAAAGTT TCCCCCCATG AATAGCCCTT

      9370       9380       9390       9400       9410       9420
TTGATGTGTC ATGGACGCAG TTTTGAGCGA TTTTCCGGGA ATACCGGATA TTACGAATTA
AACTACACAG TACCTGCGTC AAAACTCGCT AAAAGGCCCT TATGGCCTAT AATGCTTAAT
```

FIG._1J-2

```
                                          UL146
      9430       9440       9450 →     9460       9470       9480
CTGGTAGTGA CGTAGATAAT AAAATTATAA TGCGATTAAT TTTTGGTGCG TTGATTATTT
GACCATCACT GCATCTATTA TTTTAATATT ACGCTAATTA AAAACCACGC AACTAATAAA

      9490       9500       9510       9520       9530       9540
TTTTAGCATA TGTGTATCAT TATGAGGTGA ATGGAACAGA ATTACGCTGC AGATGTCTTC
AAAATCGTAT ACACATAGTA ATACTCCACT TACCTTGTCT TAATGCGACG TCTACAGAAG

      9550       9560       9570       9580       9590       9600
ATAGAAAATG GCCGCCTAAT AAAATTATAT TGGGTAATTA TTGGCTTCAT CGCGATCCCA
TATCTTTTAC CGGCGGATTA TTTTAATATA ACCCATTAAT AACCGAAGTA GCGCTAGGGT

      9610       9620       9630       9640       9650       9660
GAGGGCCCGG ATGCGATAAA AATGAACATT TATTGTATCC AGACGGAAGG AAACCGCCTG
CTCCCGGGCC TACGCTATTT TTACTTGTAA ATAACATAGG TCTGCCTTCC TTTGGCGGAC

      9670       9680       9690       9700       9710       9720
GACCTGGAGT ATGTTTATCG CCCGATCACC TCTTCTCAAA ATGGTTAGAC AAACACAACG
CTGGACCTCA TACAAATAGC GGGCTAGTGG AGAAGAGTTT TACCAATCTG TTTGTGTTGC

      9730       9740       9750       9760       9770       9780
ATAATAGGTG GTATAATGTT AACATAACGA AATCACCAGG ACCGAGACGA ATAAATATAA
TATTATCCAC CATATTACAA TTGTATTGCT TTAGTGGTCC TGGCTCTGCT TATTTATATT

                     UL146
      9790       9800 ←     9810       9820       9830       9840
CCTTGATAGG TGTTAGAGGA TAATATTTAA TGTATGTTTT CAAACAGACA AGTTCGTTAA
GGAACTATCC ACAATCTCCT ATTATAAATT ACATACAAAA GTTTGTCTGT TCAAGCAATT

                                          UL147
      9850       9860       9870 ←     9880       9890       9900
AACAAAATAT TACAGTATGT GTTTAATATG GTGCTAACAT GGTTGCACCA TCCGGTTTCA
TTGTTTTATA ATGTCATACA CAAATTATAC CACGATTGTA CCAACGTGGT AGGCCAAAGT
```

FIG._1K-1

```
      9910       9920       9930       9940       9950       9960
AACTCGCATA TCAATCTGTT ATCGGTACGA CACCTGTCAT TAATCGCATA TATGTTACTT
TTGAGCGTAT AGTTAGACAA TAGCCATGCT GTGGACAGTA ATTAGCGTAT ATACAATGAA

      9970       9980       9990      10000      10010      10020
ACCATATGTC CCCTAGCCGT CCATGTTTTA GAACTAGAAG ATTACGACAG GCGCTGCCGT
TGGTATACAG GGGATCGGCA GGTACAAAAT CTTGATCTTC TAATGCTGTC CGCGACGGCA

     10030      10040      10050      10060      10070      10080
TGCAACAACC AAATTCTGTT GAATACCCTG CCGGTCGGAA CCGAATTGCT TAAGCCAATC
ACGTTGTTGG TTTAAGACAA CTTATGGGAC GGCCAGCCTT GGCTTAACGA ATTCGGTTAG

     10090      10100      10110      10120      10130      10140
GCAGCGAGCG AAAGCTGCAA TCGTCAGGAA GTGCTGGCTA TTTTAAAGGA CAAGGGAACC
CGTCGCTCGC TTTCGACGTT AGCAGTCCTT CACGACCGAT AAAATTTCCT GTTCCCTTGG

     10150      10160      10170      10180      10190      10200
AAGTGTCTCA ATCCTAACGC GCAAGCCGTG CGTCGTCACA TCAACCGGCT ATTTTTTCGG
TTCACAGAGT TAGGATTGCG CGTTCGGCAC GCAGCAGTGT AGTTGGCCGA TAAAAAAGCC

     10210      10220      10230      10240      10250      10260
TTAATCTTAG ACGAGGAACA ACGCATTTAC GACGTAGTGT CTACCAATAT TGAGTTCGGT
AATTAGAATC TGCTCCTTGT TGCGTAAATG CTGCATCACA GATGGTTATA ACTCAAGCCA

     10270      10280      10290      10300      10310      10320
GCCTGGCCAG TCCCTACGGC CTACAAAGCC TTTCTTTGGA AATACGCCAA GAGACTGAAC
CGGACCGGTC AGGGATGCCG GATGTTTCGG AAAGAAACCT TTATGCGGTT CTCTGACTTG

     10330      10340 UL147 10350      10360      10370      10380
TACCACCACT TCAGACTGCG CTGGTGATCA TGTCCCTATT TTACCGTGCG GTAGCTCTGG
ATGGTGGTGA AGTCTGACGC GACCACTAGT ACAGGGATAA AATGGCACGC CATCGAGACC
```

FIG._1K-2

```
     10390      10400      10410      10420      10430      10440
GCACGCTAAG CGCTTTGGTG TGGTACAGCA CTAGCATCCT CGCAGAGATT AACGAAAATT
CGTGCGATTC GCGAAACCAC ACCATGTCGT GATCGTAGGA GCGTCTCTAA TTGCTTTTAA

     10450      10460      10470      10480      10490      10500
CCTGCTCCTC ATCTTCTGCG GATCACGAAG ACTGCGAGGA ACCGGACGAG ATCGTTCGCG
GGACGAGGAG TAGAAGACGC CTAGTGCTTC TGACGCTCCT TGGCCTGCTC TAGCAAGCGC

     10510      10520      10530      10540      10550      10560
AAGAGCAAGA CTATCGGGCT CTGCTGGCCT TTTCCCTAGT GATTTGCGGT ACGCTCCTCG
TTCTCGTTCT GATAGCCCGA GACGACCGGA AAAGGGATCA CTAAACGCCA TGCGAGGAGC

     10570      10580      10590      10600      10610      10620
TCACTTGTGT GATCTGAGAC GTCATGCTGG TAGCGTTTAT GAGTCGGGCG GTGGCCGACA
AGTGAACACA CTAGACTCTG CAGTACGACC ATCGCAAATA CTCAGCCCGC CACCGGCTGT

                                 UL148
     10630      10640      10650 ->   10660      10670      10680
CGCCGCATTT CCTAACCCGC GCAGCATGTT GCGCTTGCTG TTCACGCTCG TCCTGCTGGC
GCGGCGTAAA GGATTGGGCG CGTCGTACAA CGCGAACGAC AAGTGCGAGC AGGACGACCG

     10690      10700      10710      10720      10730      10740
CCTCCACGGG CAGTCTGTCG GCGCTAGCCG CGACTATGTG CATGTTCGGC TACTGAGCTA
GGAGGTGCCC GTCAGACAGC CGCGATCGGC GCTGATACAC GTACAAGCCG ATGACTCGAT

     10750      10760      10770      10780      10790      10800
CCGAGGCGAC CCCCTGGTCT TCAAGCACAC TTTCTCGGGT GTGCGTCGAC CCTTCACCGA
GGCTCCGCTG GGGGACCAGA AGTTCGTGTG AAAGAGCCCA CACGCAGCTG GGAAGTGGCT

     10810      10820      10830      10840      10850      10860
GCTAGGCTGG GCTGCGTGTC GCGACTGGGA CAGTATGCAT TGCACACCCT TCTGGTCTAC
CGATCCGACC CGACGCACAG CGCTGACCCT GTCATACGTA ACGTGTGGGA AGACCAGATG
```

FIG._1L-1

```
     10870      10880      10890      10900      10910      10920
CGATCTGGAG CAGATGACCG ACTCGGTGCG GCGTTACAGC ACGGTGAGCC CCGGCAAGGA
GCTAGACCTC GTCTACTGGC TGAGCCACGC CGCAATGTCG TGCCACTCGG GGCCGTTCCT

     10930      10940      10950      10960      10970      10980
AGTGACGCTT CAGCTTCACG GGAACCAAAC CGTACAGCCG TCGTTTCTAA GCTTTACGTG
TCACTGCGAA GTCGAAGTGC CCTTGGTTTG GCATGTCGGC AGCAAAGATT CGAAATGCAC

     10990      11000      11010      11020      11030      11040
CCGCCTGCAG CTAGAACCCG TGGTGGAAAA TGTTGGCCTC TACGTGGCCT ACGTGGTCAA
GGCGGACGTC GATCTTGGGC ACCACCTTTT ACAACCGGAG ATGCACCGGA TGCACCAGTT

     11050      11060      11070      11080      11090      11100
CGACGGCGAA CGCCCACAAC AGTTTTTTAC ACCGCAGGTA GACGTGGTAC GCTTTGCTCT
GCTGCCGCTT GCGGGTGTTG TCAAAAAATG TGGCGTCCAT CTGCACCATG CGAAACGAGA

     11110      11120      11130      11140      11150      11160
ATATCTAGAA ACACTCTCCC GGATCGTGGA ACCGTTAGAA TCAGGTCGCC TGGCAGTGGA
TATAGATCTT TGTGAGAGGG CCTAGCACCT TGGCAATCTT AGTCCAGCGG ACCGTCACCT

     11170      11180      11190      11200      11210      11220
ATTTGATACG CCTGACCTAG CTCTGGCGCC CGATTTAGTA AGCAGCCTCT TCGTGGCCGG
TAAACTATGC GGACTGGATC GAGACCGCGG GCTAAATCAT TCGTCGGAGA AGCACCGGCC

     11230      11240      11250      11260      11270      11280
ACACGGCGAG ACCGACTTTT ACATGAACTG GACGCTGCGT CGCAGTCAGA CCCACTACCT
TGTGCCGCTC TGGCTGAAAA TGTACTTGAC CTGCGACGCA GCGTCAGTCT GGGTGATGGA

     11290      11300      11310      11320      11330      11340
GGAGGAGATG GCCTTACAGG TGGAGATTCT AAAACCCCGC GGCGTACGTC ACCGCGCTAT
CCTCCTCTAC CGGAATGTCC ACCTCTAAGA TTTTGGGGCG CCGCATGCAG TGGCGCGATA
```

FIG._1L-2

```
  11350      11360      11370      11380      11390      11400
TATCCACCAT CCGAAGCTAC AGCCGGGCGT TGGCCTGTGG ATAGATTTCT GCGTGTACCG
ATAGGTGGTA GGCTTCGATG TCGGCCCGCA ACCGGACACC TATCTAAAGA CGCACATGGC

  11410      11420      11430      11440      11450      11460
CTACAACGCG CGCCTGACCC GCGGCTACGT ACGATACACC CTGTCACCGA AAGCGCGCTT
GATGTTGCGC GCGGACTGGG CGCCGATGCA TGCTATGTGG GACAGTGGCT TTCGCGCGAA

  11470      11480      11490      11500      11510      11520
GCCCGCAAAA GCAGAGGGTT GGCTGGTGTC ACTAGACAGA TTCATCGTGC AGTACCTCAA
CGGGCGTTTT CGTCTCCCAA CCGACCACAG TGATCTGTCT AAGTAGCACG TCATGGAGTT

  11530      11540      11550      11560      11570      11580
CACATTGCTG ATTACAATGA TGGCGGCGAT ATGGGCTCGC GTTTTGATAA CCTACCTGGT
GTGTAACGAC TAATGTTACT ACCGCCGCTA TACCCGAGCG CAAAACTATT GGATGGACCA

  11590   UL148 11600      11610      11620      11630      11640
GTCGCGGCGT CGGTAGAGGC TTGCGGAAAC CACGTCCTCG TCACACGTCG TTCGCGGACA
CAGCGCCGCA GCCATCTCCG AACGCCTTTG GTGCAGGAGC AGTGTGCAGC AAGCGCCTGT

  11650      11660      11670   UL132 11680      11690      11700
TAGCAAGAAA TCCACGTCGC CACATCTCGA GAATGCCGGC CTTGCGGGGT CCCCTTCGCG
ATCGTTCTTT AGGTGCAGCG GTGTAGAGCT CTTACGGCCG GAACGCCCCA GGGGAAGCGC

  11710      11720      11730      11740      11750      11760
CAACATTCCT GGCCCTGGTC GCGTTCGGGT TGCTGCTTCA GATAGACCTC AGCGACGCTA
GTTGTAAGGA CCGGGACCAG CGCAAGCCCA ACGACGAAGT CTATCTGGAG TCGCTGCGAT

  11770      11780      11790      11800      11810      11820
CGAATGTGAC CAGCAGCACA AAAGTCCCTA CTAGCACCAG CAACAGAAAT AACGTCGACA
GCTTACACTG GTCGTCGTGT TTTCAGGGAT GATCGTGGTC GTTGTCTTTA TTGCAGCTGT
```

FIG._1M-1

```
     11830      11840      11850      11860      11870      11880
ACGCCACGAG TAGCGGACCC ACAACCGGGA TCAACATGAC CACCACCCAC GAGTCTTCCG
TGCGGTGCTC ATCGCCTGGG TGTTGGCCCT AGTTGTACTG GTGGTGGGTG CTCAGAAGGC

     11890      11900      11910      11920      11930      11940
TTCACAACGT GCGCAATAAC GAGATCATGA AAGTGCTGGC TATCCTCTTC TACATCGTGA
AAGTGTTGCA CGCGTTATTG CTCTAGTACT TTCACGACCG ATAGGAGAAG ATGTAGCACT

     11950      11960      11970      11980      11990      12000
CAGGCACCTC CATTTTCAGC TTCATAGCGG TACTGATCGC GGTAGTTTAC TCCTCGTGTT
GTCCGTGGAG GTAAAAGTCG AAGTATCGCC ATGACTAGCG CCATCAAATG AGGAGCACAA

     12010      12020      12030      12040      12050      12060
GCAAGCACCC GGGCCGCTTT CGTTTCGCCG ACGAAGAGGC CGTCAACCTG TTGGACGACA
CGTTCGTGGG CCCGGCGAAA GCAAAGCGGC TGCTTCTCCG GCAGTTGGAC AACCTGCTGT

     12070      12080      12090      12100      12110      12120
CGGACGACAG TGGCGGCAGC AGCCCGTTTG GCAGCGGTTC CCGACGAGGT TCTCAGATCC
GCCTGCTGTC ACCGCCGTCG TCGGGCAAAC CGTCGCCAAG GGCTGCTCCA AGAGTCTAGG

     12130      12140      12150      12160      12170      12180
CCGCCGGATT TTGTTCCTCG AGCCCTTATC AGCGGTTGGA AACTCGGGAC TGGGACGAGG
GGCGGCCTAA AACAAGGAGC TCGGGAATAG TCGCCAACCT TTGAGCCCTG ACCCTGCTCC

     12190      12200      12210      12220      12230      12240
AGGAGGAGGC GTCCGCGGCC CGCGAGCGCA TGAAACATGA TCCTGAGAAC GTCATCTATT
TCCTCCTCCG CAGGCGCCGG GCGCTCGCGT ACTTTGTACT AGGACTCTTG CAGTAGATAA

     12250      12260      12270      12280      12290      12300
TCAGAAAGGA TGGCAACTTG GACACGTCGT TCGTGAATCC CAATTATGGG AGAGGCTCGC
AGTCTTTCCT ACCGTTGAAC CTGTGCAGCA AGCACTTAGG GTTAATACCC TCTCCGAGCG
```

FIG._1M-2

```
            12310      12320      12330      12340      12350      12360
       CTTTGACCAT CGAATCTCAC CTCTCGGACA ATGAGGAGGA CCCCATCAGG TACTACGTTT
       GAAACTGGTA GCTTAGAGTG GAGAGCCTGT TACTCCTCCT GGGGTAGTCC ATGATGCAAA

            12370      12380      12390      12400      12410      12420
       CGGTGTACGA TGAACTGACC GCCTCGGAAA TGGAAGAACC TTCGAACAGC ACCAGCTGGC
       GCCACATGCT ACTTGACTGG CGGAGCCTTT ACCTTCTTGG AAGCTTGTCG TGGTCGACCG

            12430      12440      12450      12460      12470      12480
       AGATTCCCAA ACTAATGAAA GTTGCCATGC AACCCGTCTC GCTCAGAGAT CCCGAGTACG
       TCTAAGGGTT TGATTACTTT CAACGGTACG TTGGGCAGAG CGAGTCTCTA GGGCTCATGC

UL132 →     12490      12500      12510      12520      12530      12540
       ACTAGGCTTT TTTTTTTGTC TTTCGGTTCC AACTCTTTCC CCGCCCCATC ACCTCGCCTG
       TGATCCGAAA AAAAAAACAG AAAGCCAAGG TTGAGAAAGG GGCGGGGTAG TGGAGCGGAC

            12550      12560      12570      12580      12590      12600
       TACTATGTGT ATGATGTCTC ATAATAAAGC TTTCTTTCTC AGTCTGCAAC ATGCAGCTGT
       ATGATACACA TACTACAGAG TATTATTTCG AAAGAAAGAG TCAGACGTTG TACGTCGACA

            12610      12620      12630      12640      12650      12660
       GTCGGGTGTG GCTGTCTGTT TGTCTGTGCG CCGTGGTGCT GGGTCAGTGC CAGCGGGAAA
       CAGCCCACAC CGACAGACAA ACAGACACGC GGCACCACGA CCCAGTCACG GTCGCCCTTT

            12670      12680      12690      12700      12710      12720
       CCGCGGAAAA AAACGATTAT TACCGAGTAC CGCATTACTG GGACGCGTGC TCTCGCGCGC
       GGCGCCTTTT TTTGCTAATA ATGGCTCATG GCGTAATGAC CCTGCGCACG AGAGCGCGCG

            12730      12740      12750      12760      12770      12780
       TGCCCGACCA AACCCGTTAC AAGTATGTGG AACAGCTCGT GGACCTCACG TTGAACTACC
       ACGGGCTGGT TTGGGCAATG TTCATACACC TTGTCGAGCA CCTGGAGTGC AACTTGATGG
```

FIG._1N-1

```
     12790      12800      12810      12820      12830      12840
ACTACGATGC GAGCCACGGC TTGGACAACT TTGACGTGCT CAAGAGGTGA GGGTACGCGC
TGATGCTACG CTCGGTGCCG AACCTGTTGA AACTGCACGA GTTCTCCACT CCCATGCGCG

     12850      12860      12870      12880      12890      12900
TAAAGGTGCA TGACAACGGG AAGGTAAGGG CGAACGGGTA ACGGCTAAGT AACCGCATGG
ATTTCCACGT ACTGTTGCCC TTCCATTCCC GCTTGCCCAT TGCCGATTCA TTGGCGTACC

     12910      12920      12930      12940      12950      12960
GGTATGAAAT GACGTTTGGA ACCTGTGCTT GCAGAATCAA CGTGACCGAG GTGTCGTTGC
CCATACTTTA CTGCAAACCT TGGACACGAA CGTCTTAGTT GCACTGGCTC CACAGCAACG

     12970      12980      12990      13000      13010      13020
TCATCAGCGA CTTTAGACGT CAGAACCGTC GCGGCGGCAC CAACAAAAGG ACCACGTTCA
AGTAGTCGCT GAAATCTGCA GTCTTGGCAG CGCCGCCGTG GTTGTTTTCC TGGTGCAAGT

     13030      13040      13050      13060      13070      13080
ACGCCGCCGG TTCGCTGGCG CCACACGCCC GGAGCCTCGA GTTCAGCGTG CGGCTCTTTG
TGCGGCGGCC AAGCGACCGC GGTGTGCGGG CCTCGGAGCT CAAGTCGCAC GCCGAGAAAC

                                UL130
     13090      13100      13110 --->  13120      13130      13140
CCAACTAGCC TGCGTCACGG GAAATAATAT GCTGCGGCTT CTGCTTCGTC ACCACTTTCA
GGTTGATCGG ACGCAGTGCC CTTTATTATA CGACGCCGAA GACGAAGCAG TGGTGAAAGT

     13150      13160      13170      13180      13190      13200
CTGCCTGCTT CTGTGCGCGG TTTGGGCAAC GCCCTGTCTG GCGTCTCCGT GGTCGACGCT
GACGGACGAA GACACGCGCC AAACCCGTTG CGGGACAGAC CGCAGAGGCA CCAGCTGCGA
```

FIG._1N-2

```
     13210      13220      13230      13240      13250      13260
AACGGCAAAC CAGAATCCGT CCCCGCCATG GTCTAAACTG ACGTATTCCA AACCGCATGA
TTGCCGTTTG GTCTTAGGCA GGGGCGGTAC CAGATTTGAC TGCATAAGGT TTGGCGTACT

     13270      13280      13290      13300      13310      13320
CGCGGCGACG TTTTACTGTC CTTTTCTCTA TCCCTCGCCC CCACGGTCCC CCTTGCAATT
GCGCCGCTGC AAAATGACAG GAAAAGAGAT AGGGAGCGGG GGTGCCAGGG GGAACGTTAA

     13330      13340      13350      13360      13370      13380
CTCGGGGTTC CAGCAGGTAT CAACGGGTCC CGAGTGTCGC AACGAGACCC TGTATCTGCT
GAGCCCCAAG GTCGTCCATA GTTGCCCAGG GCTCACAGCG TTGCTCTGGG ACATAGACGA

     13390      13400      13410      13420      13430      13440
GTACAACCGG GAAGGCCAGA CCTTGGTGGA GAGAAGCTCC ACCTGGGTGA AAAAGGTGAT
CATGTTGGCC CTTCCGGTCT GGAACCACCT CTCTTCGAGG TGGACCCACT TTTTCCACTA

     13450      13460      13470      13480      13490      13500
CTGGTATCTG AGCGGTCGCA ACCAGACCAT CCTCCAACGG ATGCCCCAAA CGGCTTCGAA
GACCATAGAC TCGCCAGCGT TGGTCTGGTA GGAGGTTGCC TACGGGGTTT GCCGAAGCTT

     13510      13520      13530      13540      13550      13560
ACCGAGCGAC GGAAACGTGC AGATCAGCGT GGAAGACGCC AAGATTTTTG GAGCGCACAT
TGGCTCGCTG CCTTTGCACG TCTAGTCGCA CCTTCTGCGG TTCTAAAAAC CTCGCGTGTA

     13570      13580      13590      13600      13610      13620
GGTGCCCAAG CAGACCAAGC TGCTACGCTT CGTCGTCAAC GATGGCACGC GTTATCAGAT
CCACGGGTTC GTCTGGTTCG ACGATGCGAA GCAGCAGTTG CTACCGTGCG CAATAGTCTA

     13630      13640      13650      13660      13670      13680
GTGTGTGATG AAGCTGGAGA GCTGGGCCCA CGTCTTCCGG GACTACAGCG TGTCTTTTCA
CACACACTAC TTCGACCTCT CGACCCGGGT GCAGAAGGCC CTGATGTCGC ACAGAAAAGT
```

FIG._10-1

```
      13690      13700      13710      13720      13730      13740
GGTGCGATTG ACGTTCACCG AGGCCAATAA CCAGACTTAC ACCTTCTGTA CCCATCCCAA
CCACGCTAAC TGCAAGTGGC TCCGGTTATT GGTCTGAATG TGGAAGACAT GGGTAGGGTT

      13750 UL130 13760  13770      13780      13790      13800
TCTCATCATT TGAGCCCGTC GCGCGCGCAG GGAATTTTGA AAACCGCGCG TCATGAGTCC
AGAGTAGTAA ACTCGGGCAG CGCGCGCGTC CCTTAAAACT TTTGGCGCGC AGTACTCAGG

      13810      13820      13830      13840      13850      13860
CAAAGACCTG ACGCCGTTCT TGACGACGTT GTGGCTGCTA TTGGGTCACA GCCGCGTGCC
GTTTCTGGAC TGCGGCAAGA ACTGCTGCAA CACCGACGAT AACCCAGTGT CGGCGCACGG

      13870      13880      13890      13900      13910      13920
GCGGGTGCGC GCAGAAGAAT GTTGCGAATT CATAAACGTC AACCACCCGC CGGAACGCTG
CGCCCACGCG CGTCTTCTTA CAACGCTTAA GTATTTGCAG TTGGTGGGCG GCCTTGCGAC

      13930      13940      13950      13960      13970      13980
TTACGATTTC AAAATGTGCA ATCGCTTCAC CGTCGCGTAC GTATTTTCAT GATTGTCTGC
AATGCTAAAG TTTTACACGT TAGCGAAGTG GCAGCGCATG CATAAAAGTA CTAACAGACG

      13990      14000      14010      14020      14030      14040
GTTCTGTGGT GCGTCTGGAT TTGTCTCTCG ACGTTTCTGA TAGCCATGTT CCATCGACGA
CAAGACACCA CGCAGACCTA AACAGAGAGC TGCAAAGACT ATCGGTACAA GGTAGCTGCT

      14050      14060      14070      14080      14090      14100
TCCTCGGGAA TGCCAGAGTA GATTTTCATG AATCCACAGG CTGCGGTGTC CGGACGGCGA
AGGAGCCCTT ACGGTCTCAT CTAAAAGTAC TTAGGTGTCC GACGCCACAG GCCTGCCGCT

      14110      14120      14130      14140      14150      14160
AGTCTGCTAC AGTCCCGAGA AAACGGCTGA GATTCGCGGG ATCGTCACCA CCATGACCCA
TCAGACGATG TCAGGGCTCT TTTGCCGACT CTAAGCGCCC TAGCAGTGGT GGTACTGGGT
```

FIG._10-2

```
     14170      14180      14190      14200      14210      14220
TTCATTGACA CGCCAGGTCG TACACAACAA ACTGACGAGC TGCAACTACA ATCCGTAAGT
AAGTAACTGT GCGGTCCAGC ATGTGTTGTT TGACTGCTCG ACGTTGATGT TAGGCATTCA

     14230      14240      14250      14260      14270      14280
CTCTTCCTCG AGGGCCTTAC AGCCTATGGG AGAGTAAGAC AGAGAGGGAC AAAACATCAT
GAGAAGGAGC TCCCGGAATG TCGGATACCC TCTCATTCTG TCTCTCCCTG TTTTGTAGTA

     14290      14300      14310      14320      14330      14340
TAAAAAAAAA AGTCTAATTT CACGTTTTGT ACCCCCCTTC CCCTCCGTGT TGTAGCCCAT
ATTTTTTTTT TCAGATTAAA GTGCAAAACA TGGGGGGAAG GGGAGGCACA ACATCGGGTA

     14350      14360      14370      14380      14390      14400
CGGCCGCGGC GATCTCCTAG TAACACTCGT CCGACACTTC CACCATCTCC AGCTCGGCCG
GCCGGCGCCG CTAGAGGATC ATTGTGAGCA GGCTGTGAAG GTGGTAGAGG TCGAGCCGGC

     14410      14420      14430      14440      14450      14460
GCGGTTCGGC ATCCTCTACC AGCGGCGTCG TCTCATCTTT GCCGCAGCAG CGGACGCACA
CGCCAAGCCG TAGGAGATGG TCGCCGCAGC AGAGTAGAAA CGGCGTCGTC GCCTGCGTGT

     14470      14480      14490      14500      14510      14520
CCTTCTCCAG GCAGAACGCC ACCAGCTGCC GCCGAACGTA CCACAGGTAC ACGTGCAGAC
GGAAGAGGTC CGTCTTGCGG TGGTCGACGG CGGCTTGCAT GGTGTCCATG TGCACGTCTG

     14530      14540      14550      14560      14570      14580
CTGCGAACAG GACTACGGAG GTCATGACCA CCACGACGCA CACGGGAATC CAGGGATCGA
GACGCTTGTC CTGATGCCTC CAGTACTGGT GGTGCTGCGT GTGCCCTTAG GTCCCTAGCT

     14590      14600      14610      14620      14630      14640
GATTGTTGCT GGAACTCATG GCTATCGCCA CCGACGTGCC CGCGTCTGTC TCACCGCCGC
CTAACAACGA CCTTGAGTAC CGATAGCGGT GGCTGCACGG GCGCAGACAG AGTGGCGGCG
```

FIG._1P-1

```
     14650      14660      14670      14680      14690      14700
TCGCCCGATG TCGCGCGGCT TGTTATACGC TAGCCCGTCG CCGCCTCGGG GCACGGTGCC
AGCGGGCTAC AGCGCGCCGA ACAATATGCG ATCGGGCAGC GGCGGAGCCC CGTGCCACGG

     14710      14720      14730      14740      14750      14760
CTCCTACCCA CGTAACTTCC TCCGTGACTT AAAGTCGCGT GTGGTAGATC TCCTGCTCCG
GAGGATGGGT GCATTGAAGG AGGCACTGAA TTTCAGCGCA CACCATCTAG AGGACGAGGC

     14770      14780      14790      14800      14810      14820
TGGACGAACC GTCCGGCAGG ATAGCGGTTA AGGATTCGGT GCTAAGGCCG TGTCGCCAAC
ACCTGCTTGG CAGGCCGTCC TATCGCCAAT TCCTAAGCCA CGATTCCGGC ACAGCGGTTG

     14830      14840      14850      14860      14870      14880
GTCGAATGCT ACGTTGCAAC AGCTTCGACG GACGGCCATC CCCTCTCTCA TCGCAATAAT
CAGCTTACGA TGCAACGTTG TCGAAGCTGC CTGCCGGTAG GGGAGAGAGT AGCGTTATTA

     14890      14900      14910      14920      14930      14940
AAAACACCAG CAGCGCGCAC GACGCGATCA CGGTGACACC CATGATTAGA CCCACGCAGA
TTTTGTGGTC GTCGCGCGTG CTGCGCTAGT GCCACTGTGG GTACTAATCT GGGTGCGTCT

     14950      14960      14970      14980      14990      15000
TAGCCAGCCC CGCTAGCGTA TCTAGCGCCA TCCCGTTCGC TCCCGTTGTC TCCTGAGCGA
ATCGGTCGGG GCGATCGCAT AGATCGCGGT AGGGCAAGCG AGGGCAACAG AGGACTCGCT

     15010      15020      15030      15040      15050      15060
AGCAACTTCT CGGTCCCCGT TTTCAACAGT TTTTGTTTCC TTCTCCGCGA CTAGATGTTA
TCGTTGAAGA GCCAGGGGCA AAAGTTGTCA AAAACAAAGG AAGAGGCGCT GATCTACAAT

     15070      15080      15090      15100      15110      15120
ACGCCCGCGG TCTTTCCGGC CGTGCTCTAC CTCCTGGCGC TTGTCGTCTG GGTTGAGATG
TGCGGGCGCC AGAAAGGCCG GCACGAGATG GAGGACCGCG AACAGCAGAC CCAACTCTAC
```

FIG._1P-2

```
      15130      15140      15150      15160      15170      15180
TTCTGCCTCG TCGCCGTAGC CGTCGTCGAG CGCGAGATCG CCTGGGCGCT GCTGCTGCGG
AAGACGGAGC AGCGGCATCG GCAGCAGCTC GCGCTCTAGC GGACCCGCGA CGACGACGCC

      15190      15200      15210      15220      15230      15240
ATGCTGGTCG TTGGCCTGAT GGTGGAAGTC GGCGCCGCCG CCGCTTGGAC CTTCGTGCGT
TACGACCAGC AACCGGACTA CCACCTTCAG CCGCGGCGGC GGCGAACCTG GAAGCACGCA

      15250      15260      15270      15280      15290      15300
TGTCTTGCCT ATCAGCGCTC CTTCCCCGTG CTTACGGCCT TCCCCTGAAA CCCACGTTAA
ACAGAACGGA TAGTCGCGAG GAAGGGGCAC GAATGCCGGA AGGGGACTTT GGGTGCAATT

      15310      15320      15330      15340      15350      15360
CCGACCGTCC CAAAAACGCC GGTGTTAACA CAGGAAAAAA AGAAACCACG CAGGAACCGC
GGCTGGCAGG GTTTTTGCGG CCACAATTGT GTCCTTTTTT TCTTTGGTGC GTCCTTGGCG

      15370      15380      15390      15400      15410      15420
GCAGGAACCA CGCGGAACAT GGGACACTAT CTGGAAATCC TGTTCAACGT CATCGTCTTC
CGTCCTTGGT GCGCCTTGTA CCCTGTGATA GACCTTTAGG ACAAGTTGCA GTAGCAGAAG

      15430      15440      15450      15460      15470      15480
ACTCTGCTGC TCGGCGTCAT GGTCAGTATC GTCGCTTGGT ACTTCACGTG AACCACCGTC
TGAGACGACG AGCCGCAGTA CCAGTCATAG CAGCGAACCA TGAAGTGCAC TTGGTGGCAG

      15490      15500      15510      15520      15530      15540
GTCCCGGTTT AAAAACCATC ATCGACGGCC GTTATAAAGC CACCCGGACA CGCGCCGCGG
CAGGGCCAAA TTTTTGGTAG TAGCTGCCGG CAATATTTCG GTGGGCCTGT GCGCGGCGCC

      15550      15560      15570      15580      15590      15600
CACTTGCCTA CGGCGCTGCT TCAGGGAAAC TCCTCTTCCT TCTGCTCTTC CTCCTTCACC
GTGAACGGAT GCCGCGACGA AGTCCCTTTG AGGAGAAGGA AGACGAGAAG GAGGAAGTGG
```

FIG._1Q-1

```
     15610      15620      15630      15640      15650      15660
GCAGGGATCG TTTCCCTCGA CCAGGGACTC GCCGAAGCAA CCGCCGGAGC AACCTGGAGG
CGTCCCTAGC AAAGGGAGCT GGTCCCTGAG CGGCTTCGTT GGCGGCCTCG TTGGACCTCC

     15670      15680      15690      15700      15710      15720
AGTCGCGGCA TGACGGCGCC CAAGTGTGTC ACCACCAGTA CTTATCTGGT CAAGACCAAG
TCAGCGCCGT ACTGCCGCGG GTTCACACAG TGGTGGTCAT GAATAGACCA GTTCTGGTTC

     15730      15740      15750      15760 UL149 15770      15780
GAACAGCCCT GGTGGCCCGA CAACGCCATC AGGAGATGGT GGATCAGTGT TGCTATCGTC
CTTGTCGGGA CCACCGGGCT GTTGCGGTAG TCCTCTACCA CCTAGTCACA ACGATAGCAG

     15790      15800      15810      15820      15830      15840
ATCTTCATCG GAGTCTGTCT GGTGGCCCTG ATGTACTTTA CGCAGCAGCA GGCACGCAGC
TAGAAGTAGC CTCAGACAGA CCACCGGGAC TACATGAAAT GCGTCGTCGT CCGTGCGTCG

     15850      15860      15870 UL150 15880      15890      15900
GGGAGCAGCA GCGGCTAGAC AAGTCTCTGG CGGCTACAGC TCCAAGCGCC GTAGCCGGGC
CCCTCGTCGT CGCCGATCTG TTCAGAGACC GCCGATGTCG AGGTTCGCGG CATCGGCCCG

     15910      15920      15930      15940      15950      15960
CGCCTGCCGA TCGCGACGTC GTGGACCATC GAACAGAGAC TCACGCGTAC GAGACCCCGA
GCGGACGGCT AGCGCTGCAG CACCTGGTAG CTTGTCTCTG AGTGCGCATG CTCTGGGGCT

     15970      15980      15990      16000      16010      16020
GGTACGCCAC GCGGTGCCTA ACGCGGTATA CCACACCCGT ACGGTCTGCA GTGCGGCGTA
CCATGCGGTG CGCCACGGAT TGCGCCATAT GGTGTGGGCA TGCCAGACGT CACGCCGCAT

     16030      16040      16050      16060      16070      16080
CAACGTGTGG AAAACGCGTT GCGTCGCAGA GTCCGCCACG TTCCTGTCTT GTCGCTCCCC
GTTGCACACC TTTTGCGCAA CGCAGCGTCT CAGGCGGTGC AAGGACAGAA CAGCGAGGGG
```

FIG._1Q-2

```
                                                UL149
     16090      16100      16110      16120      16130      16140
AATCGTCTCC CGCACACCCC CCGCGACACC CAGAGGGCGG GTGAGCCAAG TATTCTTAAG
TTAGCAGAGG GCGTGTGGGG GGCGCTGTGG GTCTCCCGCC CACTCGGTTC ATAAGAATTC

     16150      16160      16170      16180      16190      16200
GCCGTTCTTT GTTCCATAGC CCATAAATTG TTGATTCCGG AGCTCGTTGG CGCGGAAATA
CGGCAAGAAA CAAGGTATCG GGTATTTAAC AACTAAGGCC TCGAGCAACC GCGCCTTTAT

     16210      16220      16230      16240      16250      16260
GCCGGATAAG GGGAGCAACA ACCGTTGGCG AAAGCCGTCC CGCTCATTCA GTCCGGGTTT
CGGCCTATTC CCCTCGTTGT TGGCAACCGC TTTCGGCAGG GCGAGTAAGT CAGGCCCAAA

     16270      16280      16290      16300      16310      16320
CGCGTCCAGT CGGACGTGTG ACCGTTGGGC AACGGAACGG CGTTTCACTG CCAAAATCGT
GCGCAGGTCA GCCTGCACAC TGGCAACCCG TTGCCTTGCC GCAAAGTGAC GGTTTTAGCA

     16330      16340      16350      16360      16370      16380
ATCGGGTAGT GTACGAGACG TCGGCGGTGC AGAATGCGAC TCGCGGCGTA GCTCGCCGTC
TAGCCCATCA CATGCTCTGC AGCCGCCACG TCTTACGCTG AGCGCCGCAT CGAGCGGCAG

     16390      16400      16410      16420      16430      16440
GCTATGCGGC TCGTCGCCGT GTGGCGCGGC CTGGCCGGCT GTCTGCGTCC AGATCTGTTG
CGATACGCCG AGCAGCGGCA CACCGCGCCG GACCGGCCGA CAGACGCAGG TCTAGACAAC

     16450      16460      16470      16480      16490      16500
GCCTTTTGGT TCCTCTGGCT GCTGCTGCGT GTGTGCTTTG GTAGACGCGG TGGCAGTTTG
CGGAAAACCA AGGAGACCGA CGACGACGCA CACACGAAAC CATCTGCGCC ACCGTCAAAC

     16510      16520      16530      16540      16550      16560
CGGTCTGCGG TAAGTGAGGA TGTCGCCGAG CAAACGCACT TGCGGCGCGT GGGCGGCACG
GCCAGACGCC ATTCACTCCT ACAGCGGCTC GTTTGCGTGA ACGCCGCGCA CCCGCCGTGC
```

FIG._1R-1

```
     16570      16580      16590      16600      16610      16620
CGTGTCATTG TAGGTTCGTT GCCAGATGGC AAGTGCTGTC AACAGCAGGC GTTGTGGGCG
GCACAGTAAC ATCCAAGCAA CGGTCTACCG TTCACGACAG TTGTCGTCCG CAACACCCGC

     16630      16640      16650      16660      16670      16680
GTCGGTGTAT TTTTGTGGGT TGCGGTGAGA GTCGGCACTC GGTGTTTTGT GAGTCATCTC
CAGCCACATA AAAACACCCA ACGCCACTCT CAGCCGTGAG CCACAAAACA CTCAGTAGAG

     16690      16700      16710      16720      16730      16740
AACTATCTGT GTTGCTTTGA GCAGCGTCCA GAACAGCGAC GCGACTTTGG GGATGGCCTC
TTGATAGACA CAACGAAACT CGTCGCAGGT CTTGTCGCTG CGCTGAAACC CCTACCGGAG

     16750      16760      16770      16780      16790      16800
GTGCTCACCT CCGCGGAGAG CGCCGCCGGA CCTGCTCGTC AGCAGCGAGC TACGCAGACG
CACGAGTGGA GGCGCCTCTC GCGGCGGCCT GGACGAGCAG TCGTCGCTCG ATGCGTCTGC

     16810      16820      16830      16840      16850      16860
GAATATCTGG AGGAGAGTTA CGTGTGTCAC AGGAGAGCGC GGGTCTCCGG CGGTAACGAC
CTTATAGACC TCCTCTCAAT GCACACAGTG TCCTCTCGCG CCCAGAGGCC GCCATTGCTG

     16870      16880      16890      16900      16910      16920
GGCGGTGTCG TCGACACGTG TGCGGCCTGT TGTGCTCTGC GGAAAAGTGC CGGTCTCGGA
CCGCCACAGC AGCTGTGCAC ACGCCGGACA ACACGAGACG CCTTTTCACG GCCAGAGCCT

     16930      16940      16950      16960      16970      16980
GACCGTGGAC GAAAAAGAGA ACGCAGCAGC TACCGCTGGC GGCGGCGGCG TTAATGCAGC
CTGGCACCTG CTTTTTCTCT TGCGTCGTCG ATGGCGACCG CCGCCGCCGC AATTACGTCG
```

FIG._1R-2

```
     16990      17000      17010      17020      17030      17040
CGTTGATGTT CGACGTTGTG AGCACTCGGA AACAGCGGTG AGGCAGAAGG TCGATTCTCC
GCAACTACAA GCTGCAACAC TCGTGAGCCT TTGTCGCCAC TCCGTCTTCC AGCTAAGAGG

     17050      17060      17070      17080      17090      17100
AGGGAACGAC AGTCGATGCG TGGTAGCCGC AGCAGGTGAG GTTGGGGCGG ACAACGTGTT
TCCCTTGCTG TCAGCTACGC ACCATCGGCG TCGTCCACTC CAACCCCGCC TGTTGCACAA

     17110      17120      17130      17140      17150      17160
GCGGATTGTG GCGAGAACGT CGTCCTCCCC TTCTTCACCG CCCCACCCAC CCTCGGTTGG
CGCCTAACAC CGCTCTTGCA GCAGGAGGGG AAGAAGTGGC GGGGTGGGTG GGAGCCAACC

     17170      17180      17190      17200      17210      17220
TGTTTCTTTT TTCTTGTGTC CTGCAGATAG TTCCACGGAC AGCGACGGCA AGTCCATAAT
ACAAAGAAAA AAGAACACAG GACGTCTATC AAGGTGCCTG TCGCTGCCGT TCAGGTATTA

     17230      17240      17250      17260      17270      17280
CAGCGGTGTG CAAGTGGTGG AACACGACGA AGATATCATC GCGCCGCAGA GTTTGTGGTG
GTCGCCACAC GTTCACCACC TTGTGCTGCT TCTATAGTAG CGCGGCGTCT CAAACACCAC

     17290 UL151 17300      17310      17320      17330      17340
CACGGCGTTC AAGGAAGCCC TCTGGGATGT GGCTCTGTTG GAAGTGCCGC GTTGGGCGTG
GTGCCGCAAG TTCCTTCGGG AGACCCTACA CCGAGACAAC CTTCACGGCG CAACCCGCAC

     17350      17360      17370      17380      17390      17400
GCAGGGCTGG AAGAGGTGGC GCAACAGCGA GGCCGGGCGT CGATGGAGTG CTGGGTCTGC
CGTCCCGACC TTCTCCACCG CGTTGTCGCT CCGGCCCGCA GCTACCTCAC GACCCAGACG

     17410      17420      17430      17440      17450      17460
GTCGGCTTCC AGCTTGTCTG ACTTGGCGGG CGAGGCCGTT GGAGAATTGG TGGGATCGGT
CAGCCGAAGG TCGAACAGAC TGAACCGCCC GCTCCGGCAA CCTCTTAACC ACCCTAGCCA
```

FIG._1S-1

```
     17470      17480      17490      17500      17510      17520
CGTCGCGTAC GTGATCCTTG AACGTCTGTG GTTGGCAGCC AGAGGTTGGG TGTGCGAAAC
GCAGCGCATG CACTAGGAAC TTGCAGACAC CAACCGTCGG TCTCCAACCC ACACGCTTTG

     17530      17540      17550      17560      17570      17580
AGGTGTGGAA GCCGAGGAGG CCATGTCGCG GCGGCGACAG CGCATGCTGT GGCGTATTGT
TCCACACCTT CGGCTCCTCC GGTACAGCGC CGCCGCTGTC GCGTACGACA CCGCATAACA

     17590      17600      17610      17620      17630      17640
TCTCTCGTGG AGGCGACGGC GAATGCAGCA GACGGTGTTC GATGGAGATG GCGTGCGGGG
AGAGAGCACC TCCGCTGCCG CTTACGTCGT CTGCCACAAG CTACCTCTAC CGCACGCCCC

     17650      17660      17670      17680      17690      17700
AAGAAAGCGC CGTGTTGTGA GCAGACGACG TAGGATGCGG GACGTCGGAG CACATGGGCC
TTCTTTCGCG GCACAACACT CGTCTGCTGC ATCCTACGCC CTGCAGCCTC GTGTACCCGG

     17710      17720      17730      17740      17750      17760
ATGTGTGGTG GCAGATGGCG GTGTCCGCTG GTGTCTGCTG CGGCAGTGCA TAGACGAAGC
TACACACCAC CGTCTACCGC CACAGGCGAC CACAGACGAC GCCGTCACGT ATCTGCTTCG

                                           UL150
     17770      17780      17790      17800      17810      17820
AACATGTCGC TGTGAAGAGA TAGAGTGTGA GCATAGCTGC ATGCAGCGTT GCGTGTATAA
TTGTACAGCG ACACTTCTCT ATCTCACACT CGTATCGACG TACGTCGCAA CGCACATATT

     17830      17840      17850      17860      17870      17880
GCGGSGGGGA TTAAGACGTT AATAAAGAAT AGCGGCGGTT CTGATAGGGC GACCGCTGAA
CGCCCCCCCT AATTCTGCAA TTATTTCTTA TCGCCGCCAA GACTATCCCG CTGGCGACTT

     17890      17900      17910      17920      17930      17940
GTGAGCTGCG TGTGCGTGTG GTTTGTGGAG TCCCCGCCGC CCCCGGTCCC GTGTCCGCCG
CACTCGACGC ACACGCACAC CAAACACCTC AGGGGCGGCG GGGGCCAGGG CACAGGCGGC
```

FIG._1S-2

```
      17950      17960      17970      17980      17990      18000
GCAAAGCCCC CCGGNTCCGC ACACTCCTGG CCGCGCAACC CTCGTCGCTG CAAAAGCCCC
CGTTTCGGGG GGCCNAGGCG TGTGAGGACC GGCGCGTTGG GAGCAGCGAC GTTTTCGGGG

      18010      18020      18030      18040      18050      18060
CCGTCCCCGC ACACCCCCGC GACCGCCGGT CCCGCGAGTC CCCGTCCCCG CCGCAAAAGG
GGCAGGGGCG TGTGGGGGCG CTGGCGGCCA GGGCGCTCAG GGGCAGGGGC GGCGTTTTCC

      18070      18080      18090      18100      18110      18120
CCCCCGTCCT CGCCGCAAAC ACCCCCGTCA CCCCCGTCCC TCAGNCCGGG TCCGCGAGTC
GGGGGCAGGA GCGGCGTTTG TGGGGGCAGT GGGGGCAGGG AGTCNGGCCC AGGCGCTCAG

      18130      18140      18150      18160      18170      18180
CCCGTTCCCA GCGTAATCCC CGTACCCGCA ACGNCCCGGN CCCACCGTCG TCCCGCACAC
GGGCAAGGGT CGCATTAGGG GCATGGGCGT TGCNGGGCCN GGGTGGCAGC AGGGCGTGTG

      18190      18200      18210      18220      18230      18240
CCCCCGTCCC CCAGCCCGGT GCCCAGCGTG CGAAAAAAGC TCCGTCCCTC ACACCCGCAG
GGGGGCAGGG GGTCGGGCCA CGGGTCGCAC GCTTTTTTCG AGGCAGGGAG TGTGGGCGTC

      18250      18260      18270      18280      18290      18300
AAAGATCCCT CAGCGCGGTG AAACCCCGTC CCCAGCGCCG TGCCGCTGAC AAAGACCATG
TTTCTAGGGA GTCGCGCCAC TTTGGGGCAG GGGTCGCGGC ACGGCGACTG TTTCTGGTAC
                                                       UL151
      18310      18320      18330      18340      18350      18360
GGACGACACG CACAGGCA.. .......... .......... .......... ..........
CCTGCTGTGC GTGTCCGT.. .......... .......... .......... ..........
```

FIG._1T

```
        10         20         30         40         50         60
ATCGGGCGCC AGAGCTAGAT CAGGCGTATC AAATTCCACT GCCAGGCGAC CTGATTCTAA
TAGCCCGCGG TCTCGATCTA GTCCGCATAG TTTAAGGTGA CGGTCCGCTG GACTAAGATT

        70         80         90        100        110        120
CGGTTCCACG ATCCGGGAGA GCGTTTCTAG ATATAGAGCA AAGCGTACCA CGTCTACCTG
GCCAAGGTGC TAGGCCCTCT CGCAAAGATC TATATCTCGT TTCGCATGGT GCAGATGGAC

       130        140        150        160        170        180
CGGTGTAAAA AACTGTTGTG GGCGTTCACC GTCGTTGACC ACGTAAGCCA CGTAGAGGCC
GCCACATTTT TTGACAACAC CCGCAAGTGG CAGCAACTGG TGCATTCGGT GCATCTCCGG

       190        200        210        220        230        240
AACATTTTCC ACCACGGGTT CTAGCTGCAG GCGGCACGTA AAGCTTAGAA ACGACGGCTG
TTGTAAAAGG TGGTGCCCAA GATCGACGTC CGCCGTGCAT TTCGAATCTT TGCTGCCGAC

       250        260        270        280        290        300
TACGGTTTGG TTCCCGTGAA GCTGAAGCGT CACTTCCTTG CCGGGGCTCA CCGTGCTGTA
ATGCCAAACC AAGGGCACTT CGACTTCGCA GTGAAGGAAC GGCCCCGAGT GGCACGACAT

       310        320        330        340        350        360
ACGCCGCACC GAGTCGGTCA TCTGCTCCAG ATCGGTAGAC CAGAAGGGCG TGCAATGCAT
TGCGGCGTGG CTCAGCCAGT AGACGAGGTC TAGCCATCTG GTCTTCCCGC ACGTTACGTA

       370        380        390        400        410        420
ACTGTCCCAG TCGCGACACG CAGCCCAGCC TAGCTCGGTG AAGGGTCGAC GCACACCCGA
TGACAGGGTC AGCGCTGTGC GTCGGGTCGG ATCGAGCCAC TTCCCAGCTG CGTGTGGGCT

       430        440        450        460        470        480
AAAAGTGTGC TTGAAGACCA GGGGGTCGCC TCGGTAGCTC AGTAGCCGAA CATGCACATA
TTTTCACACG AACTTCTGGT CCCCCAGCGG AGCCATCGAG TCATCGGCTT GTACGTGTAT
```

FIG._2A-1

```
       490        500        510        520        530        540
GTCGCGGCTA CGTTGACAGA CGGCCCGTAG ACAGGCAGGA CAAGCGTGAA CAGCAAGCGC
CAGCGCCGAT GCAACTGTCT GCCGGGCATC TGTCCGTCCT GTTCGCACTT GTCGTTCGCG

       550        560        570        580        590        600
AACATGCTGC GGGTTAGAAA ATGCGGCGTG CCGGCCACCG CCCGACTCAT AAACGCTACC
TTGTACGACG CCCAATCTTT TACGCCGCAC GGCCGGTGGC GGGCTGAGTA TTTGCGATGG

       610        620        630        640        650        660
AGCATGACGT CTCAGATCAC ACAAGTGACG AGGAGCGTAC CGCAAATCAC TAGGGAAAAG
TCGTACTGCA GAGTCTAGTG TGTTCACTGC TCCTCGCATG GCGTTTAGTG ATCCCTTTTC

       670        680        690        700        710        720
GCCAGCAGAG CCCGATAGTC TTGCTCTTCG CGAACGATCT CGTCCGGTTC CTCGCAGTCT
CGGTCGTCTC GGGCTATCAG AACGAGAAGC GCTTGCTAGA GCAGGCCAAG GAGCGTCAGA

       730        740        750        760        770        780
TCGTGGTCCA CAGAAGATGA GGAGCAGGAT TCTTCGTTAA TTTCTGCCAG GATACTAGTG
AGCACCAGGT GTCTTCTACT CCTCGTCCTA AGAAGCAATT AAAGACGGTC CTATGATCAC

       790        800        810        820        830        840
CTGTACCACA CCAGAGCGCT CAGCGTGCCC AGGGCTACCG CACGGTAAAA TAGGGACATG
GACATGGTGT GGTCTCGCGA GTCGCACGGG TCCCGATGGC GTGCCATTTT ATCCCTGTAC

 UL147 850        860        870        880        890        900
ATCACCAGCG CAATCTGAAG TGGTGGTAGT TCAGTTTCTT GGCGTATTTC CAGAGAAAGG
TAGTGGTCGC GTTAGACTTC ACCACCATCA AGTCAAAGAA CCGCATAAAG GTCTCTTTCC

       910        920        930        940        950        960
CTTTGTAGGC CGTAGGGACT GGCCAGGCAC CGAACTCAAT ATTGGTAGAC ACTACGTCGT
GAAACATCCG GCATCCCTGA CCGGTCCGTG GCTTGAGTTA TAACCATCTG TGATGCAGCA
```

FIG._2A-2

```
        970        980        990       1000       1010       1020
 AAATGCGTTG TTCCTCGTCT AAGATTAACC GAAAAAATAG CCGGTTGATG TGACGACGCA
 TTTACGCAAC AAGGAGCAGA TTCTAATTGG CTTTTTTATC GGCCAACTAC ACTGCTGCGT

       1030       1040       1050       1060       1070       1080
 CGGCTTGCGC GTTAGGATTG AGACACTTGG TGCCCTTGTC CTTTAAAATA GCCAGCACTT
 GCCGAACGCG CAATCCTAAC TCTGTGAACC ACGGGAACAG GAAATTTTAT CGGTCGTGAA

       1090       1100       1110       1120       1130       1140
 CCTGACGATT GCAGCTTTCG CTCGCCGCGA TTGGCTTAAG CAATTCAGTT CCGATTGGCA
 GGACTGCTAA CGTCGAAAGC GAGCGGCGCT AACCGAATTC GTTAAGTCAA GGCTAACCGT

       1150       1160       1170       1180       1190       1200
 GAGTATTCAA CAGAATTTGG TTGTTACAAC GACAGCGTTT GTCGTAATCT TCCAATTCTA
 CTCATAAGTT GTCTTAAACC AACAATGTTG CTGTCGCAAA CAGCATTAGA AGGTTAAGAT

       1210       1220       1230       1240       1250       1260
 AAAGATGGAC GGCTAGGGGA CATACGACAA ATAACATGTA TGCAGTCAAT TGCATATATC
 TTTCTACCTG CCGATCCCCT GTATGCTGTT TATTGTACAT ACGTCAGTTA ACGTATATAG

       1270       1280       1290       1300       1310       1320
 GTACCGATAA AATGTTAGTG TGCGGATTCA GAATCGGATG ATGCAACCGT CTTAGCATCA
 CATGGCTATT TTACAATCAC ACGCCTAAGT CTTAGCCTAC TACGTTGGCA GAATCGTAGT

UL147  1330       1340       1350       1360       1370       1380
 TATCGAAAAA GTATACATAT TACCGATTCA TTATAATTAG GGAATTATTT CCAACGCGGA
 ATAGCTTTTT CATATGTATA ATGGCTAAGT AATATTAATC CCTTAATAAA GGTTGCGCCT
                                                UL152
       1390       1400       1410       1420       1430       1440
 CGTTTGTTAG TGACAGCGTT TTCTTCTACA TGCGGTCCAT TACTATCCTT TACTTTTACC
 GCAAACAATC ACTGTCGCAA AAGAAGATGT ACGCCAGGTA ATGATAGGAA ATGAAAATGG
```

FIG._2B-1

```
      1450       1460       1470       1480       1490       1500
AATACTCTGT GCCATGAGTT GTCTTTTTTA CCATCCAGCC ATTTGGACAA ATGATGATCG
TTATGAGACA CGGTACTCAA CAGAAAAAAT GGTAGGTCGG TAAACCTGTT TACTACTAGC

      1510       1520       1530       1540       1550       1560
GGAGCTAAAC ATACAGGTTT ACCTCGAGGA GGCAATAGAT AATGTTGAGG TTTGTCACAC
CCTCGATTTG TATGTCCAAA TGGAGCTCCT CCGTTATCTA TTACAACTCC AAACAGTGTG

      1570       1580       1590       1600       1610       1620
TCAGGAGGAT TGGGAGGGTC ACGACCAACC CAAAATAAGC CACCTATAGG ATGATGTAAA
AGTCCTCCTA ACCCTCCCAG TGCTGGTTGG GTTTTATTCG GTGGATATCC TACTACATTT

      1630       1640       1650       1660       1670       1680
GCTTTGTGGG TACACGGACA ACGCAATTCT CTACTGTGAA CCCCATGGTA ATACATAAAT
CGAAACACCC ATGTGCCTGT TGCGTTAAGA GATGACACTT GGGGTACCAT TATGTATTTA

                                            UL152
      1690       1700       1710       1720       1730       1740
GCCATCAAAA GACTAATCAG CGAACCAAAA ATTAATCGCA TTCTAATTTT ATTAACTACG
CGGTAGTTTT CTGATTAGTC GCTTGGTTTT TAATTAGCGT AAGATTAAAA TAATTGATGC

      1750       1760       1770       1780       1790       1800
TCACTATCAG TAATTCGTAA TATCCGGTAT TCCCGGAAAA TCACTCAAAA CTGCGTCCAT
AGTGATAGTC ATTAAGCATT ATAGGCCATA AGGGCCTTTT AGTGAGTTTT GACGCAGGTA

      1810       1820       1830       1840       1850       1860
GACACATCAA TTCCCGATAA GTACCCCCCT TTGAAATCGG ATCCCCCCAC ATACCAATCA
CTGTGTAGTT AAGGGCTATT CATGGGGGGA AACTTTAGCC TAGGGGGGTG TATGGTTAGT
```

FIG._2B-2

```
      1870       1880       1890       1900       1910       1920
ATCACACAAC ACACAGGTTT AAAAATCGAT CACACGTCAA TTAGGTTTCA AAATCGATAC
TAGTGTGTTG TGTGTCCAAA TTTTTAGCTA GTGTGCAGTT AATCCAAAGT TTTAGCTATG

      1930       1940       1950       1960       1970       1980
TGTTTATTAT CAGGAATCTA GACTAATTCT ACAATGACAG CTCTGAATTT CTCTCTCGTC
ACAAATAATA GTCCTTAGAT CTGATTAAGA TGTTACTGTC GAGACTTAAA GAGAGAGCAG

      1990       2000       2010       2020       2030       2040
TTTCTTGTCA GGTTCTCATC ATCAATCTTC ACTTCCACCC ATCGAGGAGT CATCGTCGCT
AAAGAACAGT CCAAGAGTAG TAGTTAGAAG TGAAGGTGGG TAGCTCCTCA GTAGCAGCGA

      2050       2060       2070       2080       2090       2100
CCAAAACCCT TTGGGGTCGC TGGTTGGAAA AGTCTCTGAC ACGATCCAGG CACCCCGTAC
GGTTTTGGGA AACCCCAGCG ACCAACCTTT TCAGAGACTG TGCTAGGTCC GTGGGGCATG

      2110       2120       2130       2140       2150       2160
CCAGTCCGAC TGATCTAGCT TACGGAGCAT CTCAACAGGC ATGAGCTGCA GGGCCACGGC
GGTCAGGCTG ACTAGATCGA ATGCCTCGTA GAGTTGTCCG TACTCGACGT CCCGGTGCCG

      2170       2180       2190       2200       2210       2220
TGTCACGGCA GGGATTATTA CTACCGTTCA GGTAAACTGT ATCTCCCTGA GTTACCGTGA
ACAGTGCCGT CCCTAATAAT GATGGCAAGT CCATTTGACA TAGAGGGACT CAATGGCACT

      2230       2240       2250       2260       2270       2280
TGGGTCTTTC TACATGTTGA CTTTGCGTAA AAAATCGCCG GTAAAATGTT TTTTCTTGTT
ACCCAGAAAG ATGTACAACT GAAACGCATT TTTTAGCGGC CATTTTACAA AAAAGAACAA

      2290       2300       2310       2320       2330       2340
CATGTAAAAG TACCGGAACT AAAATGCTAG TTAGAATGGT TGCAGTTGCT ATTAGCGCGG
GTACATTTTC ATGGCCTTGA TTTTACGATC AATCTTACCA ACGTCAACGA TAATCGCGCC
```

FIG._2C-1

```
      2350       2360       2370       2380       2390       2400
CTAGTAACAG TAGTTTAGTG TTACATTGTA TACCCATGTT TTTAATAACT ATGAATATTC
GATCATTGTC ATCAAATCAC AATGTAACAT ATGGGTACAA AAATTATTGA TACTTATAAG

      2410       2420       2430       2440       2450       2460
TGCTTCACAC CATAAGTGCT TAACCCACAA AAACCACACG GAGACATTAT TGGCTAARAA
ACGAAGTGTG GTATTCACGA ATTGGGTGTT TTTGGTGTGC CTCTGTAATA ACCGATTTTT

      2470       2480       2490       2500 UL153 2510       2520
TAAAAACAAA AGTTTATTGA TGTGCATGTT AGGTTTTAGT CTAAAATTCA TCTGGGTCGT
ATTTTTGTTT TCAAATAACT ACACGTACAA TCCAAAATCA GATTTTAAGT AGACCCAGCA

      2530       2540       2550       2560       2570       2580
ATTTGGGAAG TTTTGTATAA CGCGGTCTTC TGGGGACGCG ACGGCTACCC ATGTATAAGG
TAAACCCTTC AAAACATATT GCGCCAGAAG ACCCCTGCGC TGCCGATGGG TACATATTCC

      2590       2600       2610       2620       2630       2640
CTATAAGTGC CACAGATACC ACTATACCCG CCCATACAGC ATGAATTCCC AGGGGAATGT
GATATTCACG GTGTCTATGG TGATATGGGC GGGTATGTCG TACTTAAGGG TCCCCTTACA

      2650       2660       2670       2680       2690       2700
TAGTGTTTTT TACAGTTTTT ATTACATTGT CCCACGTTCT GCTATTATGC TGGTCTGATT
ATCACAAAAA ATGTCAAAAA TAATGTAACA GGGTGCAAGA CGATAATACG ACCAGACTAA

      2710       2720       2730       2740       2750       2760
CCTCTTTTGT TTTACATTTA TCAGGTATAG GAGACGATGT TGCAGTTCCT GATAACACGG
GGAGAAAACA AAATGTAAAT AGTCCATATC CTCTGCTACA ACGTCAAGGA CTATTGTGCC

      2770       2780       2790       2800       2810       2820
TTAAATAGTA GTTTTCCTTT TTACCGTCAC TGTAACGTTG CAAAACGTAT TTTCCAGCGT
AATTTATCAT CAAAAGGAAA AATGGCAGTG ACATTGCAAC GTTTTGCATA AAAGGTCGCA
```

FIG._2C-2

```
      2830       2840       2850       2860       2870       2880
GTTCGGTAGT TACGTTGTAT ATAGTGAGAG AGGTCTTATT GCAGTCTAAA CACATGCCGT
CAAGCCATCA ATGCAACATA TATCACTCTC TCCAGAATAA CGTCAGATTT GTGTACGGCA

      2890       2900       2910       2920       2930       2940
TCAGTGGGGA AGTTGAATAA TAATGTCCAA TGCTGCACAG TTGGTGTGCG CGAGGTCCAT
AGTCACCCCT TCAACTTATT ATTACAGGTT ACGACGTGTC AACCACACGC GCTCCAGGTA

      2950       2960       2970       2980       2990       3000
ATTTTATCCA TTCTATATCG TGCCATACAT CCGTTCTACT GCAGTTTTTC AAAGTGACGT
TAAAATAGGT AAGATATAGC ACGGTATGTA GGCAAGATGA CGTCAAAAAG TTTCACTGCA

      3010       3020       3030       3040       3050       3060
ATCCACCGAC ATATCCTGTT ACATTAATTA CTTCGTAATT TAAATTAGAG TGTTTATAAA
TAGGTGGCTG TATAGGACAA TGTAATTAAT GAAGCATTAA ATTTAATCTC ACAAATATTT

      3070       3080       3090       3100       3110       3120
CGGTGTACAA ACTGCCATTG CAAGTTATGT TGCTGGTATT CAACCAGGGA GTAGTACTAT
GCCACATGTT TGACGGTAAC GTTCAATACA ACGACCATAA GTTGGTCCCT CATCATGATA

      3130       3140       3150       3160       3170       3180
GAATGGTAGA AAACGTTAAT GTTGGCGTAG CGCTTGACGA TGATTTTGAA AGCGTTGAAG
CTTACCATCT TTTGCAATTA CAACCGCATC GCGAACTGCT ACTAAAACTT TCGCAACTTC

      3190       3200       3210       3220       3230       3240
TGGTTGCTGA TGCGACTGAA GAAGCGGTAG AGGGTTTGTG CGTGGTTCCA TTTGCGATAG
ACCAACGACT ACGCTGACTT CTTCGCCATC TCCCAAACAC GCACCAAGGT AAACGCTATC

      3250       3260       3270       3280       3290       3300
CTGAAGTGCT GTTAGCATCG GTGACAGAGT TAGAAGAATT TGTGATAGTG GAGGCGGTGG
GACTTCACGA CAATCGTAGC CACTGTCTCA ATCTTCTTAA ACACTATCAC CTCCGCCACC
```

FIG._2D-1

```
                                      UL153
      3310       3320       3330       3340       3350       3360
AGGTAAAGGC AATTGCACGG ACAGGAGCAC GTGTCATTGC AACCTTCAGA TATCGTAATC
TCCATTTCCG TTAACGTGCC TGTCCTCGTG CACAGTAACG TTGGAAGTCT ATAGCATTAG

      3370       3380       3390       3400       3410       3420
ATCAGTAACG TCCACTTAAC CGTAAATCTC CAGTCCATAA CGTTATTAAA TTTCGGTTAA
TAGTCATTGC AGGTGAATTG GCATTTAGAG GTCAGGTATT GCAATAATTT AAAGCCAATT

      3430       3440       3450       3460       3470       3480
CGGGCATTGA TGTTTCTTCG GACGTTGTTG ATCTTTCTTG CCCGTTTATT TTCTGATATG
GCCCGTAACT ACAAAGAAGC CTGCAACAAC TAGAAAGAAC GGGCAAATAA AAGACTATAC

                                      UL154
      3490       3500       3510       3520       3530       3540
GTCTCATAAG ACATTTATCC GGAAACGTTG CTTAGTCCTC GTGCTCAGGA TTGTATCGAA
CAGAGTATTC TGTAAATAGG CCTTTGCAAC GAATCAGGAG CACGAGTCCT AACATAGCTT

      3550       3560       3570       3580       3590       3600
CTATGAATTC TGATTCACTT ATATCGTCAC TTAATGGATG ATATTTTTTA TTTAGAGCTC
GATACTTAAG ACTAAGTGAA TATAGCAGTG AATTACCTAC TATAAAAAAT AAATCTCGAG

      3610       3620       3630       3640       3650       3660
GTCGGACGAA AAATAGGAGA ATGCAGGCTA CACAAATTAA TGCTAACGTC CACGTAGTGC
CAGCCTGCTT TTTATCCTCT TACGTCCGAT GTGTTTAATT ACGATTGCAG GTGCATCACG

      3670       3680       3690       3700       3710       3720
GTCTGCCGTG TGATGTGTTA GAATGATTGT TATAGCGGTA TAAATGATCT ATAGATGATG
CAGACGGCAC ACTACACAAT CTTACTAACA ATATCGCCAT ATTTACTAGA TATCTACTAC

      3730       3740       3750       3760       3770       3780
TGGCTGTATT GTCTTCATAA TTGGTCGGTT TATGAGAAGT GTCCCATTCG TGCTTTGGTT
ACCGACATAA CAGAAGTATT AACCAGCCAA ATACTCTTCA CAGGGTAAGC ACGAAACCAA
```

FIG._2D-2

```
      3790       3800       3810       3820       3830       3840
CTTCACATAC CCAGGGATTC ACGTGTGTCC CGTTTGTGTT GTTTCTAGGA TGTATTTGCA
GAAGTGTATG GGTCCCTAAG TGCACACAGG GCAAACACAA CAAAGATCCT ACATAAACGT

      3850       3860       3870       3880       3890       3900
GATTARAGTT TTGATTTTGT TCGGAGGGAT GCCCAGTTTT ATAACATCGA AAGCTATATT
CTAATTTCAA AACTAAAACA AGCCTCCCTA CGGGTCAAAA TATTGTAGCT TTCGATATAA

      3910       3920       3930       3940       3950       3960
TACCAGAATG AGTAAAATTA AGACCGTACA GAGATAAAGA TAAATTACGA TCGCATGTAA
ATGGTCTTAC TCATTTTAAT TCTGGCATGT CTCTATTTCT ATTTAATGCT AGCGTACATT

      3970       3980       3990       4000       4010       4020
AACATAAATC ATAGTGATGT TTTAGATAAT TTGTGTGCCA CTCACATAGT ATACGCGAAT
TTGTATTTAG TATCACTACA AAATCTATTA AACACACGGT GAGTGTATCA TATGCGCTTA

      4030       4040       4050       4060       4070       4080
GGAGGATTTT CAATGAATGG TTATGATATT TTCCATTTCT TATGTTGGGA TGGGTGTATT
CCTCCTAAAA GTTACTTACC AATACTATAA AAGGTAAAGA ATACAACCCT ACCCACATAA

      4090       4100       4110       4120       4130       4140
TTCCGTGTGT GGATATATTA AAATGTCTAA GCCAGGCTGT TTTGTAGCAC GATGTGATGG
AAGGCACACA CCTATATAAT TTTACAGATT CGGTCCGACA AAACATCGTG CTACACTACC

      4150       4160       4170       4180       4190       4200
TTAGGTTGTG TGTTATAGTA ATATTGTCTC CTTGTGCCGC CTCCAATAAT GTTTCAGATT
AATCCAACAC ACAATATCAT TATAACAGAG GAACACGGCG GAGGTTATTA CAAAGTCTAA

      4210       4220       4230       4240       4250       4260
CTTTTGATAT CGTATTATTT GTACTGTTAG GCGATGAGCA AGTTGGAAGC GGTGTAGTGA
GAAAACTATA GCATAATAAA CATGACAATC CGCTACTCGT TCAACCTTCG CCACATCACT
```

FIG._2E-1

```
      4270       4280       4290       4300       4310       4320
CGTTTTCATT TGCATTTATC ATAGTAGTAG TGTTGGTTGA TAATGATATA GTTTGCAAAG
GCAAAAGTAA ACGTAAATAG TATCATCATC ACAACCAACT ATTACTATAT CAAACGTTTC

      4330       4340       4350       4360       4370       4380
TCACAGTACT ATCGGTTACA TGCTGTGTCG ATGAATTCGT GTCGCCGTTT GGTGAAGTTG
AGTGTCATGA TAGCCAATGT ACGACACAGC TACTTAAGCA CAGCGGCAAA CCACTTCAAC

      4390       4400       4410       4420       4430       4440
TTATTACAGT TACGTTAGTT GTAGATGTTT GGGTAGATAT GGTGGAAATA GTTGAGGTCA
AATAATGTCA ATGCAATCAA CATCTACAAA CCCATCTATA CCACCTTTAT CAACTCCAGT

      4450       4460       4470       4480       4490       4500
CGTCTGTGCC TTTTACAGAG CTTGCAGTGA ATCCTGTGGA TGTGTTGACG TTGCCATTGG
GCAGACACGG AAAATGTCTC GAACGTCACT TAGGACACCT ACACAACTGC AACGGTAACC

      4510       4520       4530       4540       4550       4560
AGGATGTGAA CATAGTGGTA GACATTTCGG TGGTTTGTAA CGTAGATGTC AGTTGTGTAG
TCCTACACTT GTATCACCAT CTGTAAAGCC ACCAAACATT GCATCTACAG TCAACACATC

      4570       4580       4590       4600       4610       4620
TAGATATTAA GCTTGTGGGT GTAATCGACG TGGAAGTATT GGCGATAGTG GTGTTGTTAC
ATCTATAATT CGAACACCCA CATTAGCTGC ACCTTCATAA CCGCTATCAC CACAACAATG

      4630       4640       4650       4660       4670       4680
ACTTGCTTTT CTGCAGAATC CAAAAAATAA TAAACATGCA TATTATTTGC GTATATGATG
TGAACGAAAA GACGTCTTAG GTTTTTTATT ATTTGTACGT ATAATAAACG CATATACTAC

      4690       4700       4710       4720       4730       4740
ACTTGTTCCA CCGTCGATGT TGTGTGCGCA T......... .......... ..........
TGAACAAGGT GGCAGCTACA ACACACGCGT A......... .......... ..........
                                 <-- UL154
```

FIG._2E-2

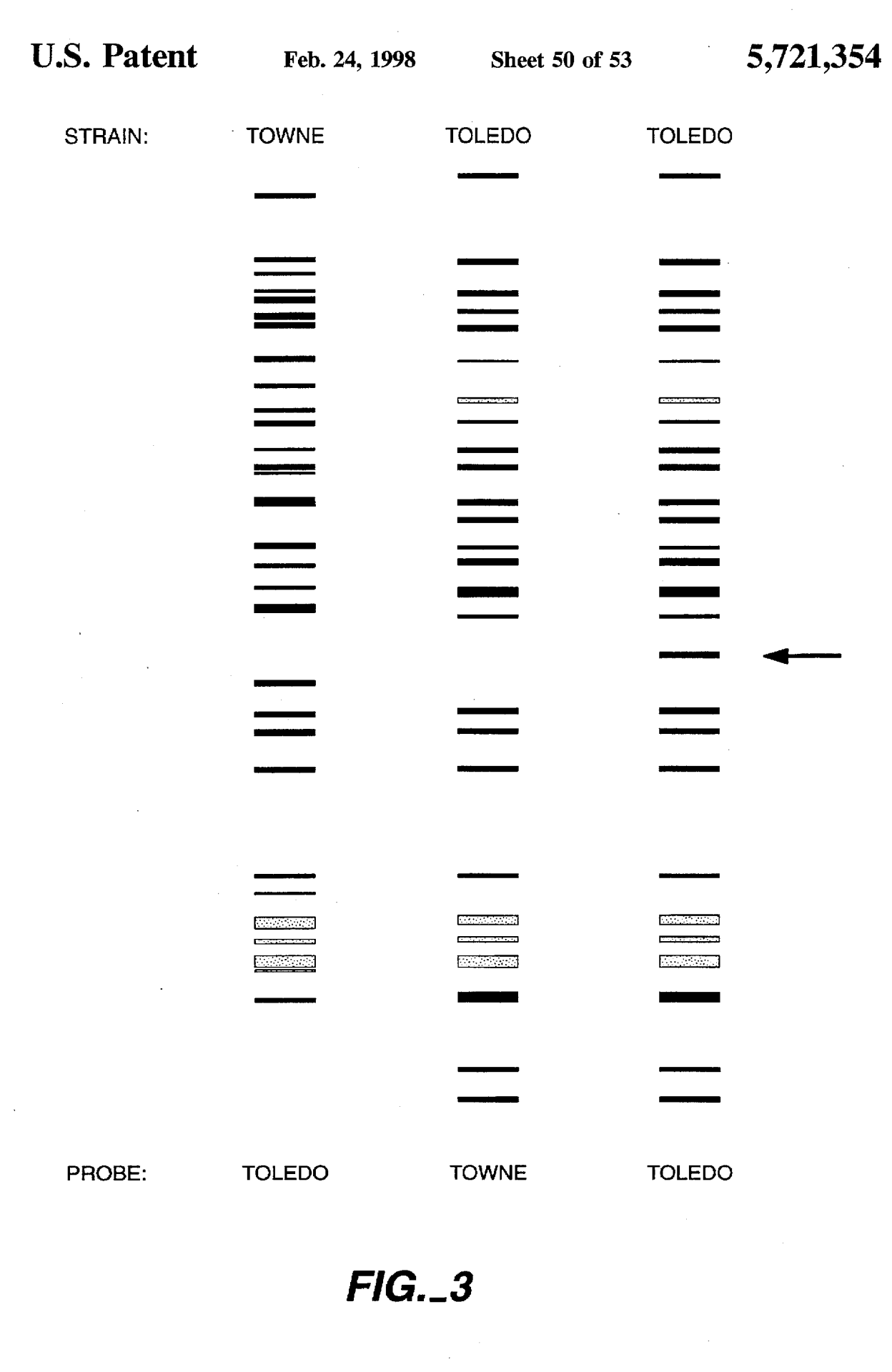

STRAIN: TOWNE TOLEDO TOLEDO

PROBE: TOLEDO TOWNE TOLEDO

FIG._3

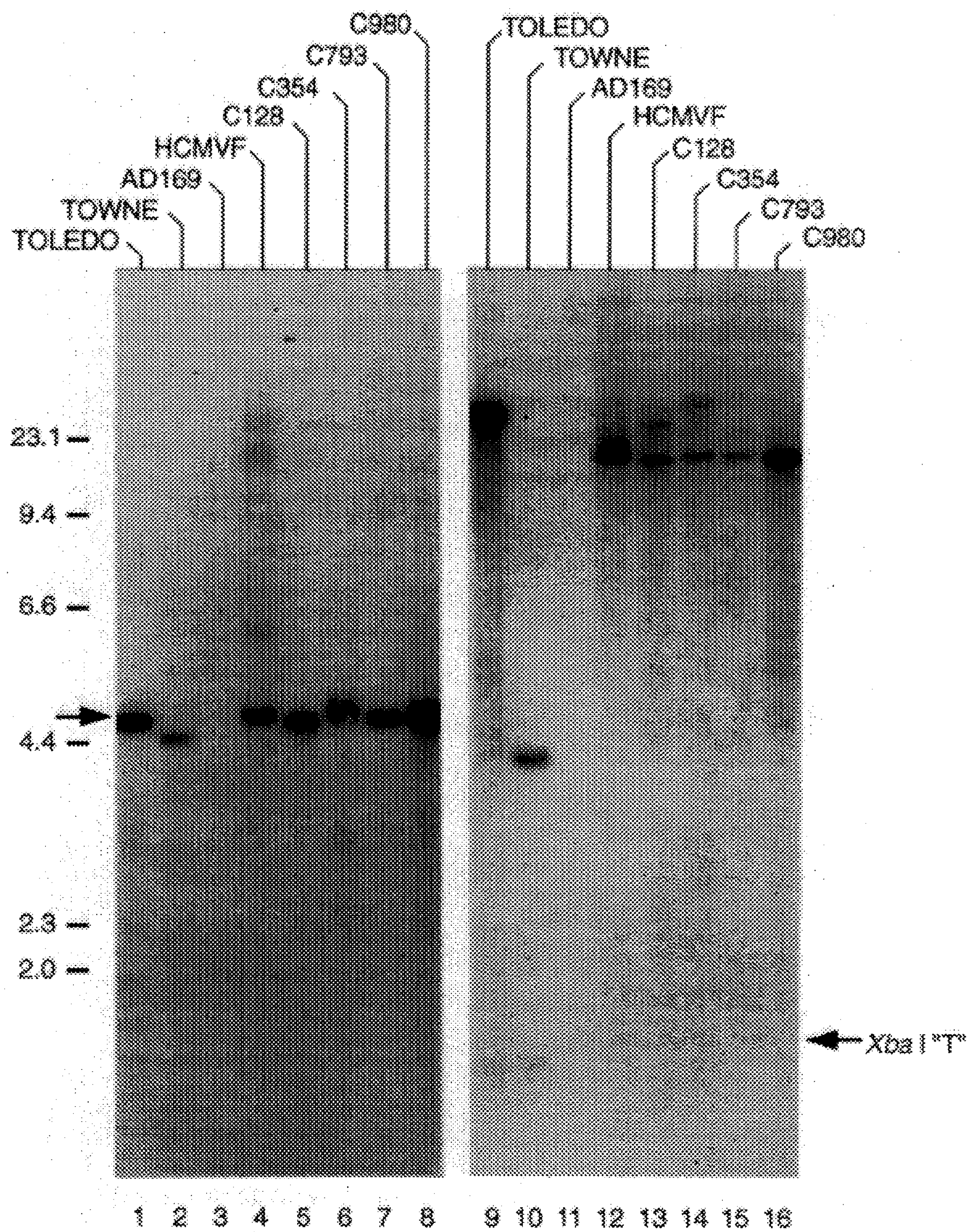
FIG._4

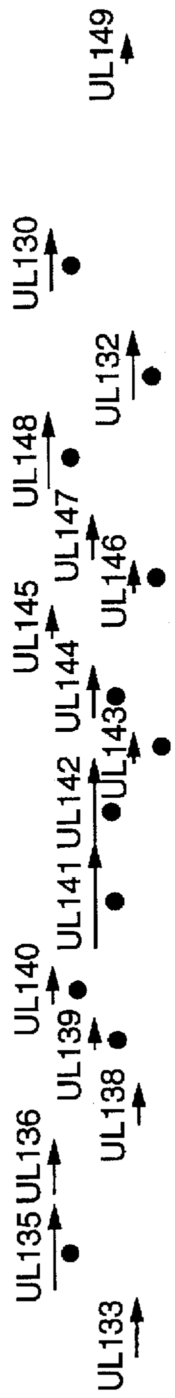
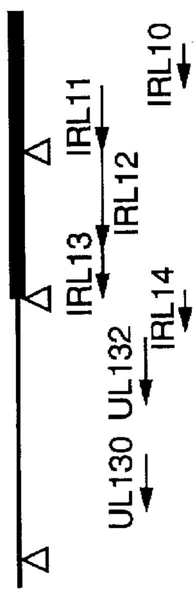
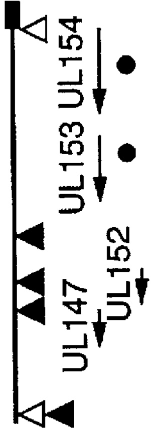
*FIG._5*

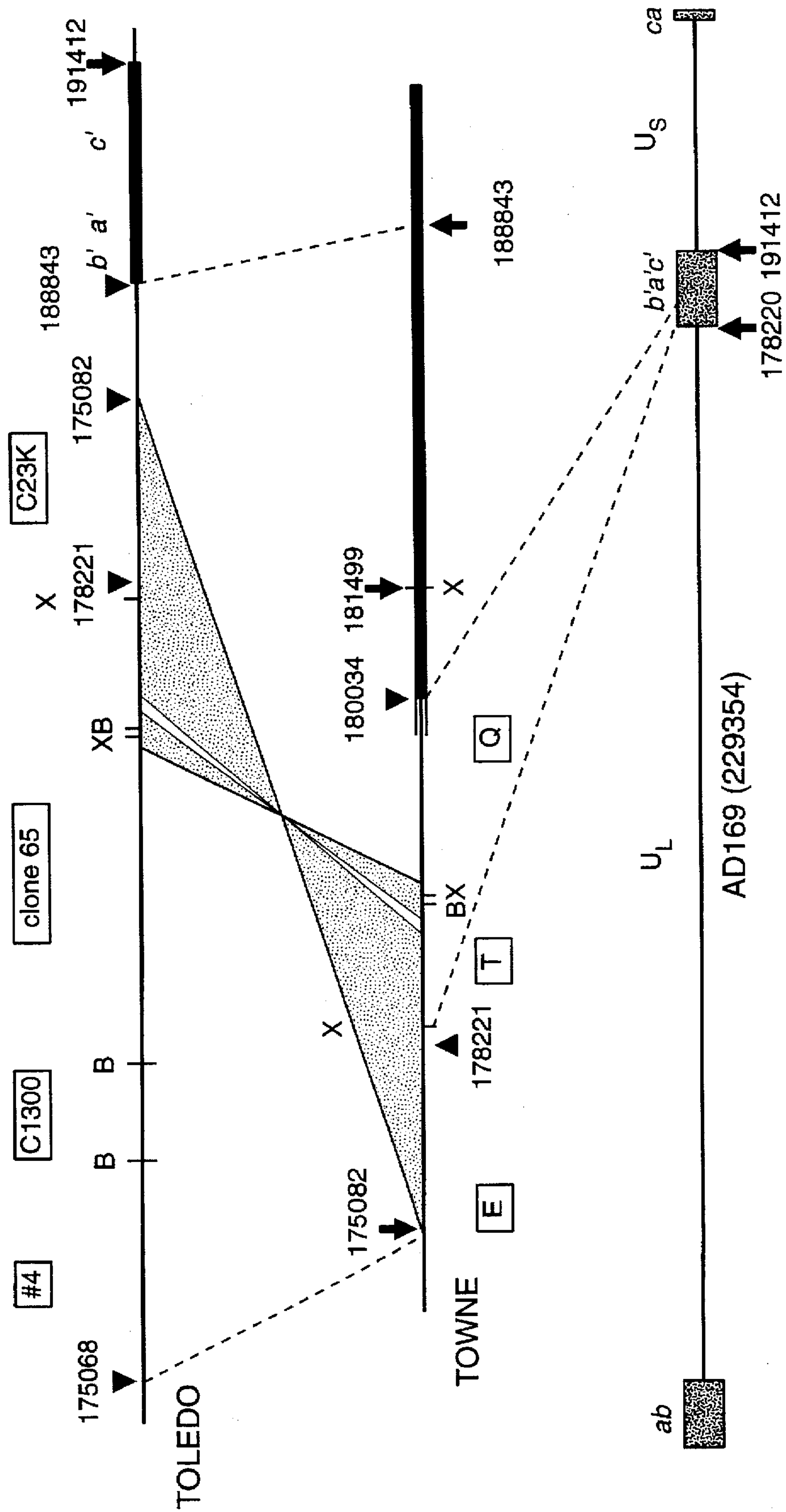
FIG._6

HUMAN CYTOMEGALOVIRUS DNA SEQUENCES

TECHNICAL FIELD

This invention pertains to the field of virology, specifically to the diagnosis, treatment and prevention of viral infections in humans. More specifically, this invention relates to the diagnosis, treatment and prevention of human cytomegalovirus infections.

BACKGROUND

Human cytomegalovirus (HCMV) is a ubiquitous agent in human populations. Infections are generally asymptomatic, but there can be serious medical sequelae in immunocompromised individuals and in congenitally infected newborns. In immunocompromised individuals, HCMV infection can result in interstitial pneumonia, retinitis progressing to blindness and disseminated infection. Infections in newborns can be severely damaging, with multiple organ involvement including the central nervous system and may also result in auditory damage. The mechanisms of pathogenesis are not understood, although it is believed that host factors, such as cellular and/or humoral immune responses might be involved. See, Alford and Britt, "The Human Herpesviruses", eds Roizman, B., R. J. Whitley and C. Lopez, Raven Press, New York, 1993, pp 227–55. It has also been speculated that genetic variability (either structural or antigenic or both) among different strains of HCMV could be responsible for the variance in clinical manifestations observed. Pritchett, *J. Virol.* 36:152–61(1980); Lehner, J. Clin. Microbiol. 29:2494–2502(1991); Fries, *J. Infect. Dis.* 169:769–74(1994).

Considerable attention has been focused recently on the analysis of strain variation among HCMV isolates. Some twenty different HCMV strains have been isolated and differentiated by restriction analysis of PCR amplified DNA fragments. Chou, *J. Infect. Dis.* 162:738–42(1994).

One strain, the Towne strain, has been developed into a live, attenuated vaccine and administered with some success in renal transplant patients. See Quinnan, *Annals of Int. Meal.* 101:478–83(1984); Plotkin, *Lancet* 1:528–30(1984). However, Towne strain vaccines who were directly challenged by low-passaged Toledo strain wild-type virus in one study were found to resist challenge doses of only 10 plaque-forming units (pfu) or less. Plotkin, *J. Infect. Dis.* 159:860–65(1989). Therefore, it appears the Towne strain may be overly attenuated, i.e., genetically modified so extensively resulting from serial passage in cell culture that it has lost significant immunogenicity presumably due to the loss of genetic information during the cell passage. Advantageously however, the Towne strain has never been shown to reactivate.

DNA sequence heterogeneity between the Towne strain and another strain of HCMV, AD169, has been found. Pritchett, *J. Virol.* 36:152–61(1980). (A restriction map of the AD169 HCMV genome is disclosed in U.S. Pat. No. 4,762,780.) Variation in the DNA content among other isolated strains of HCMV has also been detected. Huang, *Yale J. Biol. and Med.* 49:29–43(1976). Cleavage patterns of restriction enzyme digests of HCMV DNA of various strains has been analyzed. Kilpatrick, *J. Virol.* 18:1095–1105 (1976); LaFemina, "Structural Organization of the DNA Molecules from Human Cytomegalovirus" in *Animal Virus Genetics,* eds. Field, B. N. and R. Jaenish, Academic Press, NY (1980); Chandler, *J. Gen. Virol.* 67:2179–92(1986); Zaia, *J. Clin. Microbiol.* 28:2602–07(1990). However, although the gross structural organization of the HCMV genome has been determined and strain-to-strain restriction site polymorphism mapped for many of the strains, strain-to-strain differences in the DNA sequences of the HCMV genome have not been determined. Only partial sequences have been deduced and compared. For example, the DNA and amino acid sequences of the envelope glycoprotein B [gpUL55(gB)] of both Towne and AD169 strains have been deduced, see Spaete, *Virology* 167:207–25(1988), and compared with various clinical isolates, see Chou, *J. Infect. Dis.* 163:1229–34(1991), to identify conserved regions and regions of variability. In addition, DNA sequence analysis of certain regions of the gp58/116 gene [gpUL55(gB)], the IMP gene and the IE-1/2 enhancer/promoter has been accomplished. Lehner, *J. Clin. Microbiol.* 29:2494–2502(1991).

Whereas the complete DNA sequence of the AD169 strain of HCMV has been deduced, (EMBL Accession No. X17403), the complete DNA sequence of the Towne strain has not to our knowledge been deduced. However, it has been speculated that AD169 and another laboratory strain, Davis, are missing two to four kilobase pairs (kb) of DNA sequence compared to the Towne strain at the extreme internal portions of both L repeats. LeFemina, supra, at 52–53.

The public health impact of HCMV infections has not been well controlled by current treatment strategies or available antiviral chemotherapies. Preventative vaccine strategies are likely to prove efficacious because of the observations that seropositive renal allograft recipients are protected from severe HCMV disease and maternal immunity protects the fetus from disease after intrauterine infection. Marshall and Plotkin, "Cytomegalovirus Vaccines" in The Human Herpesviruses, eds Roizman, B., R. J. Whitley and C. Lopez, Raven Press, New York, 1993, pps 381–95. However, an additional obstacle to the development of a vaccine for HCMV is the lack of an animal model system that can be used to test the safety and efficacy of vaccine candidates.

There remains a need in the art for efficacious vaccines for the prophylactic treatment of HCMV in humans.

SUMMARY OF THE INVENTION

In one aspect, the invention provides novel HCMV DNA sequences not heretofore recognized or known in the art. These novel HCMV sequences were isolated from the Toledo and Towne strains of HCMV and comprise DNA that is not shared by reference strain AD169 of HCMV. Accordingly, in this aspect the invention provides novel, isolated, Toledo strain HCMV DNA sequences. As used herein, "isolated" means substantially free from other viral DNA sequences with which the subject DNA is typically found in its native, i.e., endogenous, state. These novel Toledo HCMV DNA sequences are characterized by comprising the same or substantially the same nucleotide sequence as in FIG. 1 (SEQ ID NO:6), or active fragments thereof. The DNA sequences may include 5' and 3' non-coding sequences flanking the coding sequence. The DNA sequences may be in inverted orientation with respect to the orientation shown in FIG. 1. Segments or fragments of the DNA sequence shown in FIG. 1 (SEQ ID NO:6) may be rearranged or inverted internally. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 1. FIG. 1 (SEQ ID NO:6) illustrates the DNA sequence of the novel Toledo strain HCMV. Twenty one open reading frames (ORFs) were identified in this sequence. The putative amino acid sequences of these novel Toledo strain HCMV ORFs am enumerated in sequence identification numbers 7 through 27, pages 58 through 78, infra. In FIG. 1, the beginning and ending of the 21 ORFs are identified by the arrows and the designations "UL133", "UL134", etc. (see infra.). In rearranged sequences of the invention, novel open reading frames may be created or destroyed.

In another aspect, the invention provides additional novel HCMV DNA sequences not heretofore recognized or known in the art. These additional sequences were isolated from the Towne strain of HCMV and comprise DNA that is not shared by the AD169 strain or by the Toledo strain of HCMV. Accordingly, in this aspect the invention provides novel Towne strain HCMV sequences. These novel Towne HCMV DNA sequences are characterized by as comprising the same or substantially the same nucleotide sequence as in FIG. 2 (SEQ ID NO:1), or active fragments thereof. The DNA sequence may include 5' and 3' non-coding sequences flanking the coding sequence. The DNA sequences of the invention also comprise nucleotide sequences capable of hybridizing under stringent conditions, or which would be capable of hybridizing under said conditions but for the degeneracy of the genetic code to a sequence corresponding to the sequence of FIG. 2 (SEQ ID NO:1). FIG. 2 (SEQ ID NO:1) illustrates the DNA sequence of the novel Towne strain HCMV. Four ORFs were identified in this sequence. The putative amino acid sequences of these novel ORFs are enumerated in sequence identification numbers 2 through 5, pages 42 through 45 infra. In FIG. 2, the beginning and ending of the 40RFs are identified by the arrows and the designations UL147, UL152, UL153 and UL154.

It is understood that the DNA sequences of this invention may exclude some or all of the signal and/or flanking sequences. In addition, the DNA sequences of the present invention may also comprise DNA capable of hybridizing under stringent conditions, or which would be capable of hybridizing under such conditions but for the degeneracy of the genetic code, to an isolated DNA sequence of FIG. 1 or FIG. 2. (SEQ ID NOS:6 and 1). As used herein, "stringent conditions" means conditions of high stringency, for example 6×SSC, 0.2% polyvinylpyrrolidone, 0.2% Ficoll, 0.2% bovine serum albumin, 0.1% sodium dodecyl sulfate, 100 μg/ml salmon sperm DNA and 15% formamide at 68 degrees C. (See Materials and Methods, Part C, infra.)

Accordingly, the DNA sequences of this invention may contain modifications in the non-coding sequences, signal sequences or coding sequences, based on allelic variation, species or clinical isolate variation or deliberate modification. Using the sequences of FIG. 1 and 2 (SEQ ID NOS:6 and 1), it is within the skill in the art to obtain other modified DNA sequences: the sequences can be truncated at their 3'-termini and/or their 5'-termini, the gene can be manipulated by varying individual nucleotides, while retaining the original amino acid(s), or varying the nucleotides, so as to modify amino acid(s). Nucleotides can be substituted, inserted or deleted by known techniques, including for example, in vitro mutagenesis and primer repair. In addition, short, highly degenerate oligonucleotides derived from regions of imperfect amino acid conservation can be used to identify new members of related viral and cellular families. RNA molecules, transcribed from a DNA of the invention as described above, are an additional aspect of the invention.

In another aspect, the invention provides novel HCMV proteins, which are substantially free from other HCMV proteins with which they are typically found in their native state. These novel HCMV proteins comprise the open reading frames (ORFs) UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO:17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26) identified in the novel Toledo strain DNA sequence and UL147 (SEQ ID NO:2), UL152 (SEQ ID NO:3), UL153 (SEQ ID NO:4) and/or UL154 (SEQ ID NO:5) identified in the novel Towne strain DNA sequence. Two additional HCMV ORFs were identified in the novel Toledo strain DNA sequence, UL130 and UL132 (SEQ ID NOS:23 and 27). These two sequences are also present in AD169 (see FIG. 5). The proteins may be produced by recombinant genetic engineering techniques. They may additionally be purified from cellular sources infected with HCMV. They may also be synthesized by chemical techniques. One skilled in the art could apply a combination of the above-identified methodologies to synthesize the protein. Additionally, analogs of the HCMV proteins of the invention are provided and include truncated polypeptides, e.g., routants in which there are variations in the amino acid sequence that retain biological activity, as defined below, and preferably have a homology of at least 80%, more preferably 90%, and most preferably 95%, with the corresponding regions of the HCMV Towne or Toledo amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27). Examples include polypeptides with minor amino acid variations from the native amino acid sequences of HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27); in particular, conservative amino acid replacements. Conservative replacements are those that take place within a family of amino acids that are related in their side chains. Genetically encoded amino acids are generally divided into four families: (1) acidic=aspartate, glutamate; (2)basic=lysine, arginine, histidine; (3)non-polar =alanine, valine, leucine, isoleucine, proline, phenylalanine, methionine, tryptophan; and (4) uncharged polar=glycine, asparagine, glutamine, cystine, serine, threonine, tyrosine. Phenylalanine, tryptophan, and tyrosine are sometimes classified jointly as aromatic amino acids. For example, it is reasonable to expect that an isolated replacement of a leucine with an isoleucine or valine, an aspartate with a glutamate, a threonine with a serine, or a similar conservative replacement of an amino acid with a structurally related amino acid will not have a major effect on activity or functionality.

Using the Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27) it is within the skill in the art to obtain other polypeptides or other DNA sequences encoding the HCMV Toledo or Towne protein from clinical isolates of HCMV. For example, the structural gene can be manipulated by varying individual nucleotides, while retaining the correct amino acid(s), or varying the nucleotides, so as to modify the amino acids, without loss of activity. Nucleotides can be substituted, inserted, or deleted by known techniques, including, for example, in vitro mutagenesis and primer repair. The structural gene can be truncated at its 3'-terminus and/or its 5'-terminus while retaining its activity. It also may be desirable to remove the region encoding the signal sequence, and/or to replace it with a heterologous sequence. It may also be desirable to ligate a portion of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27), particularly that which includes the amino terminal domain to a heterologous coding sequence, and thus to create a fusion peptide of HCMV Toledo or Towne.

In designing such modifications, it is expected that changes to nonconserved regions of the HCMV Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27) will have relatively smaller effects on activity, whereas changes in the conserved regions, and particularly in or near the amino terminal domain are expected to produce larger effects. Amino acid residues that are conserved between the HCMV Toledo or Towne amino acid sequences (SEQ ID NOS:2, 3, 4, 5, 7, 8, 9, 10, 11, 12, 14, 15, 17, 18, 19, 21, 22, 23, 24, 25, 26, and 27) and at least two other sequences, for example, from HCMV clinical isolates are not expected to be candidates for substitution. A residue which shows conservative variations among the HCMV sequences and at least two of the other sequences is expected to be capable of similar conservative substitution of the HCMV sequences. Similarly, a residue which varies nonconservatively among the HCMV sequences and at least three of the other sequences is expected to be capable of either conservative or nonconservative substitution. When designing substitutions to the HCMV sequences, replacement by an amino acid which is found in the comparable aligned position of one of the other sequences is especially preferred.

Additionally provided by this invention is a recombinant DNA vector comprising vector DNA and a DNA sequence encoding an HCMV Toledo polypeptide or HCMV Towne polypeptide. The vector provides the HCMV Toledo or Towne DNA in operative association with a regulatory sequence capable of directing the replication and expression of an HCMV Toledo or Towne protein in a selected host cell. Host cells transformed with such vectors for use in expressing recombinant HCMV Toledo or Towne proteins are also provided by this invention. Also provided is a novel process for producing recombinant HCMV Toledo or Towne proteins or active fragments thereof. In this process, a host cell line transformed with a vector as described above containing a DNA sequence (SEQ ID NOS: 1 and 6) encoding expression of an HCMV Toledo or Towne protein in operative association with a suitable regulatory sequence capable of directing replication and controlling expression of an HCMV Toledo or Towne protein is cultured under appropriate conditions permitting expression of the recombinant DNA. The expressed protein is then harvested from the host cell or culture medium using suitable conventional means. This novel process may employ various known cells as host cell lines for expression of the protein. Currently preferred cells are mammalian cell lines, yeast, insect and bacterial cells. Especially preferred are mammalian cell lines.

The practice of the invention will employ, unless otherwise indicated, conventional techniques of molecular biology, microbiology, recombinant DNA manipulation and production, and immunology, which are within the skill of the art. Such techniques are explained fully in the literature. See, e.g., Sambrook, *Molecular Cloning; A Laboratory Manual*, Second Edition (1989); *DNA Cloning*, Volumes I and II (D. N. Glover, Ed. 1985); *Oligonucleotide Synthesis* (M. J. Gait, Ed. 1984); *Nucleic Acid Hybridization* (B. D. Hames and S. I. Higgins, Eds. 1984); *Transcription and Translation* (B. D. Hames and S. I. Higgins, Eds. 1984); *Animal Cell Culture* (R. I. Freshney, Ed. 1986); *Immobilized Cells and Enzymes* (IRL Press, 1986); B. Perbal, *A Practical Guide to Molecular Cloning* (1984); the series, *Methods in Enzymology* (Academic Press, Inc.); *Gene Transfer Vectors for Mammalian Cells* (J. H. Miller and M. P. Calos, Eds. 1987, Cold Spring Harbor Laboratory), *Methods in Enzymology*, Volumes 154 and 155 (Wu and Grossman, and Wu, Eds., respectively), (Mayer and Walker, Eds.) (1987); *Immunochemical Methods in Cell and Molecular Biology* (Academic Press, London), Scopes, (1987); *Protein Purification: Principles and Practice*, Second Edition (Springer-Verlag, N.Y.); and *Handbook of Experimental Immunology*, Volumes I–IV (D. M. Weir and C. C. Blackwell, Eds 1986). All patents, patent applications and publications mentioned herein, both supra and infra, are hereby incorporated by reference.

Additionally provided by this invention are compositions for detecting HCMV infections in humans. These compositions comprise probes having at least one single-stranded fragment of at least 10 bases in length, more preferably 15 bases in length, of the novel Toledo sequence, and fragments hybridizing to these single-stranded fragments under stringent hybridization conditions and non-cross-hybridizing with human DNA. Additionally, these compositions comprise at least one single-stranded fragment of at least 10 bases in length, more preferably 15 bases in length, of the novel Towne sequence, and fragments hybridizing to these single-stranded fragments under stringent hybridizing with human DNA. Such probe compositions may additionally comprise a label, attached to the fragment, to provide a detectable signal, as is taught in U.S. Pat. No. 4,762,780.

Further provided by this invention are methods for detecting an HCMV infection in a human host. Such methods comprise combining under predetermined stringency conditions a clinical sample suspected of containing HCMV DNA with at least one single-stranded DNA fragment of the novel Toledo or Towne strain of HCMV having at least 10 bases, more preferably 15 bases, and being non-cross-hybridizing with human DNA, and detecting duplex formation between the single-stranded Toledo or Towne strain HCMV fragments and the sample DNA. Alternatively, PCR may be used to increase the viral nucleic acid copy number by amplification to facilitate the identification of HCMV in infected individuals. In such case, the single-stranded Toledo or Towne strain DNA sequence fragments of the present invention can be used to construct PCR primers for PCR-based amplification systems for the diagnosis of HCMV. Such systems are well known in the art. See for example, U.S. Pat. No. 5,008,182 (detection of AIDS associated virus by PCR) and Hedrum, PCR Methods and Applications 2:167–71(1992) (detection of Chlamydia trachomatis by PCR and immunomagnetic recovery).

The DNA sequences of this invention may also be used to prepare immunizing compositions. The novel Toledo DNA sequences are recombined into the Towne strain or AD169 strain of HCMV and these recombinant viruses tested for growth properties in endothelial cells or in human tissues transplanted into SCID mice or tested in the rat eye model. Mocarski, *Proc. Nat. Acad. Sci* 90:104–08(1993). Such recombinants will show increased immunogenicity over that shown by the Towne-125 strain currently in use in humans, without exhibiting the full virulence shown by the Toledo-1 strain. Therefore, a further aspect of the invention is immunizing compositions comprising either the Towne strain or the AD169 reference strain of HCMV to which the novel Toledo DNA sequence, or analogs or fragments thereof, have been added, resulting in increased immunogenicity of the recombinant virus. The invention also includes a method for the prophylactic treatment of HCMV in humans comprising administering to a human patient an immunogenically inducing effective amount of an immunizing composition of the invention in a suitable pharmaceutical carrier. Still another aspect of the invention is a method of stimulating an immune response against CMV by administering to a patient an immunogenically inducing effective amount of an immunizing composition of the invention in a suitable pharmaceutical vehicle.

Other aspects and advantages of this invention are described in the following detailed description.

BRIEF DESCRIPTION OF THE DRAWINGS

FIG. 1A–1T illustrates the novel Toledo DNA sequence of the invention isolated from the Toledo strain of HCMV. The arrows indicate the beginnings and ends of nucleotide sequences encoding the 21 putative amino acid sequences identified.

FIG. 2A–2E illustrates the novel Towne DNA sequence of the invention isolated from the Towne strain of HCMV. The arrows indicate the beginnings and ends of the nucleotide sequences encoding the 4 putative amino acid sequences identified.

FIG. 3 is a schematic representation of a Southern blot of restriction enzyme digested Towne and Toledo HCMV strain DNA as detailed in Example 1. The arrow indicates a 5 kbp (kilobase pair) band of Toledo DNA on the BamHI digest that is lacking in the Towne DNA, signifying the presence of additional Toledo DNA sequence.

FIG. 4 illustrates a composite autoradiograph of the restriction enzyme digested DNA from AD169, Towne, Toledo and five clinical isolates of HCMV as described in Example 3.

FIG. 5 is a schematic presentation of the novel open reading frames identified in the novel Toledo and Towne DNA sequences.

FIG. 6 is a schematic illustration of the relative positions of novel sequences identified in Toledo genomic DNA, Towne genomic DNA in a comparison with AD169 strain genomic DNA.

DETAILED DESCRIPTION

A. Introduction

The invention provides two novel HCMV DNA sequences, termed Toledo sequence and Towne sequence, not heretofore recognized or known in the art. The invention also provides immunization compositions and methods using the novel HCMV DNA sequences of the invention and also provides other diagnostic and therapeutic uses for the sequences and their protein products. The new DNA sequences were originally found in the Toledo and Towne strains of HCMV. Details of the sequences and structural characteristics are provided in the Examples below.

Most desirably, HCMV immunogenic compositions are provided that comprise reference strain AD169 or Towne to which the novel Toledo DNA sequences, or analogs or fragments thereof, have been added in order to increase the immunogenicity of the overly-attenuated strain. Thus, one aspect of this invention includes isolated DNA and corresponding RNA sequences as disclosed in FIGS. 1 and 2 (SEQ ID NOS:6 and 1). As used herein, "isolated" means substantially free from other nucleotide or polypeptide sequences with which the subject nucleotide sequence or polypeptide sequence is typically found in its native, i.e., endogenous, state. In another aspect, the invention comprises isolated HCMV Towne or Toledo protein encoded by the respective HCMV Towne or Toledo DNA sequences (SEQ ID NOS:2, 3, 4, 5, 7, 8, 9, 10, 11, 12, 13, 14, 15, 16, 17, 18, 19, 20, 21, 22, 23, 24, 25, 26, and 27).

Another aspect of this invention includes diagnostic assays for the detection of HCMV strain variants. In brief, such diagnostic assays include the use of DNA sequence fragments of the invention as primers for amplifying HCMV related nucleic acids in a polymerase chain reaction (PCR) or by direct detection by hybridization. The diagnostic assays of the invention may also include the use of specific antibodies against the novel ORFs encoded by the Toledo or Towne DNA sequences disclosed here. Yet another aspect of the invention is the use of the novel DNA sequences modified with a unique restriction site, to act as vaccine markers.

It is anticipated that the invention will enable the production of vaccines that offer advantages over the current HCMV vaccine, which is overly attenuated and therefore not consistently effective in eliciting an immune response. More specifically, the introduction or insertion of the novel Toledo strain sequences of the present invention into the Towne strain or into the AD169 strain will result in the introduction of specific DNA sequences in the HCMV Towne genome that are not possible using the cell passage vaccines. Importantly for vaccine production, this enables precise measurement of the degree of attenuation introduced by different fragments of the DNA sequences of the invention, thereby enabling the controlled modification in the attenuation of the Towne strain that is needed in the art to correct the Towne's strain's overly attenuated characteristic and improve its function as an immunogenic composition.

B. Recombinant AD169 or Towne HCMV

Recombinant AD169 or Towne DNA is derived by co-transfecting a plasmid containing the novel Toledo sequence, or analogs or fragments thereof, and a selectable marker such as gpt or β-galactosidase in primary fibroblast cells, or other cell lines known to be permissive for growth of CMV. Recombinant viruses are selected by growth in media containing mycophenolic acid or identified by blue plaque phenotypes after applying a chromogenic substrate such as X-gal. Recombinant viruses are plaque purified and characterized by restriction enzyme analysis and Southern blotting procedures. The novel HCMV Toledo sequence, or analogs or fragments thereof, may be used unmodified with respect to the endogenous promoter and transcription termination signals. Alternatively, the HCMV Toledo strain DNA coding region can be placed under transcriptional control of a promoter such as the CMV (cytomegalovirus) major immediate early promoter, the SV40 early promoter or some other viral or cellular promoter that generates adequate levels of expression, as discussed herein.

Modified Towne or AD169 strain HCMV is grown in tissue culture cells. For experiments with mammals, not including humans, cells such as human foreskin fibroblasts (HF) or MRC-5 cells are used to propagate the virus. The virus is harvested from cultures of these cells and the isolated recombinant virus is then be further studied for its ability to elicit an immune response and provide protection against HCMV infection.

For use in humans, the recombinant virus is produced from an FDA approved cell line in large scale amounts. Such cells include MRC-5 or WI-38 cells (both are primary human diploid fibroblasts). The recombinant virus is generated in the production cell line by transfection of vital DNA or capsids prepared from recombinant virus isolated from another cell line. The method of transfection should prevent the contamination of FDA approved cells with adventitious agents or contaminants from a non-qualified cell line. A HCMV virus produced from the above cell lines will be used to infect progressively larger flasks of tissue culture cells. Infected cells will be used as subsequent inoculums. Viable infected tissue culture cells are removed from the tissue culture vessels using trypsin and added to a 1 to 100 fold (or more) excess of uninfected cells to accomplish progressively larger inoculations. Once an optimal yield is obtained the virus will be harvested from the tissue culture cells. This process can be repeated until a large scale production is achieved. Infected cells will be removed from the tissue culture vessel and disrupted using for example, sonication, dounce homogenization or some combination of the above. The viruses are then isolated from cellular material using centrifugation techniques known in the art. Once the virus is isolated a stabilizing agent is added, such as a carbohydrate or carbohydrate derivative and the virus is then aliquoted and lyophilized.

C. Immunogenic Compositions

Immunogenic compositions can be administered to subjects to prevent HCMV infections. The immunogenic compositions prevent HCMV infections by stimulating the immune system with an attenuated virus incapable of fully manifesting the disease. A major advantage of the HCMV immunogenic compositions provided herein is that its increased degree of immunogenicity will result in move effective prevention of an HCMV infection in the population.

The Towne strain of HCMV will preferably serve as the parent strain due to its proven inability to reactivate. To make HCMV immunogenic compositions, full, truncated and/or modified novel Toledo DNA sequences are introduced into a HCMV AD169 or Towne strain virus as discussed herein. The effectiveness of the immunogenic composition in preventing HCMV infections will be measured in humans. Humans will be first inoculated with PFU's ranging from 100–20,000 PFU of mutant virus per inoculation, PFUs are measured as discussed herein. After the first inoculation, a second booster injection of similar or increased dosage usually may be given. Subjects will be exposed to wild-type HCMV after the first or second inoculation and the occurrence of CMV infections observed. Potential side effects of the vaccine will be monitored in volunteer adults previously exposed to CMV, before inoculating subjects that have not ever developed CMV infections. Attenuated virus is used without an adjuvant and with a physiologically suitable carrier.

As is known in the art and discussed herein, the novel DNA is inserted into the Towne or AD169 viral genome using, for example, homologous recombination techniques. The insertion is generally made into a gene which is nonessential in nature. Plasmid shuttle vectors that greatly facilitate the construction of recombinant viruses have been described. See, for example, Spaete and Mocarski, *Proc. Nat. Acad. Sci* 84:7213–17(1987). Expression of the polypeptide encoded by the novel Toledo DNA then occurs in cells or individuals which are immunized with the live recombinant virus.

Alternatively, the purified novel HCMV proteins may be employed in therapeutic and/or subunit immunogenic compositions for preventing and treating HCMV related conditions. Such pharmaceutical compositions comprise an immunogenically-inducing effective amount of one or more of the proteins of the present invention in admixture with a pharmaceutically acceptable carrier, for example an adjuvant/antigen presentation system such as alum. Other adjuvant/antigen presentation systems, for instance, MF59 (Chiron Corp.), QS-21 (Cambridge Biotech Corp.), 3-DMPL (3-Deacyl-Monophosphoryl Lipid A) (RibiImmunoChem Research, Inc.), clinical grade incomplete Freund's adjuvant (IFA), fusogenic liposomes, water soluble polymers or Iscoms (Immune stimulating complexes) may also be used. Other exemplary pharmaceutically acceptable carriers or solutions are aluminum hydroxide, saline and phosphate buffered saline. The composition can be systemically administered, preferably subcutaneously or intramuscularly, in the form of an acceptable subcutaneous or intramuscular solution. Also inoculation can be effected by surface scarification or by inoculation of a body cavity. The preparation of such solutions, having due regard to pH, isotonicity, stability and the like is within the skill in the art. The dosage regimen will be determined by the attending physician considering various factors known to modify the action of drugs such as for example, physical condition, body weight, sex, diet, severity of the condition, time of administration and other clinical factors. Exemplary dosage ranges comprise between about 1 μg to about 1000 μg of protein.

In practicing the method of treatment of this invention, an immunologically- inducing effective amount of protein is administered to a human patient in need of therapeutic or prophylactic treatment. An immunologically inducing effective amount of a composition of this invention is contemplated to be in the range of about 1 microgram to about 1 milligram per dose administered. The number of doses administered may vary, depending on the above mentioned factors.

D. Diagnostic Assays and Use as a Vaccine Marker

The novel Toledo and Towne DNA sequences of the present invention can be used in diagnostic assays to detect HCMV in a sample, to detect Toledo and Towne—like sequences and to detect strain differences in clinical isolates of HCMV using either chemically synthesized or recombinant Toledo or Towne DNA fragments. Additionally, the novel sequences can be used as a vaccine marker to differentiate between an individual or sample infected with or containing wild type HCMV and an individual or sample infected with or containing a HCMV vaccine, i.e., a live attenuated HCMV vaccine currently in use such as the Towne vaccine. In yet another embodiment, fragments of the DNA sequences can also be linked to secondary nucleic acids with sequences that either bind a solid support or other detection probes for use in diagnostic assays. In one aspect of the invention, fragments of the novel Toledo or Towne DNA sequences (SEQ ID NOS:1 and 3) comprising at least between 10 and 20 nucleotides can be used as primers to amplify nucleic acids using polymerase chain reaction (PCR) methods well known in the art and as probes in nucleic acid hybridization assays to detect target genetic material such as HCMV DNA in clinical specimens (with or without PCR). See for example, U.S. Pat. Nos. 4,683,202; 4,683,195; 5,091,310; 5,008,182 and 5,168,039. In an exemplary assay, a conserved region of the novel DNA sequence among virus variants is selected as the sequence to be amplified and detected in the diagnostic assay. Oligonucleotide primers at least substantially complementary to (but preferably identical with) the sequence to be amplified are constructed and a sample suspected of containing a HCMV nucleic acid sequence to be detected is treated with primers for each strand of HCMV nucleic acid sequence to be detected, four different deoxynucleotide triphosphates and a polymerization agent under appropriate hybridization conditions such that an extension product of each primer is synthesized that is complementary to the HCMV nucleic acid sequences suspected in the sample, which extension products synthesized from one primer, when separated from its complement can serve as a template for synthesis of the extension product of the other primer in a polymerase chain reaction. After amplification, the product of the PCR can be detected by the addition of a labeled probe, likewise constructed from the novel DNA sequence, capable of hybridizing with the amplified sequence as is well known in the art. See, e.g. U.S. Pat. No. 5,008,182.

In another embodiment the probes or primers can be used in a vaccine marker assay to detect a vaccine or wild type infection. Alternatively, introduction of a restriction site into the novel DNA sequence will provide a vaccine marker that can be used with PCR fragments to detect such differences in a restriction digest. Such procedures and techniques for detecting sequence variants, such as, point mutations with the expected location or configuration of the mutation, are known in the art and have been applied in the detection of sickle cell anemia, hemoglobin C disease, diabetes and other diseases and conditions as disclosed in U.S. Pat. No. 5,137,806. These methods are readily applied by one skilled in the art to detect and differentiate between wild type and vaccine infections in HCMV.

In another embodiment the novel Toledo or Towne DNA sequences can be used in their entirety or as fragments to detect the presence of DNA sequences, related sequences, or transcription products in cells, tissues, samples and the like using hybridization probe techniques known in the art or in conjunction with one of the methods discussed herein. When used as a hybridization probe, fragments of the novel DNA sequences of the invention are preferably 50–200 nucleotides long, more preferably 100–300 nucleotides long and most preferably greater than 300 nucleotides long.

E. Vectors and Chimeric Virus Production

The novel DNA sequences of the invention can be expressed in different vectors using different techniques known in the art resulting in the generation of chimeric virus. Useful and known techniques include marker transfer or homologous recombination, direct in vitro ligation, defective vector technology and amplicon generation (see, e.g., Frenkel, N. et al., *Gene Transfer and Cancer,* edited by M. L. Pearson and N. L. Sternberg(1984), Kwong, A. D. and Frenkel, Virology 142, 421–425 (1985); U.S. patent (Ser. No. 07/923,015 by Roizman). Vectors used in such techniques include cosmids, plasmids, and infective or defective viruses. Such vectors are known in the art. (A cosmid as used herein is a plasmid containing a lambda bacteriophage cos site. The cos site is the cis signal for packaging lambda DNA. Therefore, a cosmid, unlike a plasmid, can be packaged with high efficiency into a lambda head in vitro. This technique allows cloning of very large (30–45 kbp) fragments of DNA. ) The vectors can be either single stranded or double stranded and made of either DNA or RNA.

Generally, the DNA sequence is inserted into the vector alone or linked to other HCMV genomic DNA. In direct in vitro ligation applications, the isolated sequence alone is used. In homologous recombination and marker transfer flanking nucleic acid sequences are required to effect transfer of the sequence into a HCMV viral genome. For use in viral complementation using cosmids and other vectors discussed herein the sequence (or a fragment thereof) in a vector is preferably operatively linked to at least 1 kb of HCMV genomic nucleic acid and more preferably at least 5kb of HCMV nucleic acid. The HCMV genomic nucleic acid can be on one side or both sides of the open reading frame. If only a specific region of the open reading frame is to be used to generate a mutant virus, an open reading frame or fragment thereof is inserted into a vector.

F. Novel Toledo and Towne Protein

Another aspect of the invention includes the isolated proteins encoded by the Toledo or Towne DNA sequence as taught herein. The proteins can be used to study and modify the life cycle of HCMV because they may encode surface glycoproteins that may be immunogenic and responsible for tissue tropism or influence the immune response in an infected individual. Such proteins could therefore be used in the production of a subunit vaccine against CMV. The construction of such CMV subunits vaccine candidates is known in the art. See, for example, Spaete, *Virology* 167:207–25(1988).

Twenty-one novel Toledo and four novel Towne proteins have been identified by ORF analysis. The novel Toledo proteins include UL130 (SEQ ID NO:23), UL132 (SEQ ID NO:27), UL133 (SEQ ID NO:7), UL134 (SEQ ID NO:8), UL135 (SEQ ID NO:9), UL136 (SEQ ID NO:10), UL137 (SEQ ID NO:11), UL138 (SEQ ID NO:12), UL139 (SEQ ID NO:13), UL140 (SEQ ID NO:14), UL141 (SEQ ID NO:15), UL142 (SEQ ID NO:16), UL143 (SEQ ID NO: 17), UL144 (SEQ ID NO:18), UL145 (SEQ ID NO:19), UL146 (SEQ ID NO:20), UL147 (SEQ ID NO:21), UL148 (SEQ ID NO:22), UL149 (SEQ ID NO:24), UL150 (SEQ ID NO:25), and/or UL151 (SEQ ID NO:26). UL130 is encoded by nucleotides 13109 through 13753, as shown in FIG. 1. UL132 is encoded by nucleotides 11673 through 12485, as shown in FIG. 1. UL133 is encoded by nucleotides 51 through 824, as shown in FIG. 1. UL134 is encoded by nucleotides 541 through 1068, as shown in FIG. 1. UL135 is encoded by nucleotides 941 through 1927, as shown in FIG. 1. UL136 is encoded by nucleotides 2018 through 2740, as shown in FIG. 1. UL137 is encoded by nucleotides 2599 through 2890, as shown in FIG. 1. UL138 is encoded by nucleotides 2823 through 3332, as shown in FIG. 1. UL139 is encoded by nucleotides 3895 through 4302, as shown in FIG. 1. UL140 is encoded by nucleotides 4484 through 4828, as shown in FIG. 1. UL141 is encoded by nucleotides 5098 through 6375, as shown in FIG. 1. UL142 is encoded by nucleotides 6448 through 7368, as shown in FIG. 1. UL143 is encoded by nucleotides 7353 through 7631, as shown in FIG. 1. UL144 is encoded by nucleotides 8008 through 8538, as shown in FIG. 1. UL145 is encoded by nucleotides 8867 through 9169, as shown in FIG. 1. UL146 is encoded by nucleotides 9450 through 9803, as shown in FIG. 1. UL147 is encoded by nucleotides 9868 through 10347, as shown in FIG. 1. UL148 is encoded by nucleotides 10646 through 11596, as shown in FIG. 1. UL149 is encoded by nucleotides 15756 through 16124, as shown in FIG. 1. UL150 is encoded by nucleotides 15874 through 17802, as shown in FIG. 1. UL151 is encoded by nucleotides 17289 through 18299, as shown in FIG. 1.

The novel Towne proteins include UL147, UL152, UL153 and UL154 (SEQ ID NOS:2, 3, 4 and 5, respectively). UL147 is encoded by nucleotides 841 through 1321, as shown in FIG. 2. UL152 is encoded by nucleotides 1365 through 1721, as shown in FIG. 2. UL153 is encoded by nucleotides 2501 through 3337, as shown in FIG. 2. UL154 is encoded by nucleotides 3512 through 4711, as shown in FIG. 2.

"Toledo and/or Towne protein or proteins" as used herein refer to the above sequences, also enumerated in the sequence listing. "Toledo and/or Towne protein or proteins" also refers to an homologous protein from any strain or clinical isolate of HCMV, including HCMV proteins that are at least 90% homologous to the Toledo or Towne amino acid sequences (SEQ ID NOS:2, 3, 4, 5, 7, 8, 9, 10, 11, 12, 13, 14, 15, 16, 17, 18, 19, 20, 21, 22, 23, 24, 25, 26, and 27). The Toledo or Towne protein can be modified to affect HCMV life cycle by deletion, insertion and substitution into the DNA sequence, as discussed herein, or by chemical synthesis of different amino acid sequence or by chemical modification. Truncated proteins can be formed by deletion of a portion of the DNA sequence or the introduction of termination signal(s) into the DNA sequence. Preferred deletions to the protein correspond to deleted amino acid sequence or sequences that contain at least one amino acid selected from the group consisting of Glu, Asp, Arg, Lys, Cys and Pro. More preferably at the deleted amino acid sequence or sequences contain at least two amino acids selected from the group consisting of Glu, Asp, Arg, Lys, Cys and Pro. More preferably the deleted amino acid sequence or sequences contain at least two prolines.

Other mutations of the protein useful in modifying HCMV life cycle include, but are not limited to, modification of cAMP phosphorylation (Arg/Lys-Arg/Lys-X-X-Asp/Glu) and/or, myristylization sites (Glycine-XI-X2-X3-Ser/Thr-X-X-Asp/Glu; where X1 is not Glu,Asp,Arg, Lys, His Pro, Phe, Tyr, Trp, where X2 is any amino acid and where X3 is not Pro), or modification of the PKC phosphorylation sites (Ser/Thr-X-Arg/Lys) and/or N-linked glycosylation sites (Asn-X-Ser/Thr; where X is not Pro).

The Toledo or Towne DNA sequences, analogs or fragments thereof can be expressed in a mammalian, insect, or microorganism host. The polynucleotide is inserted into a suitable expression vector compatible with the type of host cell employed and is operably linked to the control elements within that vector. Vector construction employs techniques which are known in the art. Site-specific DNA cleavage involved in such construction is performed by treating with suitable restriction enzymes under conditions which generally are specified by the manufacturer of these commercially available enzymes. A suitable expression vector is one that is compatible with the desired function (e.g., transient expression, long term expression, integration, replication, amplification) and in which the control elements are compatible with the host cell.

Mammalian Cell Expression

Vectors suitable for replication in mammalian cells are known in the art, and can include viral replicons, or sequences that ensure integration of the sequence encoding the Toledo or Towne DNA into the host genome. Exemplary vectors include those derived from SV40, retroviruses, bovine papilloma virus, vaccinia virus, other herpesviruses and adenovirus.

Such suitable mammalian expression vectors contain a promoter to mediate transcription of foreign DNA sequences and, optionally, an enhancer. Suitable promoters are known in the art and include viral promoters such as those from SV40, cytomegalovirus (CMV), Rous sarcoma virus (RSV), adenovirus (ADV), and bovine papilloma virus (BPV).

The optional presence of an enhancer, combined with the promoter described above, will typically increase expression levels. An enhancer is any regulatory DNA sequence that can stimulate transcription up to 1000-fold when linked to endogenous or heterologous promoters, with synthesis beginning at the normal mRNA start site. Enhancers are also active when placed upstream or downstream from the transcription initiation site, in either normal or flipped orientation, or at a distance of more than 1000 nucleotides from the promoter. See Maniatis, *Science* 236:1237(1987), Alberts, *Molecular Biology of the Cell*, 2nd Ed. (1989). Enhancers derived from viruses may be particularly useful, because they typically have a broader host range. Examples include the SV40 early gene enhancer (see Dijkema, *EMBO J.* 4:761(1985)) and the enhancer/promoters derived from the long terminal repeat (LTR) of the RSV (see Gorman, *Proc. Natl. Acad. Sci.* 79:6777(1982b)) and from human cytomegalovirus (see Boshart, *Cell* 41:521(1985)). Additionally, some enhancers are regulatable and become active only in the presence of an inducer, such as a hormone or metal ion (see Sassone-Corsi and Borelli, Trends Genet. 2:215(1986)); Maniatis, *Science* 236: 1237(1987)). In addition, the expression vector can and will typically also include a termination sequence and poly(A) addition sequences which are operably linked to the Toledo or Towne coding sequence.

Sequences that cause amplification of the gene may also be desirably included in the expression vector or in another vector that is co-translated with the expression vector containing a Towne or Toledo DNA sequence, as are sequences which encode selectable markers. Selectable markers for mammalian cells are known in the art, and include for example, thymidine kinase, dihydrofolate reductase (together with methotrexate as a DHFR amplifier), aminoglycoside phosphotransferase, hygromycin B phosphotransferase, asparagine synthetase, adenosine deaminase, metallothionien, and antibiotic resistant genes such as neomycin.

The vector that encodes a novel Toledo or Towne protein or polypeptide of this invention can be used for transformation of a suitable mammalian host cell. Transformation can be by any known method for introducing polynucleotide into a host cell, including, for example packaging the polynucleotide in a virus and transducing a host cell with the virus. The transformation procedure used depends upon the host to be transformed. Methods for introduction of heterologous polynucleotide into mammalian cells are known in the art and include dextran-mediated transfection, calcium phosphate precipitation, polybrene mediated transfection, protoplast fusion, electroporation, encapsulation of the polynucleotide(s) in liposomes, and direct microinjection of the DNA into nuclei.

Mammalian cell lines available as hosts for expression are known in the an and include many immortalized cell lines available from the American Type Culture Collection (ATCC), including but not limited to Chinese hamster ovary (CHO) cells, HeLa cells, baby hamster kidney (BHK) cells, monkey kidney cells (COS), human hepatocellular carcinoma cells (e.g., Hep G2), and a number of other cell lines.

Insect Cell Expression

The components of an insect cell expression system include a transfer vector, usually a bacterial plasmid, which contains both a fragment of the baculovirus genome, and a convenient restriction site for insertion of the heterologous gene or genes to be expressed; a wild type baculovirus with a sequence homologous to the baculovirus-specific fragment in the transfer vector (this allows for the homologous recombination of the heterologous gene in to the baculovirus genome); and appropriate insect host cells and growth media. Exemplary transfer vectors for introducing foreign genes into insect cells include pAc373 and pVL985. See Luckow and Summers, Virology 17:31(1989).

The plasmid can also contains the polyhedron polyadenylation signal and a procaryotic ampicillin-resistance (amp) gene and origin of replication for selection and propagation in E. coli. See Miller, *Ann. Rev. Microbiol.* 42: 177(1988).

Baculovirus transfer vectors usually contain a baculovirus promoter, i.e., a DNA sequence capable of binding a baculovirus RNA polymerase and initiating the downstream (5' to 3') transcription of a coding sequence (e.g., structural gene) into mRNA. The promoter will have a transcription initiation region which is usually placed proximal to the 5' end of the coding sequence and typically includes an RNA polymerase binding site and a transcription initiation site. A baculovirus transfer vector can also have an enhancer, which, if present, is usually distal to the structural gene. Expression can be either regulated or constitutive.

Yeast And Bacteria Expression

A yeast expression system can typically include one or more of the following: a promoter sequence, fusion partner sequence, leader sequence, transcription termination sequence. A yeast promoter, capable of binding yeast RNA polymerase and initiating the downstream (3 ') transcription of a coding sequence (e.g. structural gene) into mRNA, will have a transcription initiation region usually placed proximal to the 5' end of the coding sequence. This transcription initiation region typically includes an RNA polymerase binding site (a "TATA Box") and a transcription initiation site. The yeast promoter can also have an upstream activator sequence, usually distal to the structural gene. The activator sequence permits inducible expression of the desired heterologous DNA sequence. Constitutive expression occurs in the absence of an activator sequence. Regulated expression can be either positive or negative, thereby either enhancing or reducing transcription.

Particularly useful yeast promoters include alcohol dehydrogenase (ADH) (EP Patent Pub. No. 284 044), enolase, glucokinase, glucose-6-phosphate isomerase, glyceraldehyde-3-phosphate-dehydrogenase (GAP or GAPDH), hexokinase, phosphofructokinase, 3-phosphoglycerate mutase, and pyruvate kinase (PyK)(EP Patent Pub. No. 329 203). The yeast PHO5 gene, encoding acid phosphatase, also provides useful promoter sequences. See Myanohara, *Proc. Natl. Acad. Sci. USA*80:1(1983).

A Toledo or Towne DNA sequence, analog or an active fragment thereof can be expressed intracellularly in yeast. A promoter sequence can be directly linked with the sequence or fragment, in which case the first amino acid at the N-terminus of the recombinant protein will always be always be a methionine, which is encoded by the ATG start codon. If desired, methionine at the N-terminus can be cleaved from the protein by in vitro incubation with cyanogen bromide.

Intracellularly expressed fusion proteins provide an alternative to direct expression of a sequence. Typically, a DNA sequence encoding the N-terminal portion of a stable protein, a fusion partner, is fused to the 5' end of heterologous DNA encoding the desired polypeptide. Upon expression, this construct will provide a fusion of the two amino acid sequences. For example, the yeast or human superoxide dismutase (SOD) gene, can be linked at the 5' terminus of a sequence and expressed in yeast. The DNA sequence at the junction of the two amino acid sequences may or may not encode a clearable site. See, e.g., EP Patent Pub. No. 196 056. Alternatively, the polypeptides can also be secreted from the cell into the growth media by creating a fusion protein comprised of a leader sequence fragment that provides for secretion in yeast or bacteria of the polypeptides. Preferably, there are processing sites encoded between the leader fragment and the sequence that can be cleaved either in vivo or in vitro. The leader sequence fragment typically encodes a signal peptide comprised of hydrophobic amino acids which direct the secretion of the protein from the cell. DNA encoding suitable signal sequences can be derived from genes for secreted yeast proteins, such as the yeast invertase gene (EP Patent Pub. No. 12 873) and the A-factor gene (U.S. Pat. No. 4,588,684). Alternatively, leaders of non-yeast origin, such as an interferon leader, can be used to provide for secretion in yeast (EP Patent Pub. No. 60057). Transcription termination sequences recognized by yeast are regulatory regions located 3' to the translation stop codon. Together with the promoter they flank the desired heterologous coding sequence. These flanking sequences direct the transcription of an mRNA which can be translated into the polypeptide encoded by the DNA.

Typically, the above described components, comprising a promoter, leader (if desired), coding sequence of interest, and transcription termination sequence, are put together in plasmids capable of stable maintenance in a host, such as yeast or bacteria. The plasmid can have two replication systems, so it can be maintained as a shuttle vector, for example, in yeast for expression and in a procaryotic host for cloning and amplification. Examples of such yeast-bacteria shuttle vectors include YEp24 (see Botstein, *Gene* 8:17–24 (1979)), pCl/1 (see Brake, *Proc. Natl. Acad. Sci. USA* 81:4642–4646(1984)), and YRp17 (see Stinchcomb, *J. Mol. Biol.* 158:157(1982)). In addition, the plasmid can be either a high or low copy number plasmid. A high copy number plasmid will generally have a copy number ranging from about 5 to about 200, and typically about 10 to about 150. A host containing a high copy number plasmid will preferably have at least about 10, and more preferably at least about 20. Either a high or low copy number vector may be selected, depending upon the effect on the host of the vector and the polypeptides. See, e.g., Brake, et al., supra.

Alternatively, the expression constructs can be integrated into the yeast genome with an integrating vector. Integrating vectors typically contain at least one sequence homologous to a yeast chromosome that allows the vector to integrate, and preferably contain two homologous sequences flanking the expression construct. See Orr-Weaver, *Methods In Enzymol.* 101:228–245(1983)and Rine, *Proc. Natl. Acad. Sci. USA* 80:6750(1983).

Typically, extrachromosomal and integrating expression vectors can contain selectable markers to allow for the selection of yeast strains that have been transformed. Selectable markers can include biosynthetic genes that can be expressed in the yeast host, such as ADE2, HIS4, LEU2, TRP1, and ALG7, and the G418 resistance gene, which confer resistance in yeast cells to tunicamycin and G418, respectively. In addition, a suitable selectable marker can also provide yeast with the ability to grow in the presence of toxic compounds, such as metal. For example, the presence of CUP1 allows yeast to grow in the presence of copper ions. See Butt, *Microbiol. Rev.* 51:351(1987).

Alternatively, some of the above described components can be put together into transformation vectors. Transformation vectors are typically comprised of a selectable marker that is either maintained in a replicon or developed into an integrating vector, as described above. Expression and transformation vectors, either extrachromosomal or integrating, have been developed for transformation into many yeasts. Exemplary yeasts cell lines are *Candida albicans* (Kurtz, *Mol. Cell. Biol.* 6:142(1986), *Candida maltosa* (Kunze, *J. Basic Microbiol.* 25:141(1985), *Hansenula polymorpha* (Gleeson, *J. Gen. Microbiol.* 132:3459(1986) and Roggenkamp, *Mol. Gen. Genet.* 202:302(1986), *Kluyveromyces fragilis* (Das, *J. Bacteriol.* 158:1165(1984), *Kluyveromyces lactis* (De Louvencourt, *J. Bacteriol.* 154:737(1983)

and Van den Berg, *Bio/Technology* 8:135(1990), *Pichia guillerimondii* (Kunze, *J. Basic Microbiol.* 25: 141(1985), *Pichia pastoris* (Cregg, *Mol. Cell. Biol.* 5:3376 (1985), *Saccharomyces cerevisiae* (Hinnen, *Proc. Natl. Acad. Sci. USA* 75:1929(1978) and Ito, *J. Bacteriol.* 153:163(1983), *Schizosaccharomyces pombe* (Beach and Nurse, *Nature* 300:706(1981), and *Yarrowia lipolytica* (Davidow, *Curr. Genet.* 10:380471(1985) and Gaillardin, *Curr. Genet.* 10:49 (1985).

Methods of introducing exogenous DNA into yeast hosts are well-known in the art, and typically include either the transformation of spheroplasts or of intact yeast cells treated with alkali cations. Transformation procedures usually vary with the yeast species to be transformed. See the publications listed in the foregoing paragraph for appropriate transformation techniques.

Additionally, the gene or fragment thereof can be expressed in a bacterial system. In such system, a bacterial promoter is any DNA sequence capable of binding bacterial RNA polymerase and initiating the downstream (3') transcription of a coding sequence (e.g. a desired heterologous gene) into MRNA. A promoter will have a transcription initiation region which is usually placed proximal to the 5' end of the coding sequence. This transcription initiation region typically includes an RNA polymerase binding site and a transcription initiation site. A bacterial promoter can also have a second domain called an operator, that can overlap an adjacent RNA polymerase binding site at which RNA synthesis begins. The operator permits negative regulated (inducible) transcription, as a gene repressor protein can bind the operator and thereby inhibit transcription of a specific gene. Constitutive expression can occur in the absence of negative regulatory elements, such as the operator. In addition, positive regulation can be achieved by a gene activator protein binding sequence, which, if present is usually proximal (5') to the RNA polymerase binding sequence. An example of a gene activator protein is the catabolite activator protein (CAP), which helps initiate transcription of the lac operon in *Escherichia coli* (*E. coli*). See Raibaud, *Ann. Rev. Genet.* 18:173(1984). Regulated expression can therefore be either positive or negative, thereby either enhancing or reducing transcription.

Sequences encoding metabolic pathway enzymes provide particularly useful promoter sequences. Examples include promoter sequences derived from sugar metabolizing enzymes, such as galactose, lactose (lac) (see Chang, *Nature* 198:1056(1977), and maltose. Additional examples include promoter sequences derived from biosynthetic enzymes such as tryptophan (trp) (see Goeddel, *Nuc. Acids Res.* 8:4057(1981), Yelverton, *Nuc. Acids Res.* 9:731(1981), U.S. Pat. No. 4,738,921 and EP Patent Pub. Nos. 36 776 and 121 775). The lactomase (bla) promoter system (see Weissmann, *Interferon* 3 (ed. I. Gresser), the bacteriophage lambda PL promoter system (see Shimatake, *Nature* 292:128(128) and the T5 promoter system (U.S. Pat. No. 4,689,406) also provides useful promoter sequences.

In addition, synthetic promoters which do not occur in nature also function as bacterial promoters. For example, transcription activation sequences of one bacterial or bacteriophage promoter can be joined with the operon sequences of another bacterial or bacteriophage promoter, creating a synthetic hybrid promoter such as the tac promoter (see U.S. Pat. No. 4,551,433, Amann, *Gene* 25:167 (1983) and de Boer, *Proc. Natl. Acad. Sci.* 80:21(1983)). A bacterial promoter can include naturally occurring promoters of non-bacterial origin that have the ability to bind bacterial RNA polymerase and initiate transcription. A naturally occurring promoter of non-bacterial origin can be coupled with a compatible RNA polymerase to produce high levels of expression of some genes in prokaryotes. The bacteriophage T7 RNA polymerase/promoter system is exemplary. (see Studier, *J. Mol. Biol.* 189:113(1986) and Tabor, *Proc. Natl. Acad. Sci.* 82:1074(1985)).

In addition to a functioning promoter sequence, an efficient ribosome binding site is also useful for the expression of the DNA sequence or fragment thereof in prokaryotes. In *E. coli*, the ribosome binding site is called the Shine-Dalgarno (SD) sequence and includes an initiation codon (ATG) and a sequence 3–9 nucleotides in length located 3–11 nucleotides upstream of the initiation codon (see Shine, *Nature* 254:34(1975). The SD sequence is thought to promote binding of MRNA to the ribosome by the pairing of bases between the SD sequence and the 3' and of *E. coli* 16S rRNA (see Steitz, *Biological Regulation and Development: Gene Expression* (ed. R. F. Goldberger)(1979)).

The novel Toledo or Towne proteins of the invention can be expressed intracellularly. A promoter sequence can be directly linked with a novel Toledo or Towne DNA sequence, analog or a fragment thereof, in which case the first amino acid at the N-terminus will always be a methionine, which is encoded by the ATG start codon. If desired, methionine at the N-terminus can be cleaved from the protein by in vitro incubation with cyanogen bromide or by either in vivo on in vitro incubation with a bacterial methionine N-terminal peptidase. See EP Patent Pub. No. 219 237.

Fusion proteins provide an alternative to direct expression. Typically, a DNA sequence encoding the N-terminal portion of an endogenous bacterial protein, or other stable protein, is fused to the 5' end of heterologous coding sequences. Upon expression, this construct will provide a fusion of the two amino acid sequences. For example, the bacteriophage lambda cell gene can be linked at the 5' terminus of an sequence fragment thereof and expressed in bacteria. The resulting fusion protein preferably retains a site for a processing enzyme (factor Xa) to cleave the bacteriophage protein from the sequence or fragment thereof (see Nagai, *Nature* 309:810(1984). Fusion proteins can also be made with sequences from the lacZ gene (Jia, *Gene* 60: 197(1987),the trpE gene (Allen, *J. Biotechnol.* 5:93(1987) and Makoff, *J. Gen. Microbiol.* 135: 11(1989), and the Chey gene (EP Patent Pub. No. 324 647) genes. The DNA sequence at the junction of the two amino acid sequences may or may not encode a clearable site. Another example is a ubiquitin fusion protein. Such a fusion protein is made with the ubiquitin region that preferably retains a site for a processing enzyme (e.g., ubiquitin specific processing-protease) to cleave the ubiquitin from the polypeptide. Through this method, mature Towne or Toledo polypeptides can be isolated. See Miller, *Bio/Technology* 27:698(1989).

Alternatively, proteins or polypeptides can also be secreted from the cell by creating chimeric DNA molecules that encode a fusion protein comprised of a signal peptide sequence fragment that provides for secretion of the proteins or polypeptides in bacteria. (See, for example, U.S. Pat. No. 4,336,336). The signal sequence fragment typically encodes a signal peptide comprised of hydrophobic amino acids which direct the secretion of the protein from the cell. The protein is either secreted into the growth media (gram-positive bacteria) or into the periplasmic space, located between the inner and outer membrane of the cell (gram-negative bacteria). Preferably there are processing sites, which can be cleaved either in vivo or in vitro encoded between the signal peptide fragment and the protein or polypeptide.

DNA encoding suitable signal sequences can be derived from genes for secreted bacterial proteins, such as the *E. coli* outer membrane protein gene (ompA) (Masui, Experimental Manipulation of Gene Expression (1983) and Ghrayeb, *EMBO J.* 3:2437(1984)) and the *E. coli* alkaline phosphatase signal sequence (pho) (see Oka, *Proc. Natl. Acad. Sci.* 82:7212(1985). The signal sequence of the alpha-amylase gene from various Bacilus strains can be used to secrete heterologous proteins from *B. subtilis* (see Palva, *Proc. Natl. Acad. Sci.* 79:5582(1982) and EP Patent Pub. No. 244 042).

Transcription termination sequences recognized by bacteria are regulatory regions located 3' to the translation stop codon. Together with the promoter they flank the coding sequence. These sequences direct the transcription of an mRNA which can be translated into the Towne or Toledo protein or polypeptide encoded by the DNA sequence. Transcription termination sequences frequently include DNA sequences of about 50 nucleotides capable of forming stem loop structures that aid in terminating transcription. Examples include transcription termination sequences derived from genes with strong promoters, such as the trp gene in *E. coli* as well as other biosynthetic genes.

Typically, the promoter, signal sequence (if desired), coding sequence of interest, and transcription termination sequence are maintained in an extrachromosomal element (e.g., a plasmid) capable of stable maintenance in the bacterial host. The plasmid will have a replication system, thus allowing it to be maintained in the bacterial host either for expression or for cloning and amplification. In addition, the plasmid can be either a high or low copy number plasmid. A high copy number plasmid will generally have a copy number ranging from about 5 to about 200, and typically about 10 to about 150. A host containing a high copy number plasmid will preferably contain at least about 10, and more preferably at least about 20 plasmids.

Alternatively, the expression constructs can be integrated into the bacterial genome with an integrating vector. Integrating vectors typically contain at least one sequence homologous to the bacterial chromosome that allows the vector to integrate. Integrations appear to result from recombinations between homologous DNA in the vector and the bacterial chromosome. See e.g., EP Patent Pub. No. 127 328.

Typically, extrachromosomal and integrating expression constructs can contain selectable markers to allow for the selection of bacterial strains that have been transformed. Selectable markers can be expressed in the bacterial host and can include genes which render bacteria resistant to drugs such as ampicillin, chloramphenicol, erythromycin, kanamycin (neomycin), and tetracycline (see Davies, *Ann. Rev. Microbiol.* 32:469(1978). Selectable markers can also include biosynthetic genes, such as those in the histidine, tryptophan, and leucine biosynthetic pathways.

Alternatively, some of the above described components can be put together in transformation vectors. Transformation vectors are typically comprised of a selectable marker that is either maintained in an extrachromosal vector or an integrating vector, as described above.

Expression and transformation vectors, either extrachromosomal or integrating, have been developed for transformation into many bacteria. Exemplary are the expression vectors disclosed in Palva, *Proc. Natl. Acad. Sci.* 79:5582 (1982), EP Patent Pub. Nos. 036 259 and 063 953 and PCT Patent Publication WO 84/04541 (for *B.subtilis*); in Shimatake, *Nature* 2922:128(1981), Amann, *Gene* 40:183 (1985), Studier, *J. Mol. Biol.* 189:113(1986) and EP Patent Pub. Nos. 036 776, 136 829 and 136 907 (for *E. coli*); in Powell, *Appl. Environ. Microbiol.* 54:655(1988) and U.S. Pat. No. 4,745,056 (for Streptococcus).

Methods of introducing exogenous DNA into bacterial hosts are well-known in the art, and typically include either the transformation of bacteria treated with $CaCl_2$ or other agents, such as divalent cations and DMSO. DNA can also be introduced into bacterial cells by electroporation. Exemplary methodologies can be found in Masson, *FEMS Microbiol. Let.* 60:273(1989), Palva, *Proc. Natl. Acad. Sci.* 79:5582(1982), EP Patent Pub. Nos. 036 259 and 063 953 and PCT Patent Pub. WO 84/04541 for Bacillus transformation. For campylobacter transformation, see e.g., Miller, *Proc. Natl. Acad. Sci.* 85:856(1988) and Wang, *J. Bacteriol.* 172:949(1990). For *E. coli*, see e.g., Cohen, *Proc. Natl. Acad. Sci.* 69:2110(1973), Dower, *Nuc. Acids Res.* 16:6127 (1988), Kushner, *Genetic Engineering: Proceedings of the International Symposium on Genetic Engineering* (eds. H. W. Boyer and S. Nicosia), Mandel, *J. Mol. Biol.* 53:159 (1970) and Taketo, *Biochem. Biophys. Acta* 949:318(1988). For Lactobacillus and Pseudomonas, see e.g., Chassy, *FEMS Microbiol. Let.* 44:173(1987) and Fiedler, *Anal. Biochem.* 170: 38(1988), respectively. For Streptococcus, see e.g., Augustin, *FEMS Microbiol. Let.* 66:203(1990), Barany, *J. Bacteriol.* 144:698(1980), Harlander, *Streptococcal Genetics* (ed. J. Ferretti and R. Curtiss III)(1987), Perry, *Infec. Immun.* 32:1295(1981), Powell, *Appl. Environ. Microbiol.* 54:655(1988) and Somkuti, *Proc.* 4th Evr. Cong. Biotechnology 1:412(1987).

The present invention is illustrated by the following examples.

MATERIALS AND METHODS

A. Cells and virus

Human CMV strains AD169, Towne and Toledo were obtained from E.S. Mocarski (Stanford University) and were used for all experiments. Two of these strains are also available through the ATCC, Accession Nos. VR-538 (AD169) and VR-977 (Towne). Virus was grown in cultures of human foreskin fibroblast (HF) cells with Dulbecco's modified Eagle's medium (DME) (JRH Biosciences, Lenexa, Kans.) as previously described in Spaete and Mocarski, *J. Virol* 56: 13543(1985), but supplemented with 10% fetal calf serum (FCS) (JRH Biosciences, Lenexa, Kans.), L-glutamine (2 mM), penicillin (100 units/ml), streptomycin (0.1 mg/ml) and pyruvate (1 mM). To prepare AD169, Towne and Toledo strain CMV DNAs by centrifugation to equilibrium on NaI gradients as previously described in Spaete and Mocarski, *J. Virol* 54:817–24(1985), roller bottles were infected with the CMV strains at a multiplicity of infection (MOI) of 0.001 plaque forming units (pfu)/cell to minimize the production of defective virus particles. The infected cells were refed at four days post infection with medium. At eight days post infection when the monolayer was well infected, cells were scraped into a 50 ml conical tube in 10 mls media per roller bottle and pelleted at 1000 revolutions per minute (rpm) for 10 minutes. Pellets were resuspended in 2.0 ml 0.01M Tris and 0.01 EDTA (TE) (pH 7.4) with 1% NP40, 1% deoxycholate and incubated on ice until all cellular nuclei were lysed when viewed under a microscope. Lysates were transferred to a 2059 tube (Falcon) and spun at 2600 rpm for 5 minutes at 4° C. Supernatants were transferred to another 2059 tube and RNAse (Worthington-DNase free) was added at 50 μg/ml followed immediately by Proteinase K (200 μmg/ml) and 1% sodium dodecyl sulfate (SDS). Supernatants were incubated in a 65° C. water bath for 60 minutes, brought to 16 ml with TE, pH 7.4, added to 24 mls of saturated NaI and 0.15 ml ethidium bromide (5 mg/ml). Samples were centrifuged to equilibrium at 55,000 rpm at 20° C. for 24 hours in a Beckman Ti70 rotor. Fractions containing the viral DNA were extracted with butanol equilibrated with TE with gentle rocking followed by centrifugation at 3,000 rpm for 10 min at 20° C. and further extracted 2 to 3 times with butanol to reduce volume. Samples were extracted with an equal volume of isoamyl alcohol equilibrated with TE, spun and re-extracted. DNA was dialyzed against three changes of TE with 1% phenol and 1M NaCl. The $OD_{260}$ and $OD_{280}$ were read to determine purity of the AD169, Toledo and Towne DNA.

Clinical isolates were obtained from M. Fiala (Rancho Mirage, Calif.), and S. Chou (Oregon Health Sciences University). Rapid isolation of HCMV infected cell vital DNA was carried out as previously described in Spaete and Frenkel, *Cell* 30:295–304(1982), except that DNA was not radiolabeled before purification. Briefly, infected cell monolayers (25 $cm^2$ flasks) were rinsed twice with phosphate-buffered saline (PBS) and lysed in a 1.0 ml solution of 0.1M NaCl, TE, pH 8.0, 0.05% SDS and 0.1 mg/ml Proteinase K. Lysates were incubated 2–24 hours at 37° C., extracted twice with 1 volume of phenol, 1 volume of chloroform followed by centrifugation at 2500 rpm for 5 minutes to separate phases. The aqueous phase was extracted twice with 1 volume of ether and the DNA was precipitated with 0.1 volume 3M NaAC and two volumes of ethanol or isopropanol. DNA was chilled, collected by centrifugation or spooled on a glass rod, dried and resuspended in TE.

B. Plasmid DNA

Plasmids pXbaI E, pXbaI T and pXbaI Q (Thomsen and Stinski, 1981), representing Towne strain map units 0.69 to 0.8, were obtained from M. Stinski (University of Iowa).

Clone 65 was derived by cloning a gel extracted BamHI digested Toledo DNA fragment into the BamHI site of plasmid, pGEM®–3Zf+ (Promega, Madison, Wis.). Briefly, five μg of Toledo DNA was digested with 40 units of BamHI and electrophoresed in a preparative 1% low-melting-point agarose gel for 490 volt hours in IX TAE buffer. Toledo DNA migrating at ca. 5 kilobase pairs (kbp) was excised and the agarose was digested with 2 units of β-agarase I (New England BioLabs, Beverly, Mass.). This DNA fragment was precipitated with 2 volumes of isopropanol, chilled to –20° C., spun in an Eppendorf centrifuge for 15 minutes, dried and resuspended in 50 μl TE. The gel extracted fragment was ligated to BamHI digested pGEM®–3Zf+ using T4 DNA ligase (New England BioLabs, Berverly, Mass.), and an aliquot of the ligation mixture was used to transform competent *Escherichia coli* XL-1 Blues (Stratagene, La Jolla, Calif.) by the calcium shock method (Mandel and Higa, 1970), or by electroporation using methods as written in the Pulse Controller Guide published by BioRad (Richmond, Calif.).

Cosmid 1 is a ca. 53 kbp partially digested HindIII fragment of Toledo DNA spanning 0.69 to 0.87 map units cloned into cosmid pHC79 (Holm and Collins, 1980) obtained from E.S. Mocarski (Stanford University). Subcloned from cosmid 1 were the following:

Clones 4 and C1300 were derived by cloning BamH1 digested fragments from Cosmid 1 cloned into a Bluescript M13+ plasmid vector. As such, these clones represent Toledo DNA sequence spanning portions of Cosmid 1.

Clone C23K was derived as a complete BamH1 digested fragment of Cosmid 1 DNA and circularized by ligation.

C. Preparation of radioactively labeled probes and hybridization.

Plasmid or viral DNA was radioactively labeled in vitro by nick translation (Rigby et al., 1977) with a kit (Boehringer Mannheim), and using [$\alpha^{32}$P]dCTP (Amersham Corp.). Hybridizations to immobilized CMV DNA were performed essentially as described by Spaete and Mocarski, *J. Virol* 54:817–24 (1985), but at 68° C. in a solution of 6×SSC (1×SSC is 0.15M NaCl plus 0.015M sodium citrate), 0.2% polyvinylpyrrolidone, 0.2% Ficoll, 0.2% bovine serum albumin, and 0.1% sodium dodecyl sulfate, with the amount of salmon sperm DNA being changed from 25 μg/ml to 100μg/ml and 30% formamide being reduced to 15%.

DNA was transferred to Hybond-N+ nylon transfer membranes (Amersham Corp.), after restriction enzyme digestion and electrophoresis in 1% agarose gels by standard techniques (Maniatis et al., 1982). DNA was cross-linked to the membrane with 120,000 microjoules/cm2 of UV irradiation using a UV Crosslinker 1000 (Hoefer Scientific Instruments, San Francisco, Calif). Membranes were prehybridized 1 hour at 68° C. in solution A (6×SSC, 0.2% polyvinylpyrrolidone, 0.2% Ficoll, 0.2% bovine serum albumin, 0.1% sodium dodecyl sulfate, 100 μg/ml salmon sperm DNA and 15% formamide), then nick-translated [$\alpha^{32}$P]-labeled probe in a solution containing 100 μg/ml salmon sperm DNA was denatured by boiling for five minutes, snap-cooled on ice, added to the membrane and allowed to hybridize overnight at 68° C. After hybridization, unannealed probe was removed by rinsing the membrane 3× with 2×SSC followed by reincubation in solution A lacking salmon sperm DNA at 68° C. for 15 minutes. The washing procedure was repeated, the blot was rinsed in a large volume of 2×SSC at room temperature, the membrane was air dried and autoradiographed using Kodak X-AR film.

D. Nucleotide sequence determination and analysis.

All nucleic acid sequences were determined by the dideoxynucleotide chain termination method (Sanger et al., 1977). A variety of templates were prepared for sequencing; they included single-stranded phage DNA, double-stranded plasmid and cosmid DNA, viral genomic DNA, and PCR products. Manual and automated sequencing (with an ABI 373A instrument) were employed. Both one-cycle and multi-cycle sequencing protocols were used. The sequence was determined for both strands. Ambiguous regions were corrected by additional sequencing after proofreading. The primers used for sequencing were synthesized on an ABI 392 instrument (Applied Biosystems). The contig and analysis of the sequence were performed using MacDNASIS (Hitachi). The homology searches were performed using the BLAST program through NCBI services.

Example 1

Identification of Novel Sequences in the Genomes of CMV Towne and Toledo Strain Isolates.

To determine the cross representation of DNA sequences in the Towne and Toledo strains of CMV, viral DNA from each strain was digested to completion with 3fibaI, ClaI, BamHI, BglII, EcoRI, and HindIII. After electrophoresis through a 1% agarose gel, the CMV DNAs were denatured in 0.2M NaCl/0.6M NaOH, neutralized in 0.6M NaC/1M Tris, pH 7.5, in situ, and the gel was soaked in 20×SSC for 30 minutes. Stereo blots were prepared by placing identically sized Hybond-N+ nylon membranes (Amersham Corp.), on either side of the gel and transferring the DNAs to the membranes in both directions using the capillary action of paper towels. After blotting overnight in 20×SSC, the membranes were washed in 2×SSC and the DNA was immobilized on the membrane by UV irradiation as described above.

DNA probes of Towne and Toledo DNA with an average size of 500 bp were prepared by sonicating 10 μg of each DNA in a 2063 tube (Falcon Plastics) using 4 pulses of 10 seconds each at a setting of 3 on a Heat Systems, Inc. sonicator (Farmingdale, N.Y.). Following sonication, the viral DNAs were digested with the restriction enzymes AvaI, BanI and BfaI, to further reduce the size complexity of the probe DNA. These enzymes were chosen because a search of the AD 169 DNA database sequences (EMBL accession number X17403), revealed abundant cut sites (326, 386, and 341, respectively); their restriction enzyme digestion buffers are compatible; and their sites do not overlap. Ethidium bromide stained gels of the sheared viral DNAs prepared in this manner revealed a range of DNA sizes from 1300 bp to less than 100 bp, with the majority of DNA migrating at approximately 300 bp as judged by comigration with a HaeIII digested ØX174 DNA standard marker (New England BioLabs, Beverly, Mass). The Towne and Toledo sheared probe DNA was then nick translated using [$\alpha^{32}$P] dCTP (Amersham Corp.) as described above and each probe was applied to stereo blots of immobilized, restriction enzyme digested, Towne and Toledo DNAs. After hybridization and autoradiography, the hybridization patterns were analyzed to determine the fragments on each DNA profile which did not hybridize with the heterologous strain probe but did hybridize with the homologous strain probe. For example, the loss of a signal for a prominent 5 kbp band on the BamHI digest of Toledo DNA when using the Towne probe, which was present when the Toledo DNA was used to probe itself, revealed a region of sequence divergence between the two isolates (see FIG. 3).

This 5 kbp fragment was cloned by gel extraction as described above and designated clone 65. The clone 65 Toledo DNA was sequenced in its entirety and compared to Towne DNA sequence generated from the pXbaI T clone which was shown to be divergent from AD169 DNA sequences (see Example 2 below). The full sequence of clone 65 is shown in FIG. 1. In FIG. 1, Clone 65 begins with nucleotide 4664 and ends with nucleotide 9327. Surprisingly, the DNA from the pXbaI T clone of Towne DNA (1,856 bp) and clone 65 of Toledo DNA (4,668 bp) shared 104 bp of sequence identity. This small stretch of sequence homology allowed mapping of the region of Toledo DNA divergence to the boundary of the Unique Long (UD component and the inverted repeats (alternatively termed IRL or b' sequences) on the AD169 and Towne DNA maps. These newly isolated Toledo strain nucleotide sequences from clone 65 were not represented in the reference laboratory strain, AD169, which has been sequenced in its entirety by Chee and colleagues (EMBL accession number X17403).

Example 2

Identification of Novel Sequences in the Genome of CMV Towne Not Found in Reference Strain AD169.

DNA sequence heterogeneity between the Towne strain and the AD169 strain has been found. See, Pritchett, *J. Virology* 36:152–61 (1980). However, although the gross structural organization of the CMV genome has been determined and strain to strain restriction site polymorphisms have been mapped for many strains, strain-to-strain differences on the nucleotide level have not been determined. The laboratory strain AD169 was the first CMV isolate to be sequenced and has served as the reference strain in defining the genetic complexity of the CMV genome.

In order to examine nucleotide sequence differences between Towne and AD169, we focused on the region shown to be divergent in the Toledo strain, i.e. the boundary between the $U_L$ component and the b' sequences, as explained in detail in Example 1. Plasmid pXbaI T was labeled using the NEBlot™Phototope™Detection Kit (New England Biolabs, Beverly, Mass.), and used as a probe on blots of immobilized restriction enzyme digested Towne, Toledo and AD169 DNAs. Briefly, pXbaI T was linearized with PvuII, ethanol precipitated and resuspended in 34 μl of nuclease free water. The plasmid was denatured in boiling water for five minutes, snap cooled on ice for five minutes and centrifuged briefly at 4° C. The following reagents were added to the tube in the order listed: 10 μl of 5× labeling mix, 5 μl of dNTP mix, 1 μl of DNA polymerase I (Klenow fragment). The mix was incubated at 37° C. for 6 hours and the reaction was terminated by adding 5 μl of 0.2M EDTA, pH 8.0. The probe was precipitated by adding 5 μl of 4M LiCl and 150 μl of ethanol, chilling to −80° C. for 30 minutes, pelleted in an Eppendorf centrifuge, washed with 70% ethanol and resuspended in 20 μl of Resuspension Buffer as supplied by the kit. The hybridization reaction was essentially as described above except that after hybridization the membrane was washed twice in 2×SSC, 0.1% SDS at room temperature for 5 minutes each followed by two washes in 0.1×SSC, 0.1% SDS at 68° C. for 15 minutes. The detection reactions link the biotinylated probes to alkaline phosphatase through a strepavidin bridge and the hybridized probe was visualized by cleavage of the Lumigen-PPD substrate. The blocking steps, strepavidin incubation, alkaline phosphatase incubation and Lumigen-PPD reaction were carried out as described in the kit manual. Exposure of the blots to Kodak XAR film revealed that, as expected, (i) an XbaI digested fragment of sized 1.85 kbp (XbaI T) was hybridized on Towne DNA probed with pXbaI T and (ii) a comigrating XbaI digested fragment was present in Toledo DNA. The AD169 DNA failed to show any hybridization signal on any of the restriction enzyme digestion patterns. Nucleotide sequence of pXbaI T confirmed the total lack of identity of the Towne DNA and AD169 DNA. Nucleotide sequencing of cosmid 1 DNA (see B. Plasmid DNA in Material and Methods, above) from Toledo revealed extensive sequence identity between the newly identified Towne DNA and the Toledo DNA of cosmid 1 in this region. Surprisingly, the orientation of the sequence was reversed in Toledo relative to Towne.

Example 3

Identification of Novel Toledo DNA Sequences in the Genomes of Recent Clinical Isolates and not Found in Reference Strain ADI69.

To determine the penetrance of sequences represented by clone 65 in recent clinical isolates, five representative clinical isolates (HCMVF, C128, C354, C793 and C980) were digested with restriction enzymes BamHI and XbaI along with the Toledo, Towne and AD169 DNAs prepared as described in the Materials and Methods section above, electrophoresed through agarose, transferred to a Hybond-N+ nylon transfer membrane, and probed with nick-translated [$\alpha^{32}$P]-labeled clone 65 according to the procedures outlined in the Materials and Methods section. As can be seen in FIG. 4, the autoradiographs revealed that homology was detected in all of the clinical isolates. In FIG. 4, a band at ca. 5 kbp is visible in lane 1 (the Toledo DNA), appears in Towne DNA (lane 2), is missing from lane 3 (the AD 169 DNA), and visible in lanes 4 through 8 (the clinical isolates HCMVF, C128, C354, C793 and C980). These results demonstrate that the newly isolated sequence found in the Toledo strain of HCMV is also present in the recent clinical isolates but is not present in the AD169 reference strain. Nucleotide sequence analysis reveals the reason for the weak hybridization signal to the Towne DNA fragment is due to the existence of only 151 nucleotides of sequence identity with Towne DNA. The shared 104 bp sequence identity in Example 1 is responsible for a weak hybridization signal to XbaI "T" sized fragments from both Towne and Toledo DNAs seen in the XbaI digests (lanes 9 and 10). The XbaI digest of the clinical isolates (lanes 12 through 16) also reveals hybridization to multiple high molecular weight bands. Analysis of these and other clinical isolate genomes with other probes in the region has revealed that the shared sequences may be in inverted orientation in some isolates relative to the orientation in the Toledo strain.

FIG. 6 is a schematic illustration of the relative positions of novel sequences identified in Toledo genomic DNA, Towne genomic DNA in a comparison with AD169 strain genomic DNA. The dashed lines delimit the region of the genome where homologous and divergent sequences are found. The top line illustrates a Toledo DNA restriction map showing BamHI (indicated by "B") and XbaI (indicated by "X") restriction enzyme sites extending between the homology breakpoints identified by inverted triangles at nucleotides 175068 and 188843 (numbered with reference to the AD169 DNA sequence—EMBL accession number X17403). Subclones 4, 1300, C23K and 65 of the Toledo DNA sequence are shown in boxes above the map. An inverted region of homology with respect to Towne is shown by the inverted triangles between nucleotides 178221 and 175082. Unique sequences are shown by a thin line, and inverted repeat sequences denoted by thick lines, b'a'c'. The end of the c' repeats is shown with an arrow at nucleotide 191412. The middle line illustrates a Towne DNA restriction map showing BamHI (B) and XbaI (X) restriction enzyme sites as described above for Toledo and showing XbaI clones E, T, and Q in boxes below. Shaded area refers to homologous regions shared with Toledo DNA but inverted in orientation. Nucleotide numbers shown are with reference to the AD169 DNA sequence. Undetermined extent of b' repeat sequences in the Towne strain is shown by thin lines at AD169 strain nucleotide reference 180034. The bottom line illustrates the AD169 genome displayed in the prototype orientation. Unique sequences are displayed by a thin line, and inverted repeats of the long ($U_L$) and short ($U_S$) components are denoted by boxes, ab–b'a', and a'c'–ca. The a sequence, is a terminal direct repeat with an inverted copy (a'), at the junction of the long and short components. The length of the AD169 DNA sequence is indicated as 229354 nucleotides and the map position of the internal repeats are shown with the nucleotide reference numbers and arrows.

Example 4

Open Reading Frame Analysis of the Novel Toledo and Towne DNA Sequences

The novel Toledo and Towne sequences encoded potential open reading frames (ORFs). Using an arbitrarily chosen parameter of 10 kiloDaltons as the minimum calculated protein molecular weight, a total of 36 ORFs were identified in the novel Toledo sequence and a total of 4ORFs were identified in the novel Towne sequence. The putative amino acid sequences of these ORFs are set forth in the sequence listing (SEQ ID NOS:2, 3, 4, 5, 7, 8, 9, 10, 11, 12, 13, 14, 15, 16, 17, 18, 19, 20, 21, 22, 23, 24, 25, 26, and 27). FIG. 5 shows the schematic presentation of these ORFs in the novel Toledo and Towne DNA sequences, together with previously reported AD169 ORFs of the corresponding region. Names were assigned for these ORFs starting from UL133 as the first ORF at the left side of the UL in Toledo sequence. The first ORF in the novel Towne sequence was assigned as UL147, which was determined to be present in the novel Toledo sequence disclosed here. UL130 and UL132 in AD169 were determined to be present in the novel Toledo sequence. Additionally, UL153 and UL154 exhibited regions of homology to IRL14 and IRL12, respectively. All ORFs were searched for homologous sequence in the non-redundant databases of NCBI using the BLASTP program. Among all ORFs searched, only UL132 identified a homologue in the database, which was HCMV mtrIII (GenBank Accession No. X75606), exhibiting 76% identity at the amino acid level. The solid circle identified the ORFs that contained the potential N-linked glycosylation site sequence, N-X(-P)-S/T. These potential glycoproteins may be biologically significant as antigenic or immunogenic molecules.

The present investigation is not to be limited in scope by the specific embodiments described which are intended as single illustrations of individual aspects of the invention, and any constructs, viruses or enzymes which are functionally equivalent are within the scope of this invention. Indeed, various modifications of the invention in addition to those shown and described herein will become apparent to those skilled in the art from the foregoing description and accompanying drawings. Such modifications are intended to fall within the scope of the appended claims.

What is claimed is:

1. An isolated DNA sequence comprising the nucleotide sequence of SEQ ID NO:6, which encodes at least a part of a human cytomegalovirus.

2. An RNA molecule transcribed from said DNA sequence of claim 1.

3. A vector comprising said DNA sequence of claim 1.

4. A host cell transformed with said DNA sequence of claim 1, in operative association with an expression control sequence capable of directing replication and expression of said DNA sequence.

5. A method of producing a human cytomegalovirus protein comprising culturing said host cell of claim 4 in a suitable culture medium and isolating said protein from said medium.

* * * * *

SEQUENCE LISTING ( 1 ) GENERAL INFORMATION:

( i i i ) NUMBER OF SEQUENCES: 27

( 2 ) INFORMATION FOR SEQ ID NO:1:

( i ) SEQUENCE CHARACTERISTICS:
( A ) LENGTH: 4711 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO

-continued ( i v ) ANTI-SENSE: NO ( v i ) ORIGINAL SOURCE:
( A ) ORGANISM: Human CMV
( B ) STRAIN: Towne ( i x ) FEATURE:
( A ) NAME/KEY: CDS
( B ) LOCATION: complement (845..1321)
( D ) OTHER INFORMATION: /product="UL147"

( i x ) FEATURE:
( A ) NAME/KEY: CDS
( B ) LOCATION: complement (1368..1721)
( D ) OTHER INFORMATION: /product="UL152"

( i x ) FEATURE:
( A ) NAME/KEY: CDS
( B ) LOCATION: complement (2504..3337)
( D ) OTHER INFORMATION: /product="UL153"

( i x ) FEATURE:
( A ) NAME/KEY: CDS
( B ) LOCATION: complement (3515..4711)
( D ) OTHER INFORMATION: /product="UL154"

( x i ) SEQUENCE DESCRIPTION: SEQ ID NO:1:

ATCGGGCGCC AGAGCTAGAT CAGGCGTATC AAATTCCACT GCCAGGCGAC CTGATTCTAA 60

CGGTTCCACG ATCCGGGAGA GCGTTTCTAG ATATAGAGCA AAGCGTACCA CGTCTACCTG 120

CGGTGTAAAA AACTGTTGTG GGCGTTCACC GTCGTTGACC ACGTAAGCCA CGTAGAGGCC 180

AACATTTTCC ACCACGGGTT CTAGCTGCAG GCGGCACGTA AAGCTTAGAA ACGACGGCTG 240

TACGGTTTGG TTCCCGTGAA GCTGAAGCGT CACTTCCTTG CCGGGGCTCA CCGTGCTGTA 300

ACGCCGCACC GAGTCGGTCA TCTGCTCCAG ATCGGTAGAC CAGAAGGGCG TGCAATGCAT 360

ACTGTCCCAG TCGCGACACG CAGCCCAGCC TAGCTCGGTG AAGGGTCGAC GCACACCCGA 420

AAAAGTGTGC TTGAAGACCA GGGGGTCGCC TCGGTAGCTC AGTAGCCGAA CATGCACATA 480

GTCGCGGCTA CGTTGACAGA CGGCCCGTAG ACAGGCAGGA CAAGCGTGAA CAGCAAGCGC 540

AACATGCTGC GGGTTAGAAA ATGCGGCGTG CCGGCCACCG CCCGACTCAT AAACGCTACC 600

AGCATGACGT CTCAGATCAC ACAAGTGACG AGGAGCGTAC CGCAAATCAC TAGGGAAAAG 660

GCCAGCAGAG CCCGATAGTC TTGCTCTTCG CGAACGATCT CGTCCGGTTC CTCGCAGTCT 720

TCGTGGTCCA CAGAAGATGA GGAGCAGGAT TCTTCGTTAA TTTCTGCCAG GATACTAGTG 780

CTGTACCACA CCAGAGCGCT CAGCGTGCCC AGGGCTACCG CACGGTAAAA TAGGGACATG 840

ATCACCAGCG CAATCTGAAG TGGTGGTAGT TCAGTTTCTT GGCGTATTTC CAGAGAAAGG 900

CTTTGTAGGC CGTAGGGACT GGCCAGGCAC CGAACTCAAT ATTGGTAGAC ACTACGTCGT 960

AAATGCGTTG TTCCTCGTCT AAGATTAACC GAAAAAATAG CCGGTTGATG TGACGACGCA 1020

CGGCTTGCGC GTTAGGATTG AGACACTTGG TGCCCTTGTC CTTTAAAATA GCCAGCACTT 1080

CCTGACGATT GCAGCTTTCG CTCGCCGCGA TTGGCTTAAG CAATTCAGTT CCGATTGGCA 1140

GAGTATTCAA CAGAATTTGG TTGTTACAAC GACAGCGTTT GTCGTAATCT TCCAATTCTA 1200

AAAGATGGAC GGCTAGGGGA CATACGACAA ATAACATGTA TGCAGTCAAT TGCATATATC 1260

GTACCGATAA AATGTTAGTG TGCGGATTCA GAATCGGATG ATGCAACCGT CTTAGCATCA 1320

TATCGAAAAA GTATACATAT TACCGATTCA TTATAATTAG GGAATTATTT CCAACGCGGA 1380

CGTTTGTTAG TGACAGCGTT TTCTTCTACA TGCGGTCCAT TACTATCCTT TACTTTTACC 1440

AATACTCTGT GCCATGAGTT GTCTTTTTTA CCATCCAGCC ATTTGGACAA ATGATGATCG 1500

GGAGCTAAAC ATACAGGTTT ACCTCGAGGA GGCAATAGAT AATGTTGAGG TTTGTCACAC 1560

-continued

TCAGGAGGAT TGGGAGGGTC ACGACCAACC CAAAATAAGC CACCTATAGG ATGATGTAAA 1620

GCTTTGTGGG TACACGGACA ACGCAATTCT CTACTGTGAA CCCCATGGTA ATACATAAAT 1680

GCCATCAAAA GACTAATCAG CGAACCAAAA ATTAATCGCA TTCTAATTTT ATTAACTACG 1740

TCACTATCAG TAATTCGTAA TATCCGGTAT TCCCGGAAAA TCACTCAAAA CTGCGTCCAT 1800

GACACATCAA TTCCCGATAA GTACCCCCCT TTGAAATCGG ATCCCCCCAC ATACCAATCA 1860

ATCACACAAC ACACAGGTTT AAAAATCGAT CACACGTCAA TTAGGTTTCA AAATCGATAC 1920

TGTTTATTAT CAGGAATCTA GACTAATTCT ACAATGACAG CTCTGAATTT CTCTCTCGTC 1980

TTTCTTGTCA GGTTCTCATC ATCAATCTTC ACTTCCACCC ATCGAGGAGT CATCGTCGCT 2040

CCAAAACCCT TTGGGGTCGC TGGTTGGAAA AGTCTCTGAC ACGATCCAGG CACCCCGTAC 2100

CCAGTCCGAC TGATCTAGCT TACGGAGCAT CTCAACAGGC ATGAGCTGCA GGGCCACGGC 2160

TGTCACGGCA GGGATTATTA CTACCGTTCA GGTAAACTGT ATCTCCCTGA GTTACCGTGA 2220

TGGGTCTTTC TACATGTTGA CTTTGCGTAA AAAATCGCCG GTAAAATGTT TTTTCTTGTT 2280

CATGTAAAAG TACCGGAACT AAAATGCTAG TTAGAATGGT TGCAGTTGCT ATTAGCGCGG 2340

CTAGTAACAG TAGTTTAGTG TTACATTGTA TACCCATGTT TTTAATAACT ATGAATATTC 2400

TGCTTCACAC CATAAGTGCT TAACCCACAA AAACCACACG GAGACATTAT TGGCTAAAAA 2460

TAAAAACAAA AGTTTATTGA TGTGCATGTT AGGTTTTAGT CTAAAATTCA TCTGGGTCGT 2520

ATTTGGGAAG TTTTGTATAA CGCGGTCTTC TGGGGACGCG ACGGCTACCC ATGTATAAGG 2580

CTATAAGTGC CACAGATACC ACTATACCCG CCCATACAGC ATGAATTCCC AGGGGAATGT 2640

TAGTGTTTTT TACAGTTTTT ATTACATTGT CCCACGTTCT GCTATTATGC TGGTCTGATT 2700

CCTCTTTTGT TTTACATTTA TCAGGTATAG GAGACGATGT TGCAGTTCCT GATAACACGG 2760

TTAAATAGTA GTTTTCCTTT TTACCGTCAC TGTAACGTTG CAAAACGTAT TTTCCAGCGT 2820

GTTCGGTAGT TACGTTGTAT ATAGTGAGAG AGGTCTTATT GCAGTCTAAA CACATGCCGT 2880

TCAGTGGGGA AGTTGAATAA TAATGTCCAA TGCTGCACAG TTGGTGTGCG CGAGGTCCAT 2940

ATTTTATCCA TTCTATATCG TGCCATACAT CCGTTCTACT GCAGTTTTTC AAAGTGACGT 3000

ATCCACCGAC ATATCCTGTT ACATTAATTA CTTCGTAATT TAAATTAGAG TGTTTATAAA 3060

CGGTGTACAA ACTGCCATTG CAAGTTATGT TGCTGGTATT CAACCAGGGA GTAGTACTAT 3120

GAATGGTAGA AAACGTTAAT GTTGGCGTAG CGCTTGACGA TGATTTTGAA AGCGTTGAAG 3180

TGGTTGCTGA TGCGACTGAA GAAGCGGTAG AGGGTTTGTG CGTGGTTCCA TTTGCGATAG 3240

CTGAAGTGCT GTTAGCATCG GTGACAGAGT TAGAAGAATT TGTGATAGTG GAGGCGGTGG 3300

AGGTAAAGGC AATTGCACGG ACAGGAGCAC GTGTCATTGC AACCTTCAGA TATCGTAATC 3360

ATCAGTAACG TCCACTTAAC CGTAAATCTC CAGTCCATAA CGTTATTAAA TTTCGGTTAA 3420

CGGGCATTGA TGTTTCTTCG GACGTTGTTG ATCTTTCTTG CCCGTTTATT TTCTGATATG 3480

GTCTCATAAG ACATTTATCC GGAAACGTTG CTTAGTCCTC GTGCTCAGGA TTGTATCGAA 3540

CTATGAATTC TGATTCACTT ATATCGTCAC TTAATGGATG ATATTTTTTA TTTAGAGCTC 3600

GTCGGACGAA AAATAGGAGA ATGCAGGCTA CACAAATTAA TGCTAACGTC CACGTAGTGC 3660

GTCTGCCGTG TGATGTGTTA GAATGATTGT TATAGCGGTA TAAATGATCT ATAGATGATG 3720

TGGCTGTATT GTCTTCATAA TTGGTCGGTT TATGAGAAGT GTCCCATTCG TGCTTTGGTT 3780

CTTCACATAC CCAGGGATTC ACGTGTGTCC CGTTTGTGTT GTTTCTAGGA TGTATTTGCA 3840

GATTAAAGTT TTGATTTTGT TCGGAGGGAT GCCCAGTTTT ATAACATCGA AAGCTATATT 3900

TACCAGAATG AGTAAAATTA AGACCGTACA GAGATAAAGA TAAATTACGA TCGCATGTAA 3960

-continued

```
AACATAAATC ATAGTGATGT TTTAGATAAT TTGTGTGCCA CTCACATAGT ATACGCGAAT    4020
GGAGGATTTT CAATGAATGG TTATGATATT TTCCATTTCT TATGTTGGGA TGGGTGTATT    4080
TTCCGTGTGT GGATATATTA AAATGTCTAA GCCAGGCTGT TTTGTAGCAC GATGTGATGG    4140
TTAGGTTGTG TGTTATAGTA ATATTGTCTC CTTGTGCCGC CTCCAATAAT GTTTCAGATT    4200
CTTTTGATAT CGTATTATTT GTACTGTTAG GCGATGAGCA AGTTGGAAGC GGTGTAGTGA    4260
CGTTTTCATT TGCATTTATC ATAGTAGTAG TGTTGGTTGA TAATGATATA GTTTGCAAAG    4320
TCACAGTACT ATCGGTTACA TGCTGTGTCG ATGAATTCGT GTCGCCGTTT GGTGAAGTTG    4380
TTATTACAGT TACGTTAGTT GTAGATGTTT GGGTAGATAT GGTGGAAATA GTTGAGGTCA    4440
CGTCTGTGCC TTTTACAGAG CTTGCAGTGA ATCCTGTGGA TGTGTTGACG TTGCCATTGG    4500
AGGATGTGAA CATAGTGGTA GACATTTCGG TGGTTTGTAA CGTAGATGTC AGTTGTGTAG    4560
TAGATATTAA GCTTGTGGGT GTAATCGACG TGGAAGTATT GGCGATAGTG GTGTTGTTAC    4620
ACTTGCTTTT CTGCAGAATC CAAAAAATAA TAAACATGCA TATTATTTGC GTATATGATG    4680
ACTTGTTCCA CCGTCGATGT TGTGTGCGCA T                                   4711
```

( 2 ) INFORMATION FOR SEQ ID NO:2:

( i ) SEQUENCE CHARACTERISTICS:
( A ) LENGTH: 159 amino acids
( B ) TYPE: amino acid
( D ) TOPOLOGY: linear ( i i ) MOLECULE TYPE: protein ( x i ) SEQUENCE DESCRIPTION: SEQ ID NO:2:

```
Met Met Leu Arg Arg Leu His His Pro Ile Leu Asn Pro His Thr Asn
1               5                   10                  15

Ile Leu Ser Val Arg Tyr Met Gln Leu Thr Ala Tyr Met Leu Phe Val
            20                  25                  30

Val Cys Pro Leu Ala Val His Leu Leu Glu Leu Glu Asp Tyr Asp Lys
        35                  40                  45

Arg Cys Arg Cys Asn Asn Gln Ile Leu Leu Asn Thr Leu Pro Ile Gly
    50                  55                  60

Thr Glu Leu Leu Lys Pro Ile Ala Ala Ser Glu Ser Cys Asn Arg Gln
65                  70                  75                  80

Glu Val Leu Ala Ile Leu Lys Asp Lys Gly Thr Lys Cys Leu Asn Pro
                85                  90                  95

Asn Ala Gln Ala Val Arg Arg His Ile Asn Arg Leu Phe Phe Arg Leu
            100                 105                 110

Ile Leu Asp Glu Glu Gln Arg Ile Tyr Asp Val Val Ser Thr Asn Ile
        115                 120                 125

Glu Phe Gly Ala Trp Pro Val Pro Thr Ala Tyr Lys Ala Phe Leu Trp
    130                 135                 140

Lys Tyr Ala Lys Lys Leu Asn Tyr His His Phe Arg Leu Arg Trp
145                 150                 155
```

( 2 ) INFORMATION FOR SEQ ID NO:3:

( i ) SEQUENCE CHARACTERISTICS:
( A ) LENGTH: 118 amino acids
( B ) TYPE: amino acid
( D ) TOPOLOGY: linear ( i i ) MOLECULE TYPE: protein ( x i ) SEQUENCE DESCRIPTION: SEQ ID NO:3:

Met Arg Leu Ile Phe Gly Ser Leu Ile Ser Leu Leu Met Ala Phe Met
1 5 10 15

Tyr Tyr His Gly Val His Ser Arg Glu Leu Arg Cys Pro Cys Thr His
20 25 30

Lys Ala Leu His His Pro Ile Gly Gly Leu Phe Trp Val Gly Arg Asp
35 40 45

Pro Pro Asn Pro Pro Glu Cys Asp Lys Pro Gln His Tyr Leu Leu Pro
50 55 60

Pro Arg Gly Lys Pro Val Cys Leu Ala Pro Asp His His Leu Ser Lys
65 70 75 80

Trp Leu Asp Gly Lys Lys Asp Asn Ser Trp His Arg Val Leu Val Lys
85 90 95

Val Lys Asp Ser Asn Gly Pro His Val Glu Glu Asn Ala Val Thr Asn
100 105 110

Lys Arg Pro Arg Trp Lys
115

( 2 ) INFORMATION FOR SEQ ID NO:4:

( i ) SEQUENCE CHARACTERISTICS:
( A ) LENGTH: 278 amino acids
( B ) TYPE: amino acid
( D ) TOPOLOGY: linear ( i i ) MOLECULE TYPE: protein ( x i ) SEQUENCE DESCRIPTION: SEQ ID NO:4:

Met Thr Arg Ala Pro Val Arg Ala Ile Ala Phe Thr Ser Thr Ala Ser
1 5 10 15

Thr Ile Thr Asn Ser Ser Asn Ser Val Thr Asp Ala Asn Ser Thr Ser
20 25 30

Ala Ile Ala Asn Gly Thr Thr His Lys Pro Ser Thr Ala Ser Ser Val
35 40 45

Ala Ser Ala Thr Thr Ser Thr Leu Ser Lys Ser Ser Ser Ser Ala Thr
50 55 60

Pro Thr Leu Thr Phe Ser Thr Ile His Ser Thr Thr Pro Trp Leu Asn
65 70 75 80

Thr Ser Asn Ile Thr Cys Asn Gly Ser Leu Tyr Thr Val Tyr Lys His
85 90 95

Ser Asn Leu Asn Tyr Glu Val Ile Asn Val Thr Gly Tyr Val Gly Gly
100 105 110

Tyr Val Thr Leu Lys Asn Cys Ser Arg Thr Asp Val Trp His Asp Ile
115 120 125

Glu Trp Ile Lys Tyr Gly Pro Arg Ala His Gln Leu Cys Ser Ile Gly
130 135 140

His Tyr Tyr Ser Thr Ser Pro Leu Asn Gly Met Cys Leu Asp Cys Asn
145 150 155 160

Lys Thr Ser Leu Thr Ile Tyr Asn Val Thr Thr Glu His Ala Gly Lys
165 170 175

Tyr Val Leu Gln Arg Tyr Ser Asp Gly Lys Lys Glu Asn Tyr Tyr Leu
180 185 190

Thr Val Leu Ser Gly Thr Ala Thr Ser Ser Pro Ile Pro Asp Lys Cys
195 200 205

Lys Thr Lys Glu Glu Ser Asp Gln His Asn Ser Arg Thr Trp Asp Asn
210 215 220

Val Ile Lys Thr Val Lys Asn Thr Asn Ile Pro Leu Gly Ile His Ala

-continued 225 230 235 240

Val Trp Ala Gly Ile Val Val Ser Val Ala Leu Ile Ala Leu Tyr Met
245 250 255

Gly Ser Arg Arg Val Pro Arg Arg Pro Arg Tyr Thr Lys Leu Pro Lys
260 265 270

Tyr Asp Pro Asp Glu Phe
275

( 2 ) INFORMATION FOR SEQ ID NO:5:

( i ) SEQUENCE CHARACTERISTICS:
( A ) LENGTH: 399 amino acids
( B ) TYPE: amino acid
( D ) TOPOLOGY: linear ( i i ) MOLECULE TYPE: protein ( x i ) SEQUENCE DESCRIPTION: SEQ ID NO:5:

Met Arg Thr Gln His Arg Arg Trp Asn Lys Ser Ser Tyr Thr Gln Ile
1 5 10 15

Ile Cys Met Phe Ile Ile Phe Trp Ile Leu Gln Lys Ser Lys Cys Asn
20 25 30

Asn Thr Thr Ile Ala Asn Thr Ser Thr Ser Ile Thr Pro Thr Ser Leu
35 40 45

Ile Ser Thr Thr Gln Leu Thr Ser Thr Leu Gln Thr Thr Glu Met Ser
50 55 60

Thr Thr Met Phe Thr Ser Ser Asn Gly Asn Val Asn Thr Ser Thr Gly
65 70 75 80

Phe Thr Ala Ser Ser Val Lys Gly Thr Asp Val Thr Ser Thr Ile Ser
85 90 95

Thr Ile Ser Thr Gln Thr Ser Thr Thr Asn Val Thr Val Ile Thr Thr
100 105 110

Ser Pro Asn Gly Asp Thr Asn Ser Ser Thr Gln His Val Thr Asp Ser
115 120 125

Thr Val Thr Leu Gln Thr Ile Ser Leu Ser Thr Asn Thr Thr Thr Met
130 135 140

Ile Asn Ala Asn Glu Asn Val Thr Thr Pro Leu Pro Thr Cys Ser Ser
145 150 155 160

Pro Asn Ser Thr Asn Asn Thr Ile Ser Lys Glu Ser Glu Thr Leu Leu
165 170 175

Glu Ala Ala Gln Gly Asp Asn Ile Thr Ile Thr His Asn Leu Thr Ile
180 185 190

Thr Ser Cys Tyr Lys Thr Ala Trp Leu Arg His Phe Asn Ile Ser Thr
195 200 205

His Gly Lys Tyr Thr His Pro Asn Ile Arg Asn Gly Lys Tyr His Asn
210 215 220

His Ser Leu Lys Ile Leu His Ser Arg Ile Leu Cys Glu Trp His Thr
225 230 235 240

Asn Tyr Leu Lys His His Tyr Asp Leu Cys Phe Thr Cys Asp Arg Asn
245 250 255

Leu Ser Leu Ser Leu Tyr Gly Leu Asn Phe Thr His Ser Gly Lys Tyr
260 265 270

Ser Phe Arg Cys Tyr Lys Thr Gly His Pro Ser Glu Gln Asn Gln Asn
275 280 285

Phe Asn Leu Gln Ile His Pro Arg Asn Asn Thr Asn Gly Thr His Val
290 295 300

-continued

Asn Pro Trp Val Cys Glu Glu Pro Lys His Glu Trp Asp Thr Ser His
305 310 315 320

Lys Pro Thr Asn Tyr Glu Asp Asn Thr Ala Thr Ser Ser Ile Asp His
325 330 335

Leu Tyr Arg Tyr Asn Asn His Ser Asn Thr Ser His Gly Arg Arg Thr
340 345 350

Thr Trp Thr Leu Ala Leu Ile Cys Val Ala Cys Ile Leu Leu Phe Phe
355 360 365

Val Arg Arg Ala Leu Asn Lys Lys Tyr His Pro Leu Ser Asp Asp Ile
370 375 380

Ser Glu Ser Glu Phe Ile Val Arg Tyr Asn Pro Glu His Glu Asp
385 390 395

( 2 ) INFORMATION FOR SEQ ID NO:6:

( i ) SEQUENCE CHARACTERISTICS:
( A ) LENGTH: 18318 base pairs
( B ) TYPE: nucleic acid
( C ) STRANDEDNESS: double
( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
( A ) ORGANISM: Human CMV
( B ) STRAIN: Toledo ( i x ) FEATURE:
( A ) NAME/KEY: CDS
( B ) LOCATION: 511..1281
( D ) OTHER INFORMATION: /product ="UL133"

( i x ) FEATURE:
( A ) NAME/KEY: CDS
( B ) LOCATION: 1401..2384
( D ) OTHER INFORMATION: /product ="UL135"

( i x ) FEATURE:
( A ) NAME/KEY: CDS
( B ) LOCATION: 2478..3197
( D ) OTHER INFORMATION: /product ="UL136"

( i x ) FEATURE:
( A ) NAME/KEY: CDS
( B ) LOCATION: 3283..3789
( D ) OTHER INFORMATION: /product ="UL138"

( i x ) FEATURE:
( A ) NAME/KEY: CDS
( B ) LOCATION: 4355..4759
( D ) OTHER INFORMATION: /product ="UL139"

( i x ) FEATURE:
( A ) NAME/KEY: CDS
( B ) LOCATION: 4944..5285
( D ) OTHER INFORMATION: /product ="UL140"

( i x ) FEATURE:
( A ) NAME/KEY: CDS
( B ) LOCATION: 5558..6832
( D ) OTHER INFORMATION: /product ="UL141"

( i x ) FEATURE:
( A ) NAME/KEY: CDS
( B ) LOCATION: 6908..7825
( D ) OTHER INFORMATION: /product ="UL142"

( i x ) FEATURE:
( A ) NAME/KEY: CDS
( B ) LOCATION: 7813..8088

( D ) OTHER INFORMATION: /product ="UL143"

( i x ) FEATURE:
( A ) NAME/KEY: CDS
( B ) LOCATION: 8468..8995
( D ) OTHER INFORMATION: /product ="UL144"

( i x ) FEATURE:
( A ) NAME/KEY: CDS
( B ) LOCATION: 9327..9626
( D ) OTHER INFORMATION: /product ="UL145"

( i x ) FEATURE:
( A ) NAME/KEY: CDS
( B ) LOCATION: 9910..10260
( D ) OTHER INFORMATION: /product ="UL146"

( i x ) FEATURE:
( A ) NAME/KEY: CDS
( B ) LOCATION: 10328..10804
( D ) OTHER INFORMATION: /product ="UL147"

( i x ) FEATURE:
( A ) NAME/KEY: CDS
( B ) LOCATION: 11106..12053
( D ) OTHER INFORMATION: /product ="UL148"

( i x ) FEATURE:
( A ) NAME/KEY: CDS
( B ) LOCATION: 12133..12942
( D ) OTHER INFORMATION: /product ="UL132"

( i x ) FEATURE:
( A ) NAME/KEY: CDS
( B ) LOCATION: 13569..14210
( D ) OTHER INFORMATION: /product ="UL130"

( i x ) FEATURE:
( A ) NAME/KEY: CDS
( B ) LOCATION: 16216..16581
( D ) OTHER INFORMATION: /product ="UL149"

( i x ) FEATURE:
( A ) NAME/KEY: CDS
( B ) LOCATION: 1004..1528
( D ) OTHER INFORMATION: /product ="UL134"

( i x ) FEATURE:
( A ) NAME/KEY: CDS
( B ) LOCATION: 3063..3350
( D ) OTHER INFORMATION: /product ="UL137"

( i x ) FEATURE:
( A ) NAME/KEY: CDS
( B ) LOCATION: 16337..18262
( D ) OTHER INFORMATION: /product ="UL150"

( i x ) FEATURE:
( A ) NAME/KEY: CDS
( B ) LOCATION: 17752..18759
( D ) OTHER INFORMATION: /product ="UL151"

( x i ) SEQUENCE DESCRIPTION: SEQ ID NO:6:

```
CGCTGTAGGG ATAAATAGTG CGATGGCGTT TGTGGGAGAA CGCAGTAGCG ATGGGTTGCG    60
ACGTGCACGA TCCTTCGTGG CAATGCCAAT GGGGCGTTCC CACGATTATC GTGGCCTGGA   120
TAACATGCGC GGCTTTAGGA ATTTGGTGTT TGGCGGGATC GTCGGCGGAT GTCTCTTCGG   180
GACCCGGCAT CGCAGCCGTA GTCGGCTGTT CTGTTTTCAT GATTTTCCTC TGCGCGTATC   240
TCATCCGTTA CCGGGAATTC TTCAAAGACT CCGTAATCGA CCTCCTTACC TGCCGATGGG   300
TTCGCTACTG CAGCTGCAGC TGTAAGTGCA GCTGCAAATG CATCTCGGGC CCCTGTAGCC   360
GCTGCTGTTC AGCGTGTTAC AAGGAGACGA TGATTTACGA CATGGTCCAA TACGGTCATC   420
GACGGCGTCC CGGACACGGC GACGATCCCG ACAGGGTGAT CTGCGAGATA GTCGAGAGTC   480
```

-continued

CCCCGGTTTC GGCGCCGACG GTGTCCGTCC CCCCGCCGTC GGAGGAGTCC CACCAGCCCG 540

TCATCCCACC GCAGCCGCCA GCACCGACAT CGGAACCCAA ACCGAAGAAA GGTAGGGCGA 600

AAGATAAACC GAAGGGTAGA CCGAAAGACA AACCTCCGTG CGAACCGACG GTGAGTTCAC 660

AACCACCGTC GCAGCCGACG GCAATGCCCG GCGGTCCGCC CGACGCGCCT CCCCCCGCCA 720

TGCCGCAGAT GCCACCCGGC GTGGCCGAGG CGGTACAAGC TGCCGTGCAG GCGGCCGTGG 780

CCGCGGCTCT ACAACAACAG CAGCAGCATC AGACCGGAAC GTAACCCGCC CCCGGTGCGA 840

TAAGGAATTT TCCGACTTGG CGCACATCTC CTTCCTCAAT GTTTGGACAA TAAACACATT 900

CCTTGCCAAA AAATGACGTT TCCAGAAATC CAAGGCATAA ATGTCCGTAC ACCGGCCCTT 960

CCCAACACGG AGTTTGAGAT TCCAAGCAGG AGAGAAGATC ATGGTGTGGA TATGGCTCGG 1020

CATCGGGCTC CTCGGCGGTA CCGGACTGGC TTCCCTGGTC CTGGCCATTT CCTTATTTAC 1080

CCAGCGCCGA GGCCGCAAGC GATCCGACGA GACTTCGTCG CGAGGCCGGC TCCCGGGTGC 1140

TGCTTCTGAT AAGCGTGGTG CCTGCGCGTG CTGCTATCGA AATCCGAAAG AAGACGTCGT 1200

CGAGCCGCTG GATCTGGAAC TGGGGCTCAT GCGGGTGGAC ACCCACCCGC CGACGCCGCA 1260

GGTGCCGCGG TGTACGTCGC TCTACATAGG AGAGGATGGT CTGCCGATAG ATAAACCCGA 1320

GTTTCCTCCG GCGCGGTTCG AGATCCCCGA CGTATCCACG CCGGGAACGC CGACCAGCAT 1380

CGGCCGATCT CCGTCGCATT GCTCCTCGTC GAGCTCTTTG TCGTCCTCGA CCAGCGTCGA 1440

CACGGTGCTG TATCAGCCGC CGCCATCCTG GAAGCCACCT CCGCCGCCCG GGCGCAAGAA 1500

GCGGCCGCCT ACGCCGCCGG TCCGGGCCCC CACCACGCGG CTGTCGTCGC ACAGACCCCC 1560

GACGCCGATA CCCGCGCCGC GTAAGAACCT GAGCACGCCG CCCACCAAGA AAACGCCGCC 1620

GCCCACGAAA CCCAAGCCGG TCGGCTGGAC ACCGCCGGTG ACACCCAGGC CCTTCCCGAA 1680

AACGCCGACG CCACAAAAGC CGCCGCGGAA TCCGAGACTA CCGCGCACCG TCGGTCTGGA 1740

GAATCTCTCG AAGGTGGGAC TCTCGTGTCC CTGTCCCCGA CCCCGCACGC CGACGGAGCC 1800

GACCACGCTG CCTATCGTGT CGGTTTCCGA GCTAGCCCCG CCTCCTCGAT GGTCGGACAT 1860

CGAGGAACTC TTGGAACAGG CGGTGCAGAG CGTCATGAAG GACGCCGAGT CGATGCAGAT 1920

GACCTGAGAC CGAAAGAGCG AGCGCGTCCG TTGTACAGTT GTATAGCAGC ACACGCCTTC 1980

CCTCTTTTTC ACCGCAGCTA AGAGAGAGAA AGAGAGTATG TCAGTCAAGG GCGTGGAGAT 2040

GCCAGAAATG ACGTGGGACT TGGACGTTAG AAATAAATGG CGGCGTCGAA AGGCCCTGAG 2100

TCGCATTCAC CGGTTCTGGG AATGTCGGCT ACGGGTGTGG TGGCTGAGTG ACGCCGGCGT 2160

AAGAGAAACC GACCCACCGC GTCCCCGACG CCGCCCGACT TGGATGACCG CGGTGTTTCA 2220

CGTTATCTGT GCCGTTTTGC TTACGCTTAT GATTATGGCC ATCGGCGCGC TCATCGCGTA 2280

CTTAAGATAT TACCACCAGG ACAGTTGGCG AGACATGCTC CACGATCTAT TTTGCGGCTG 2340

TCATTATCCC GAGAAGTGCC GTCGGCACCA CGAGCGGCAG AGAAGGAGAC GGCAAGCCAT 2400

GGATGTGCCC GACCCGGAAC TCGGCGACCC GGCCCGCCGG CCGTTGAACG GAGCTATGTA 2460

CTACGGCAGC GGCTGTCGCT TCGACACGGT GGAAATGGTG GACGAGACGA GACCCGCGCC 2520

GCCGGCGCTG TCATCGCCCG AAACCGGCGA CGATAGCAAC GACGACGCGG TTGCCGGCGG 2580

AGGTGCTGGC GGGGTAACAT CACCCGCGAC TCGTACGACG TCGCCGAACG CACTGCTGCC 2640

AGAATGGATG GATGCGGTGC ATGTGGCGGT CCAAGCCGCC GTTCAAGCGA CCGTGCAAGT 2700

AAGTGGCCCG CGGGAGAACG CCGTATCTCC CGCTACGTAA GAGGGTTGAG GGGGCCGTTC 2760

CCGCGCGAGT GCTGTACAAA AGAGAGAGAC TGGGACGTAG ATCCGGACAG AGGACGGTCA 2820

CCATGGACGA TCTGCCGCTG AATGTCGGGT TACCCATCAT CGGCGTGATG CTCGTGCTGA 2880

-continued

```
TCGTGGCCAT CCTCTGCTAT CTGGCTTACC ACTGGCACGA CACCTTCAAA CTGGTGCGCA 2940
TGTTTCTGAG CTACCGCTGG CTGATCCGCT GTTGCGAGCT GTACGGGGAG TACGAGCGCC 3000
GGTTCGCGGA CCTGTCGTCT CTGGGCCTCG GCGCCGTACG GCGGGAGTCG GACAGACGAT 3060
ACCGTTTCTC CGAACGGCCC GACGAGATCT TGGTCCGTTG GGAGGAAGTG TCTTCCCAGT 3120
GCAGCTACGC GTCGTCGCGG ATAACAGACC GCCGTGTGGG TTCATCGTCT TCGTCGTCGG 3180
TCCACGTCGC TAGCCAGAGA AACAGCGTGC CTCCGCCGGA CATGGCGGTG ACGGCGCCGC 3240
TGACCGACGT CGATCTGTTG AAACCCGTGA CGGGATCCGC GACGCAGTTC ACCACCGTAG 3300
CCATGGTACA TTATCATCAA GAGTACACGT GAATGAGAAA AAGAAAAAAG AGGGGAGCGG 3360
ATCGCGATAA TGTCGCTTTG ACATTCTCTG CTCGATCTAC TCAGCGTCTG CACGAAACGG 3420
CATCCGCACG GAGGCGAGCC CAAGCGTATC TGCAGCAAGC GGTTCTTTCC CTCGGTGATG 3480
GTGGCAGCAT CGGTGGCGGG AGCTTGTTCG GACGATGGAC GGTGAGGAGT CCCTGGCGAT 3540
CAGGCGGCTC CCGGGTGTGG AGTTCAACGG GTGGTAATGG TGGCGGTGAT CGGTGTTAGA 3600
AAACGGTGGC CCTGGCAAAC ATATATCTAC TGTAAACCCT CTGCTCTGTT AATAAAAAGC 3660
ACACTTTTCA CATGAGTTCG TAATTTTATT GTGTAGTGGA AATTTTTACG TCATTGGGAA 3720
ACCCCAGAAT GAAAGAGTAT AATGTGCATA TCACCGGGGG TTCCCTGTCA GTACGAATGT 3780
ACACAACGCG GGTTACATTA CGATAAACTT TCCGGTAAAA CGATGCCGAT ACAGCGTGTA 3840
TAACGCTGAT TGTTACGACA AACGAGTTGG TATATCCATT ATATAGTAAC GAACATGCTG 3900
TGGATATTAG TTTTATTTGC ACTCGCCGCA TCGGCGAGTG AAACCACTAC AGGTACCAGC 3960
TCTAATTCCA GTCAATCTAC TAGTGCTACC GCCAACACGA CCGTATCGAC ATGTATTAAT 4020
GCCTCTAACG GCAGTAGCTG GACAGTACCA CAGCTCGCGC TGCTTGCCGC TAGCGGCTGG 4080
ACATTATCTG GACTCCTTCT CTTATTTACC TGCTGCTTTT GCTGCTTTTG GCTAGTACGT 4140
AAAATCTGCA GCTGCTGCGG CAACTCCTCC GAGTCAGAGA GCAAAACAAC CCACGCGTAC 4200
ACCAATGCCG CATTCACTTC TTCCGACGCA ACGTTACCCA TGGGCACTAC AGGGTCGTAC 4260
ACTCCCCCAC AGGACGGCTC ATTTCCACCT CCGCCTCGGT GACGTAGGCT AAACCGAAAC 4320
CCACGTTGAA CCTAACGCGG TTTCGGAAGG CCTGAGACGT CACTTTCACA ATGACGTCCG 4380
TATACACGTT CATCATAAAA CACCGTAGAG GCTAAGGCTT CGGTAGGGAG AGACCTCAAC 4440
TGTTCCTGAT GAGCACCCGT GCTCTCATCT CTTCAGACTT GTCATGACCC CCGCTCAGAC 4500
TAACGCGACT ACCACCGTGC ACCCGCACGA CGCAAAAAAC GGCAGCGGCG GTAGTGCCCT 4560
GCCGACCCTC GTCGTTTTCG GCTTTATCGT TACGCTACTT TTCTTTCTCT TTATGCTCTA 4620
CTTTTGGAAC AACGACGTGT TCCGTAAGCT GCTCCGTGCG CTTGGATCCA GCGCTGTTGC 4680
GACCGCTTCG ACGCGTGGCA AGACGAGGTC ATCTACCGTC GTCCATCACG TCGTTCCCAG 4740
AGCGACGACG AGAGTCGTAC TAACAGCGTG TCATCGTACG TTCTTTTATC ACCCGCGTCC 4800
GATGGCGGTT TTGACAACCC GGCACTGACA GAGGCCGTCG ACAGCGTGGA CGACTGGGCG 4860
ACCACCTCGG TTTTCTACGC CACGTCCGAC GAAACGGCGG ACGCCGAGCG CCGAGACTCG 4920
CAGCAACTGC TCATCGAGCT TCCGCCGGAG CCGCTCCCGC CCGACGTGGT GGCGGCCATG 4980
CAGAAAGCAG TGAAACGCGC TGTACAGAAC GCACTACGAC ACAGCCACGA CTCTTGGCAG 5040
CTTCATCAGA CCCTGTGACG CCAGATGAAC GTTCCTTCTT AAACATCCGA GGTAGCAATG 5100
AGACAGGTCG CGTACCGCCG GCGACGCGAG AGTTCCTGCG CGGTGCTGGT CCACCACGTC 5160
GGCCGCGACG GCGACGGCGA GGGGGAGGCA GCAAAAAAGA CCTGCAAAAA AACCGGACGC 5220
TCAGTTGCGG GCATCCCGGG CGAGAAGCTG CGTCGCACGG TGGTCACCAC CACGCCGGCC 5280
```

-continued

CGACGTTTGA GCGGCCGACA CACGGAGCAG GAGCAGGCGG GCATGCGTCT CTGTGAAAAA 5340

GGGAAGAAAA GAATCATCAT GTGCCGCCGG GAGTCGCTCC GAACTCTGCC GTGGCTGTTC 5400

TGGGTGCTGT TGAGCTGCCC GCGACTCCTC GAATATTCTT CCTCTTCGTT CCCCTTCGCC 5460

ACCGCTGACA TTGCCGAAAA GATGTGGGCC GAGAATTATG AGACCACGTC GCCGGCGCCG 5520

GTGTTGGTCG CCGAGGGAGA GCAAGTTACC ATCCCCTGCA CGGTCATGAC ACACTCCTGG 5580

CCCATGGTCT CCATTCGCGC ACGTTTCTGT CGTTCCCACG ACGGCAGCGA CGAGCTCATC 5640

CTGGACGCCG TCAAAGGCCA TCGGCTGATG AACGGACTCC AGTACCGCCT GCCGTACGCC 5700

ACTTGGAATT TCTCGCAATT GCATCTCGGC CAAATATTCT CGCTTACTTT TAACGTATCG 5760

ATGGACACAG CCGGCATGTA CGAATGCGTG CTACGCAACT ACAGCCACGG CCTCATCATG 5820

CAACGCTTCG TAATTCTCAC GCAGCTGGAG ACGCTCAGCC GGCCCGACGA ACCTTGCTGC 5880

ACACCGGCGT TAGGTCGCTA CTCGCTGGGA GACCAGATCT GGTCGCCGAC GCCCTGGCGT 5940

CTACGGAATC ACGACTGCGG AACGTACCGC GGCTTTCAAC GCAACTACTT CTATATCGGC 6000

CGCGCCGACG CCGAGGATTG CTGGAAACCC GCATGTCCGG ACGAGGAACC CGACCGCTGT 6060

TGGACAGTGA TACAGCGTTA CCGGCTCCCC GGCGACTGCT ACCGTTCGCA GCCACACCCG 6120

CCGAAATTTT TACCGGTGAC GCCAGCACCG CCGGCCGACA TAGACACCGG GATGTCTCCC 6180

TGGGCCACTC GGGGAATCGC GGCGTTTTTG GGGTTTTGGA GTATTTTTAC CGTATGTTTC 6240

CTATGCTACC TGTGTTATCT GCAGTGTTGT GGACGCTGGT GTCCCACGCC GGGAAGGGGA 6300

CGACGAGGCG GTGAGGGCTA TCGACGCCTA CCGACTTACG ATAGTTACCC CGGTGTTAGA 6360

AAGATGAAGA GGTGAGAACA CGTATAAAAT AAAAAAATAA TATGTTAAAA AATGCAGTGT 6420

GTGAAGTGTG AATAGTGTGA TTAAAATATG CGGATTGAAT GGGTGTGGTG GTTATTCGGA 6480

TACTTTGTGT CATCCGTTGG GAGCGAACGG TCATTATCCT ATCGTTACCA CTTGGAATCT 6540

AATTCATCTA CCAACGTGGT TTGCAACGGA AACATTTCCG TGTTTGTAAA CGGCACCCTA 6600

GGTGTGCGGT ATAACATTAC GGTAGGAATC AGTTCGTCTT TATTAATAGG ACACCTTACT 6660

ATACAAGTAT TGGAATCATG GTTCACACCC TGGGTCCAAA ATAAAAGTTA CAACAAACAA 6720

CCCCTAGGTG ACACTGAAAC GCTTTATAAT ATAGATAGCG AAAACATTCA TCGCGTATCT 6780

CAATATTTTC ACACAAGATG GATAAAATCT CTGCAAGAGA ATCACACTTG CGACCTCACA 6840

AACAGTACAC CTACCTATAC ATATCAAGTA AACGTGAACA ACACGAATTA CCTAACACTA 6900

ACATCCTCGG GATGGCAAGA CCGTCTAAAT TACACCGTCA TAAATAGTAC ACACTTTAAC 6960

CTCACAGAAT CGAACATAAC CAGCATTCAA AAATATCTCA ACACTACCTG CATAGAAAGA 7020

CTCCGTAACT ACACCTTGGA GTCCGTATAC ACCACAACTG TGCCTCAAAA CATAACAACA 7080

TCTCAACACG CAACAACCAC TATGCACACA ATACCTCCAA ATACAATAAC AATTCAAAAT 7140

ACAACTCAAA GCCATACTGT ACAGACGCCG TCTTTTAACG ACACACATAA CGTGACGAAA 7200

CACACGTTAA ACATAAGCTA CGTTTTATCA CAAAAAACGA ATAACACAAC ATCACCGTGG 7260

ATATATGCCA TACCTATGGG CGCTACAGCC ACAATAGGCG CCGGTTTATA TATCGGGAAA 7320

CACTTTACGC CGGTTAAGTT CGTATACGAG GTATGGCGCG GTCAGTAAAG ACGATTCGGA 7380

TTCAACACAT ATACTCCCCA CGATCCTCGA ACACCTTACA GCATATGAGC AAAAAACAAG 7440

AAAGTATAGC CACAATCACA TTTGGGCGAA TAACATGCTG TCATCCACTA GCGTCTATTA 7500

ATCTAATGTT TAACGGGAGC TGTACTGTCA CCGTTAAAAT ATCCATGGGA ATCAACGGGT 7560

CAACCAACGT CCATCAGCTT GTGATTGTGC TCCATCTGGG TAACCGCTGT CAGCCTTGGC 7620

GACAGGTGTA ATCACAGCTG TCACATAACT CACGAAGCCT CCAATCACAG CAGCACACAT 7680

-continued

```
AGTCCTAACG CCATTGGCGT GTATAAAAGT TCGGAAAACT TGACGGTTGT ACGGCACGAC 7740
AAATCGATGT AGTGGTATGT TTTTCCAGCA GAGACCGTGT GCGGTCTCTT AGGTTCGCTA 7800
TACTGTGGCT GGAAACTGGT TACCTGTGAA GATGGCTAAC TATCCTGTTC TGTCCTGGAA 7860
AAACTTTTGG CGTCGTAGGT GGACTTTGCA GTATGCGGGT TAGTGAAGTT ATGTCATTTA 7920
TTTACGTTTA CGATCTCGTA TTACAAACCG CGGAGAGGAT GATACCGTTC GGCCCCATGA 7980
GTTATTTTTA TTCTTCCGGT AGGAGGCATG AAGCCTCTGA TAATGCTCAT CTGCTTTGCT 8040
GTGATATTAT TGCAGCTTGG AGTGACTAAA GTGTGTCAGC ATAATGAAGT GCAACTGGGC 8100
AATGAGTGCT GCCCTCCGTG TGGTTCGGGA CAAAGAGTTA CTAAAGTATG CACGGATTAT 8160
ACCAGTGTAA CGTGTACCCC TTGCCCCAAC GGCACGTATG TATCGGGACT TTACAACTGT 8220
ACCGATTGCA CTCAATGTAA CGTCACTCAG GTCATGATTC GTAACTGCAC TTCCACCAAT 8280
AATACCGTAT GCGCACCTAA GAACCATACG TACTTTTCCA CTCCAGGCGT CCAACATCAC 8340
AAACAACGAC AGCAAAATCA TACCGCACAT ATAACCGTCA AACAAGGAAA AAGCGGTCGT 8400
CATACTCTAG CCTGGTTGTC TCTCTTTATC TTTCTTGTGG GTATCATACT TTTAATTCTC 8460
TATCTTATAG CCGCCTATCG GAGTGAGAGA TGCCAACAGT GTTGCTCAAT CGGCAAAATT 8520
TTCTACCGCA CCCTGTAAGC TTCCTGTTGT TGTTTTTACA TCACGGTACG ATGAAGTCAC 8580
ACAGATAATT ACAGATGAGC TGTTCATATT TTTTATTATT TTTTCCAATT CCTGCACTAA 8640
AAAAAGAAGC ACTTTACGGA ACCGTGTCTG AGTATCTGTG GGGAATTTAG GTACTTTTTG 8700
CCGACGTCAG GAAAAATAAG TGTCGCCTAC ATAAGAGCCC GGTGCTATCG TGCTGTCACT 8760
CTTTCTTGTT GCCTTCGATG TACGGCGTCC TGGCTCATTA CTACTCCTTC ATCAGTAGCC 8820
CCAGCGTTAT GGTTAATTTT AAGCATCATA ACGCCGTGCA GCTGTTATGT GCACGGACCC 8880
GAGACGCACT GCCGGATGGG AACGTTTAAC CCATCATGCG TCGTATCACG CGAACTACGG 8940
GGCATACGCC GTGTTGATGG CTACATCGCA AAGAAAGTCC CTAGTGTTAC ATCGATACAG 9000
TGCCGTGACA GCCGTGGCCC TGCAGCTCAT GCCTGTTGAG ATCGTCCGCA AGCTAGATCA 9060
GTCGGACTGG GTGCGGGGTG CCTGGATCGT GTCAGAGACT TTTCCAACTA GCGACCCCAA 9120
AGGAGTTTGG AGCGACGATG ACTCCTCGAT GGGTGGAAGT GATGATTGAT GATGAGAACC 9180
TGACAAGAAA GACGAGAGAG AAATTTAGAG CTGTCATTGT AGAATTAGTC TAGATTCCTG 9240
ATAATAAACA GTATCGATTT TGAAACCTAA TTGACGTGTG ATCGATTTTT AAACCTCTGT 9300
GTTGTGTGAT TGATTGGTAT GTGGGGGGAT CCGATTTCAA AGGGGGGTAC TTATCGGGAA 9360
TTGATGTGTC ATGGACGCAG TTTTGAGCGA TTTTCCGGGA ATACCGGATA TTACGAATTA 9420
CTGGTAGTGA CGTAGATAAT AAAATTATAA TGCGATTAAT TTTTGGTGCG TTGATTATTT 9480
TTTTAGCATA TGTGTATCAT TATGAGGTGA ATGGAACAGA ATTACGCTGC AGATGTCTTC 9540
ATAGAAAATG GCCGCCTAAT AAAATTATAT TGGGTAATTA TTGGCTTCAT CGCGATCCCA 9600
GAGGGCCCGG ATGCGATAAA AATGAACATT TATTGTATCC AGACGGAAGG AAACCGCCTG 9660
GACCTGGAGT ATGTTTATCG CCCGATCACC TCTTCTCAAA ATGGTTAGAC AAACACAACG 9720
ATAATAGGTG GTATAATGTT AACATAACGA AATCACCAGG ACCGAGACGA ATAAATATAA 9780
CCTTGATAGG TGTTAGAGGA TAATATTTAA TGTATGTTTT CAAACAGACA AGTTCGTTAA 9840
AACAAAATAT TACAGTATGT GTTTAATATG GTGCTAACAT GGTTGCACCA TCCGGTTTCA 9900
AACTCGCATA TCAATCTGTT ATCGGTACGA CACCTGTCAT TAATCGCATA TATGTTACTT 9960
ACCATATGTC CCCTAGCCGT CCATGTTTTA GAACTAGAAG ATTACGACAG GCGCTGCCGT 10020
TGCAACAACC AAATTCTGTT GAATACCCTG CCGGTCGGAA CCGAATTGCT TAAGCCAATC 10080
```

-continued

```
GCAGCGAGCG AAAGCTGCAA TCGTCAGGAA GTGCTGGCTA TTTTAAAGGA CAAGGGAACC 10140
AAGTGTCTCA ATCCTAACGC GCAAGCCGTG CGTCGTCACA TCAACCGGCT ATTTTTTCGG 10200
TTAATCTTAG ACGAGGAACA ACGCATTTAC GACGTAGTGT CTACCAATAT TGAGTTCGGT 10260
GCCTGGCCAG TCCCTACGGC CTACAAAGCC TTTCTTTGGA AATACGCCAA GAGACTGAAC 10320
TACCACCACT TCAGACTGCG CTGGTGATCA TGTCCCTATT TTACCGTGCG GTAGCTCTGG 10380
GCACGCTAAG CGCTTTGGTG TGGTACAGCA CTAGCATCCT CGCAGAGATT AACGAAAATT 10440
CCTGCTCCTC ATCTTCTGCG GATCACGAAG ACTGCGAGGA ACCGGACGAG ATCGTTCGCG 10500
AAGAGCAAGA CTATCGGGCT CTGCTGGCCT TTTCCCTAGT GATTTGCGGT ACGCTCCTCG 10560
TCACTTGTGT GATCTGAGAC GTCATGCTGG TAGCGTTTAT GAGTCGGGCG GTGGCCGACA 10620
CGCCGCATTT CCTAACCCGC GCAGCATGTT GCGCTTGCTG TTCACGCTCG TCCTGCTGGC 10680
CCTCCACGGG CAGTCTGTCG GCGCTAGCCG CGACTATGTG CATGTTCGGC TACTGAGCTA 10740
CCGAGGCGAC CCCCTGGTCT TCAAGCACAC TTTCTCGGGT GTGCGTCGAC CCTTCACCGA 10800
GCTAGGCTGG GCTGCGTGTC GCGACTGGGA CAGTATGCAT TGCACACCCT TCTGGTCTAC 10860
CGATCTGGAG CAGATGACCG ACTCGGTGCG GCGTTACAGC ACGGTGAGCC CCGGCAAGGA 10920
AGTGACGCTT CAGCTTCACG GGAACCAAAC CGTACAGCCG TCGTTTCTAA GCTTTACGTG 10980
CCGCCTGCAG CTAGAACCCG TGGTGGAAAA TGTTGGCCTC TACGTGGCCT ACGTGGTCAA 11040
CGACGGCGAA CGCCCACAAC AGTTTTTTAC ACCGCAGGTA GACGTGGTAC GCTTTGCTCT 11100
ATATCTAGAA ACACTCTCCC GGATCGTGGA ACCGTTAGAA TCAGGTCGCC TGGCAGTGGA 11160
ATTTGATACG CCTGACCTAG CTCTGGCGCC CGATTTAGTA AGCAGCCTCT TCGTGGCCGG 11220
ACACGGCGAG ACCGACTTTT ACATGAACTG GACGCTGCGT CGCAGTCAGA CCCACTACCT 11280
GGAGGAGATG GCCTTACAGG TGGAGATTCT AAAACCCCGC GGCGTACGTC ACCGCGCTAT 11340
TATCCACCAT CCGAAGCTAC AGCCGGGCGT TGGCCTGTGG ATAGATTTCT GCGTGTACCG 11400
CTACAACGCG CGCCTGACCC GCGGCTACGT ACGATACACC CTGTCACCGA AAGCGCGCTT 11460
GCCCGCAAAA GCAGAGGGTT GGCTGGTGTC ACTAGACAGA TTCATCGTGC AGTACCTCAA 11520
CACATTGCTG ATTACAATGA TGGCGGCGAT ATGGGCTCGC GTTTTGATAA CCTACCTGGT 11580
GTCGCGGCGT CGGTAGAGGC TTGCGGAAAC CACGTCCTCG TCACACGTCG TTCGCGGACA 11640
TAGCAAGAAA TCCACGTCGC CACATCTCGA GAATGCCGGC CTTGCGGGGT CCCCTTCGCG 11700
CAACATTCCT GGCCCTGGTC GCGTTCGGGT TGCTGCTTCA GATAGACCTC AGCGACGCTA 11760
CGAATGTGAC CAGCAGCACA AAAGTCCCTA CTAGCACCAG CAACAGAAAT AACGTCGACA 11820
ACGCCACGAG TAGCGGACCC ACAACCGGGA TCAACATGAC CACCACCCAC GAGTCTTCCG 11880
TTCACAACGT GCGCAATAAC GAGATCATGA AAGTGCTGGC TATCCTCTTC TACATCGTGA 11940
CAGGCACCTC CATTTTCAGC TTCATAGCGG TACTGATCGC GGTAGTTTAC TCCTCGTGTT 12000
GCAAGCACCC GGGCCGCTTT CGTTTCGCCG ACGAAGAGGC CGTCAACCTG TTGGACGACA 12060
CGGACGACAG TGGCGGCAGC AGCCCGTTTG GCAGCGGTTC CCGACGAGGT TCTCAGATCC 12120
CCGCCGGATT TTGTTCCTCG AGCCCTTATC AGCGGTTGGA AACTCGGGAC TGGGACGAGG 12180
AGGAGGAGGC GTCCGCGGCC CGCGAGCGCA TGAAACATGA TCCTGAGAAC GTCATCTATT 12240
TCAGAAAGGA TGGCAACTTG GACACGTCGT TCGTGAATCC CAATTATGGG AGAGGCTCGC 12300
CTTTGACCAT CGAATCTCAC CTCTCGGACA ATGAGGAGGA CCCCATCAGG TACTACGTTT 12360
CGGTGTACGA TGAACTGACC GCCTCGGAAA TGGAAGAACC TTCGAACAGC ACCAGCTGGC 12420
AGATTCCCAA ACTAATGAAA GTTGCCATGC AACCCGTCTC GCTCAGAGAT CCCGAGTACG 12480
```

```
ACTAGGCTTT TTTTTTTGTC TTTCGGTTCC AACTCTTTCC CCGCCCCATC ACCTCGCCTG 12540
TACTATGTGT ATGATGTCTC ATAATAAAGC TTTCTTTCTC AGTCTGCAAC ATGCAGCTGT 12600
GTCGGGTGTG GCTGTCTGTT TGTCTGTGCG CCGTGGTGCT GGGTCAGTGC CAGCGGGAAA 12660
CCGCGGAAAA AAACGATTAT TACCGAGTAC CGCATTACTG GGACGCGTGC TCTCGCGCGC 12720
TGCCCGACCA AACCCGTTAC AAGTATGTGG AACAGCTCGT GGACCTCACG TTGAACTACC 12780
ACTACGATGC GAGCCACGGC TTGGACAACT TTGACGTGCT CAAGAGGTGA GGGTACGCGC 12840
TAAAGGTGCA TGACAACGGG AAGGTAAGGG CGAACGGGTA ACGGCTAAGT AACCGCATGG 12900
GGTATGAAAT GACGTTTGGA ACCTGTGCTT GCAGAATCAA CGTGACCGAG GTGTCGTTGC 12960
TCATCAGCGA CTTTAGACGT CAGAACCGTC GCGGCGGCAC CAACAAAAGG ACCACGTTCA 13020
ACGCCGCCGG TTCGCTGGCG CCACACGCCC GGAGCCTCGA GTTCAGCGTG CGGCTCTTTG 13080
CCAACTAGCC TGCGTCACGG GAAATAATAT GCTGCGGCTT CTGCTTCGTC ACCACTTTCA 13140
CTGCCTGCTT CTGTGCGCGG TTTGGGCAAC GCCCTGTCTG GCGTCTCCGT GGTCGACGCT 13200
AACGGCAAAC CAGAATCCGT CCCCGCCATG GTCTAAACTG ACGTATTCCA AACCGCATGA 13260
CGCGGCGACG TTTTACTGTC CTTTTCTCTA TCCCTCGCCC CCACGGTCCC CCTTGCAATT 13320
CTCGGGGTTC CAGCAGGTAT CAACGGGTCC CGAGTGTCGC AACGAGACCC TGTATCTGCT 13380
GTACAACCGG GAAGGCCAGA CCTTGGTGGA GAGAAGCTCC ACCTGGGTGA AAAAGGTGAT 13440
CTGGTATCTG AGCGGTCGCA ACCAGACCAT CCTCCAACGG ATGCCCCAAA CGGCTTCGAA 13500
ACCGAGCGAC GGAAACGTGC AGATCAGCGT GGAAGACGCC AAGATTTTTG GAGCGCACAT 13560
GGTGCCCAAG CAGACCAAGC TGCTACGCTT CGTCGTCAAC GATGGCACGC GTTATCAGAT 13620
GTGTGTGATG AAGCTGGAGA GCTGGGCCCA CGTCTTCCGG GACTACAGCG TGTCTTTTCA 13680
GGTGCGATTG ACGTTCACCG AGGCCAATAA CCAGACTTAC ACCTTCTGTA CCCATCCCAA 13740
TCTCATCATT TGAGCCCGTC GCGCGCGCAG GGAATTTTGA AAACCGCGCG TCATGAGTCC 13800
CAAAGACCTG ACGCCGTTCT TGACGACGTT GTGGCTGCTA TTGGGTCACA GCCGCGTGCC 13860
GCGGGTGCGC GCAGAAGAAT GTTGCGAATT CATAAACGTC AACCACCCGC CGGAACGCTG 13920
TTACGATTTC AAAATGTGCA ATCGCTTCAC CGTCGCGTAC GTATTTTCAT GATTGTCTGC 13980
GTTCTGTGGT GCGTCTGGAT TTGTCTCTCG ACGTTTCTGA TAGCCATGTT CCATCGACGA 14040
TCCTCGGGAA TGCCAGAGTA GATTTTCATG AATCCACAGG CTGCGGTGTC CGGACGGCGA 14100
AGTCTGCTAC AGTCCCGAGA AAACGGCTGA GATTCGCGGG ATCGTCACCA CCATGACCCA 14160
TTCATTGACA CGCCAGGTCG TACACAACAA ACTGACGAGC TGCAACTACA ATCCGTAAGT 14220
CTCTTCCTCG AGGGCCTTAC AGCCTATGGG AGAGTAAGAC AGAGAGGGAC AAAACATCAT 14280
TAAAAAAAAA AGTCTAATTT CACGTTTTGT ACCCCCCTTC CCCTCCGTGT TGTAGCCCAT 14340
CGGCCGCGGC GATCTCCTAG TAACACTCGT CCGACACTTC CACCATCTCC AGCTCGGCCG 14400
GCGGTTCGGC ATCCTCTACC AGCGGCGTCG TCTCATCTTT GCCGCAGCAG CGGACGCACA 14460
CCTTCTCCAG GCAGAACGCC ACCAGCTGCC GCCGAACGTA CCACAGGTAC ACGTGCAGAC 14520
CTGCGAACAG GACTACGGAG GTCATGACCA CCACGACGCA CACGGGAATC CAGGGATCGA 14580
GATTGTTGCT GGAACTCATG GCTATCGCCA CCGACGTGCC CGCGTCTGTC TCACCGCCGC 14640
TCGCCCGATG TCGCGCGGCT TGTTATACGC TAGCCCGTCG CCGCCTCGGG GCACGGTGCC 14700
CTCCTACCCA CGTAACTTCC TCCGTGACTT AAAGTCGCGT GTGGTAGATC TCCTGCTCCG 14760
TGGACGAACC GTCCGGCAGG ATAGCGGTTA AGGATTCGGT GCTAAGGCCG TGTCGCCAAC 14820
GTCGAATGCT ACGTTGCAAC AGCTTCGACG GACGGCCATC CCCTCTCTCA TCGCAATAAT 14880
```

-continued

```
AAAACACCAG CAGCGCGCAC GACGCGATCA CGGTGACACC CATGATTAGA CCCACGCAGA   14940
TAGCCAGCCC CGCTAGCGTA TCTAGCGCCA TCCCGTTCGC TCCCGTTGTC TCCTGAGCGA   15000
AGCAACTTCT CGGTCCCCGT TTTCAACAGT TTTTGTTTCC TTCTCCGCGA CTAGATGTTA   15060
ACGCCCGCGG TCTTTCCGGC CGTGCTCTAC CTCCTGGCGC TTGTCGTCTG GGTTGAGATG   15120
TTCTGCCTCG TCGCCGTAGC CGTCGTCGAG CGCGAGATCG CCTGGGCGCT GCTGCTGCGG   15180
ATGCTGGTCG TTGGCCTGAT GGTGGAAGTC GGCGCCGCCG CCGCTTGGAC CTTCGTGCGT   15240
TGTCTTGCCT ATCAGCGCTC CTTCCCCGTG CTTACGGCCT TCCCCTGAAA CCCACGTTAA   15300
CCGACCGTCC CAAAAACGCC GGTGTTAACA CAGGAAAAAA AGAAACCACG CAGGAACCGC   15360
GCAGGAACCA CGCGGAACAT GGGACACTAT CTGGAAATCC TGTTCAACGT CATCGTCTTC   15420
ACTCTGCTGC TCGGCGTCAT GGTCAGTATC GTCGCTTGGT ACTTCACGTG AACCACCGTC   15480
GTCCCGGTTT AAAAACCATC ATCGACGGCC GTTATAAAGC CACCCGGACA CGCGCCGCGG   15540
CACTTGCCTA CGGCGCTGCT TCAGGGAAAC TCCTCTTCCT TCTGCTCTTC CTCCTTCACC   15600
GCAGGGATCG TTTCCCTCGA CCAGGGACTC GCCGAAGCAA CCGCCGGAGC AACCTGGAGG   15660
AGTCGCGGCA TGACGGCGCC CAAGTGTGTC ACCACCAGTA CTTATCTGGT CAAGACCAAG   15720
GAACAGCCCT GGTGGCCCGA CAACGCCATC AGGAGATGGT GGATCAGTGT TGCTATCGTC   15780
ATCTTCATCG GAGTCTGTCT GGTGGCCCTG ATGTACTTTA CGCAGCAGCA GGCACGCAGC   15840
GGGAGCAGCA GCGGCTAGAC AAGTCTCTGG CGGCTACAGC TCCAAGCGCC GTAGCCGGGC   15900
CGCCTGCCGA TCGCGACGTC GTGGACCATC GAACAGAGAC TCACGCGTAC GAGACCCCGA   15960
GGTACGCCAC GCGGTGCCTA ACGCGGTATA CCACACCCGT ACGGTCTGCA GTGCGGCGTA   16020
CAACGTGTGG AAAACGCGTT GCGTCGCAGA GTCCGCCACG TTCCTGTCTT GTCGCTCCCC   16080
AATCGTCTCC CGCACACCCC CCGCGACACC CAGAGGGCGG GTGAGCCAAG TATTCTTAAG   16140
GCCGTTCTTT GTTCCATAGC CCATAAATTG TTGATTCCGG AGCTCGTTGG CGCGGAAATA   16200
GCCGGATAAG GGGAGCAACA ACCGTTGGCG AAAGCCGTCC CGCTCATTCA GTCCGGGTTT   16260
CGCGTCCAGT CGGACGTGTG ACCGTTGGGC AACGGAACGG CGTTTCACTG CCAAAATCGT   16320
ATCGGGTAGT GTACGAGACG TCGGCGGTGC AGAATGCGAC TCGCGGCGTA GCTCGCCGTC   16380
GCTATGCGGC TCGTCGCCGT GTGGCGCGGC CTGGCCGGCT GTCTGCGTCC AGATCTGTTG   16440
GCCTTTTGGT TCCTCTGGCT GCTGCTGCGT GTGTGCTTTG GTAGACGCGG TGGCAGTTTG   16500
CGGTCTGCGG TAAGTGAGGA TGTCGCCGAG CAAACGCACT TGCGGCGCGT GGGCGGCACG   16560
CGTGTCATTG TAGGTTCGTT GCCAGATGGC AAGTGCTGTC AACAGCAGGC GTTGTGGGCG   16620
GTCGGTGTAT TTTTGTGGGT TGCGGTGAGA GTCGGCACTC GGTGTTTTGT GAGTCATCTC   16680
AACTATCTGT GTTGCTTTGA GCAGCGTCCA GAACAGCGAC GCGACTTTGG GGATGGCCTC   16740
GTGCTCACCT CCGCGGAGAG CGCCGCCGGA CCTGCTCGTC AGCAGCGAGC TACGCAGACG   16800
GAATATCTGG AGGAGAGTTA CGTGTGTCAC AGGAGAGCGC GGGTCTCCGG CGGTAACGAC   16860
GGCGGTGTCG TCGACACGTG TGCGGCCTGT TGTGCTCTGC GGAAAAGTGC CGGTCTCGGA   16920
GACCGTGGAC GAAAAAGAGA ACGCAGCAGC TACCGCTGGC GGCGGCGGCG TTAATGCAGC   16980
CGTTGATGTT CGACGTTGTG AGCACTCGGA AACAGCGGTG AGGCAGAAGG TCGATTCTCC   17040
AGGGAACGAC AGTCGATGCG TGGTAGCCGC AGCAGGTGAG GTTGGGGCGG ACAACGTGTT   17100
GCGGATTGTG GCGAGAACGT CGTCCTCCCC TTCTTCACCG CCCCACCCAC CCTCGGTTGG   17160
TGTTTCTTTT TTCTTGTGTC CTGCAGATAG TTCCACGGAC AGCGACGGCA AGTCCATAAT   17220
CAGCGGTGTG CAAGTGGTGG AACACGACGA AGATATCATC GCGCCGCAGA GTTTGTGGTG   17280
```

-continued

```
CACGGCGTTC AAGGAAGCCC TCTGGGATGT GGCTCTGTTG GAAGTGCCGC GTTGGGCGTG   17340
GCAGGGCTGG AAGAGGTGGC GCAACAGCGA GGCCGGGCGT CGATGGAGTG CTGGGTCTGC   17400
GTCGGCTTCC AGCTTGTCTG ACTTGGCGGG CGAGGCCGTT GGAGAATTGG TGGGATCGGT   17460
CGTCGCGTAC GTGATCCTTG AACGTCTGTG GTTGGCAGCC AGAGGTTGGG TGTGCGAAAC   17520
AGGTGTGGAA GCCGAGGAGG CCATGTCGCG GCGGCGACAG CGCATGCTGT GGCGTATTGT   17580
TCTCTCGTGG AGGCGACGGC GAATGCAGCA GACGGTGTTC GATGGAGATG GCGTGCGGGG   17640
AAGAAAGCGC CGTGTTGTGA GCAGACGACG TAGGATGCGG GACGTCGGAG CACATGGGCC   17700
ATGTGTGGTG GCAGATGGCG GTGTCCGCTG GTGTCTGCTG CGGCAGTGCA TAGACGAAGC   17760
AACATGTCGC TGTGAAGAGA TAGAGTGTGA GCATAGCTGC ATGCAGCGTT GCGTGTATAA   17820
GCGGGGGGGA TTAAGACGTT AATAAAGAAT AGCGGCGGTT CTGATAGGGC GACCGCTGAA   17880
GTGAGCTGCG TGTGCGTGTG GTTTGTGGAG TCCCCGCCGC CCCCGGTCCC GTGTCCGCCG   17940
GCAAAGCCCC CCGGNTCCGC ACACTCCTGG CCGCGCAACC CTCGTCGCTG CAAAAGCCCC   18000
CCGTCCCCGC ACACCCCCGC GACCGCCGGT CCCGCGAGTC CCCGTCCCCG CCGCAAAAGG   18060
CCCCCGTCCT CGCCGCAAAC ACCCCCGTCA CCCCCGTCCC TCAGNCCGGG TCCGCGAGTC   18120
CCCGTTCCCA GCGTAATCCC CGTACCCGCA ACGNCCCGGN CCCACCGTCG TCCCGCACAC   18180
CCCCCGTCCC CCAGCCCGGT GCCCAGCGTG CGAAAAAAGC TCCGTCCCTC ACACCCGCAG   18240
AAAGATCCCT CAGCGCGGTG AAACCCCGTC CCCAGCGCCG TGCCGCTGAC AAAGACCATG   18300
GGACGACACG CACAGGCA                                                 18318
```

( 2 ) INFORMATION FOR SEQ ID NO:7:

( i ) SEQUENCE CHARACTERISTICS:
( A ) LENGTH: 257 amino acids
( B ) TYPE: amino acid
( D ) TOPOLOGY: linear ( i i ) MOLECULE TYPE: protein ( v i i ) IMMEDIATE SOURCE:
( B ) CLONE: tol.01

( i x ) FEATURE:
( A ) NAME/KEY: Protein
( B ) LOCATION: 1..257
( D ) OTHER INFORMATION: /label=UL133

( x i ) SEQUENCE DESCRIPTION: SEQ ID NO:7:

```
Met Gly Cys Asp Val His Asp Pro Ser Trp Gln Cys Gln Trp Gly Val
1               5                   10                  15

Pro Thr Ile Ile Val Ala Trp Ile Thr Cys Ala Ala Leu Gly Ile Trp
            20                  25                  30

Cys Leu Ala Gly Ser Ser Ala Asp Val Ser Ser Gly Pro Gly Ile Ala
        35                  40                  45

Ala Val Val Gly Cys Ser Val Phe Met Ile Phe Leu Cys Ala Tyr Leu
    50                  55                  60

Ile Arg Tyr Arg Glu Phe Phe Lys Asp Ser Val Ile Asp Leu Leu Thr
65                  70                  75                  80

Cys Arg Trp Val Arg Tyr Cys Ser Cys Ser Cys Lys Cys Ser Cys Lys
                85                  90                  95

Cys Ile Ser Gly Pro Cys Ser Arg Cys Cys Ser Ala Cys Tyr Lys Glu
            100                 105                 110

Thr Met Ile Tyr Asp Met Val Gln Tyr Gly His Arg Arg Arg Pro Gly
        115                 120                 125
```

-continued

His Gly Asp Asp Pro Asp Arg Val Ile Cys Glu Ile Val Glu Ser Pro
130 135 140

Pro Val Ser Ala Pro Thr Val Ser Val Pro Pro Pro Ser Glu Glu Ser
145 150 155 160

His Gln Pro Val Ile Pro Pro Gln Pro Pro Ala Pro Thr Ser Glu Pro
165 170 175

Lys Pro Lys Lys Gly Arg Ala Lys Asp Lys Pro Lys Gly Arg Pro Lys
180 185 190

Asp Lys Pro Pro Cys Glu Pro Thr Val Ser Ser Gln Pro Pro Ser Gln
195 200 205

Pro Thr Ala Met Pro Gly Gly Pro Pro Asp Ala Pro Pro Pro Ala Met
210 215 220

Pro Gln Met Pro Pro Gly Val Ala Glu Ala Val Gln Ala Ala Val Gln
225 230 235 240

Ala Ala Val Ala Ala Ala Leu Gln Gln Gln Gln Gln His Gln Thr Gly
245 250 255

Thr ( 2 ) INFORMATION FOR SEQ ID NO:8:

( i ) SEQUENCE CHARACTERISTICS:
( A ) LENGTH: 175 amino acids
( B ) TYPE: amino acid
( D ) TOPOLOGY: linear ( i i ) MOLECULE TYPE: protein ( v i i ) IMMEDIATE SOURCE:
( B ) CLONE: tol.02

( i x ) FEATURE:
( A ) NAME/KEY: Protein
( B ) LOCATION: 1..175
( D ) OTHER INFORMATION: /label=UL134

( x i ) SEQUENCE DESCRIPTION: SEQ ID NO:8:

Met Ala Arg Thr Arg Glu Ala Ser Pro Val Pro Pro Arg Ser Pro Met
1 5 10 15

Pro Ser His Ile His Thr Met Ile Phe Ser Pro Ala Trp Asn Leu Lys
20 25 30

Leu Arg Val Gly Lys Gly Arg Cys Thr Asp Ile Tyr Ala Leu Asp Phe
35 40 45

Trp Lys Arg His Phe Leu Ala Arg Asn Val Phe Ile Val Gln Thr Leu
50 55 60

Arg Lys Glu Met Cys Ala Lys Ser Glu Asn Ser Leu Ser His Arg Gly
65 70 75 80

Arg Val Thr Phe Arg Ser Asp Ala Ala Ala Val Val Val Glu Pro Arg
85 90 95

Pro Arg Pro Pro Ala Arg Gln Leu Val Pro Pro Arg Pro Arg Arg Val
100 105 110

Ala Ser Ala Ala Trp Arg Gly Glu Ala Arg Arg Ala Asp Arg Arg Ala
115 120 125

Leu Pro Ser Ala Ala Thr Val Val Val Asn Ser Pro Ser Val Arg Thr
130 135 140

Glu Val Cys Leu Ser Val Tyr Pro Ser Val Tyr Leu Ser Pro Tyr Leu
145 150 155 160

Ser Ser Val Trp Val Pro Met Ser Val Leu Ala Ala Ala Val Gly
165 170 175

( 2 ) INFORMATION FOR SEQ ID NO:9:

( i ) SEQUENCE CHARACTERISTICS:
( A ) LENGTH: 328 amino acids
( B ) TYPE: amino acid
( D ) TOPOLOGY: linear ( i i ) MOLECULE TYPE: protein ( v i i ) IMMEDIATE SOURCE:
( B ) CLONE: tol.03

( i x ) FEATURE:
( A ) NAME/KEY: Protein
( B ) LOCATION: 1..328
( D ) OTHER INFORMATION: /label=UL135

( x i ) SEQUENCE DESCRIPTION: SEQ ID NO:9:

```
Met Ser Val His Arg Pro Phe Pro Thr Arg Ser Leu Arg Phe Gln Ala
1               5                   10                  15

Gly Glu Lys Ile Met Val Trp Ile Trp Leu Gly Ile Gly Leu Leu Gly
            20                  25                  30

Gly Thr Gly Leu Ala Ser Leu Val Leu Ala Ile Ser Leu Phe Thr Gln
        35                  40                  45

Arg Arg Gly Arg Lys Arg Ser Asp Glu Thr Ser Ser Arg Gly Arg Leu
    50                  55                  60

Pro Gly Ala Ala Ser Asp Lys Arg Gly Ala Cys Ala Cys Cys Tyr Arg
65                  70                  75                  80

Asn Pro Lys Glu Asp Val Val Glu Pro Leu Asp Leu Glu Leu Gly Leu
                85                  90                  95

Met Arg Val Asp Thr His Pro Pro Thr Pro Gln Val Pro Arg Cys Thr
            100                 105                 110

Ser Leu Tyr Ile Gly Glu Asp Gly Leu Pro Ile Asp Lys Pro Glu Phe
        115                 120                 125

Pro Pro Ala Arg Phe Glu Ile Pro Asp Val Ser Thr Pro Gly Thr Pro
    130                 135                 140

Thr Ser Ile Gly Arg Ser Pro Ser His Cys Ser Ser Ser Ser Ser Leu
145                 150                 155                 160

Ser Ser Ser Thr Ser Val Asp Thr Val Leu Tyr Gln Pro Pro Pro Ser
                165                 170                 175

Trp Lys Pro Pro Pro Pro Pro Gly Arg Lys Lys Arg Pro Pro Thr Pro
            180                 185                 190

Pro Val Arg Ala Pro Thr Thr Arg Leu Ser Ser His Arg Pro Pro Thr
        195                 200                 205

Pro Ile Pro Ala Pro Arg Lys Asn Leu Ser Thr Pro Pro Thr Lys Lys
    210                 215                 220

Thr Pro Pro Pro Thr Lys Pro Lys Pro Val Gly Trp Thr Pro Pro Val
225                 230                 235                 240

Thr Pro Arg Pro Phe Pro Lys Thr Pro Thr Pro Gln Lys Pro Pro Arg
                245                 250                 255

Asn Pro Arg Leu Pro Arg Thr Val Gly Leu Glu Asn Leu Ser Lys Val
            260                 265                 270

Gly Leu Ser Cys Pro Cys Pro Arg Pro Arg Thr Pro Thr Glu Pro Thr
        275                 280                 285

Thr Leu Pro Ile Val Ser Val Ser Glu Leu Ala Pro Pro Pro Arg Trp
    290                 295                 300

Ser Asp Ile Glu Glu Leu Leu Glu Gln Ala Val Gln Ser Val Met Lys
305                 310                 315                 320

Asp Ala Glu Ser Met Gln Met Thr
```

325

( 2 ) INFORMATION FOR SEQ ID NO:10:

( i ) SEQUENCE CHARACTERISTICS:
( A ) LENGTH: 240 amino acids
( B ) TYPE: amino acid
( D ) TOPOLOGY: linear ( i i ) MOLECULE TYPE: protein ( v i i ) IMMEDIATE SOURCE:
( B ) CLONE: tol.04

( i x ) FEATURE:
( A ) NAME/KEY: Protein
( B ) LOCATION: 1..240
( D ) OTHER INFORMATION: /label=UL136

( x i ) SEQUENCE DESCRIPTION: SEQ ID NO:10:

```
Met Ser Val Lys Gly Val Glu Met Pro Glu Met Thr Trp Asp Leu Asp
1               5                   10                  15

Val Arg Asn Lys Trp Arg Arg Arg Lys Ala Leu Ser Arg Ile His Arg
            20                  25                  30

Phe Trp Glu Cys Arg Leu Arg Val Trp Trp Leu Ser Asp Ala Gly Val
        35                  40                  45

Arg Glu Thr Asp Pro Pro Arg Pro Arg Arg Arg Pro Thr Trp Met Thr
    50                  55                  60

Ala Val Phe His Val Ile Cys Ala Val Leu Leu Thr Leu Met Ile Met
65                  70                  75                  80

Ala Ile Gly Ala Leu Ile Ala Tyr Leu Arg Tyr Tyr His Gln Asp Ser
                85                  90                  95

Trp Arg Asp Met Leu His Asp Leu Phe Cys Gly Cys His Tyr Pro Glu
            100                 105                 110

Lys Cys Arg Arg His His Glu Arg Gln Arg Arg Arg Arg Gln Ala Met
        115                 120                 125

Asp Val Pro Asp Pro Glu Leu Gly Asp Pro Ala Arg Arg Pro Leu Asn
    130                 135                 140

Gly Ala Met Tyr Tyr Gly Ser Gly Cys Arg Phe Asp Thr Val Glu Met
145                 150                 155                 160

Val Asp Glu Thr Arg Pro Ala Pro Pro Ala Leu Ser Ser Pro Glu Thr
                165                 170                 175

Gly Asp Asp Ser Asn Asp Asp Ala Val Ala Gly Gly Gly Ala Gly Gly
            180                 185                 190

Val Thr Ser Pro Ala Thr Arg Thr Thr Ser Pro Asn Ala Leu Leu Pro
        195                 200                 205

Glu Trp Met Asp Ala Val His Val Ala Val Gln Ala Ala Val Gln Ala
    210                 215                 220

Thr Val Gln Val Ser Gly Pro Arg Glu Asn Ala Val Ser Pro Ala Thr
225                 230                 235                 240
```

( 2 ) INFORMATION FOR SEQ ID NO:11:

( i ) SEQUENCE CHARACTERISTICS:
( A ) LENGTH: 96 amino acids
( B ) TYPE: amino acid
( D ) TOPOLOGY: linear ( i i ) MOLECULE TYPE: protein ( v i i ) IMMEDIATE SOURCE:
( B ) CLONE: tol.05

( i x ) FEATURE:
( A ) NAME/KEY: Protein
( B ) LOCATION: 1..96
( D ) OTHER INFORMATION: /label=UL137

( x i ) SEQUENCE DESCRIPTION: SEQ ID NO:11:

Met Ala Thr Ile Ser Thr Ser Ile Thr Pro Met Met Gly Asn Pro Thr
1 5 10 15

Phe Ser Gly Arg Ser Ser Met Val Thr Val Leu Cys Pro Asp Leu Arg
20 25 30

Pro Ser Leu Ser Leu Leu Tyr Ser Thr Arg Ala Gly Thr Ala Pro Ser
35 40 45

Thr Leu Leu Arg Ser Gly Arg Tyr Gly Val Leu Pro Arg Ala Thr Tyr
50 55 60

Leu His Gly Arg Leu Asn Gly Gly Leu Asp Arg His Met His Arg Ile
65 70 75 80

His Pro Phe Trp Gln Gln Cys Val Arg Arg Arg Arg Thr Ser Arg Gly
85 90 95

( 2 ) INFORMATION FOR SEQ ID NO:12:

( i ) SEQUENCE CHARACTERISTICS:
( A ) LENGTH: 169 amino acids
( B ) TYPE: amino acid
( D ) TOPOLOGY: linear ( i i ) MOLECULE TYPE: protein ( v i i ) IMMEDIATE SOURCE:
( B ) CLONE: tol.06

( i x ) FEATURE:
( A ) NAME/KEY: Protein
( B ) LOCATION: 1..169
( D ) OTHER INFORMATION: /label=UL138

( x i ) SEQUENCE DESCRIPTION: SEQ ID NO:12:

Met Asp Asp Leu Pro Leu Asn Val Gly Leu Pro Ile Ile Gly Val Met
1 5 10 15

Leu Val Leu Ile Val Ala Ile Leu Cys Tyr Leu Ala Tyr His Trp His
20 25 30

Asp Thr Phe Lys Leu Val Arg Met Phe Leu Ser Tyr Arg Trp Leu Ile
35 40 45

Arg Cys Cys Glu Leu Tyr Gly Glu Tyr Glu Arg Arg Phe Ala Asp Leu
50 55 60

Ser Ser Leu Gly Leu Gly Ala Val Arg Arg Glu Ser Asp Arg Arg Tyr
65 70 75 80

Arg Phe Ser Glu Arg Pro Asp Glu Ile Leu Val Arg Trp Glu Glu Val
85 90 95

Ser Ser Gln Cys Ser Tyr Ala Ser Ser Arg Ile Thr Asp Arg Arg Val
100 105 110

Gly Ser Ser Ser Ser Ser Ser Val His Val Ala Ser Gln Arg Asn Ser
115 120 125

Val Pro Pro Pro Asp Met Ala Val Thr Ala Pro Leu Thr Asp Val Asp
130 135 140

Leu Leu Lys Pro Val Thr Gly Ser Ala Thr Gln Phe Thr Thr Val Ala
145 150 155 160

Met Val His Tyr His Gln Glu Tyr Thr
165

( 2 ) INFORMATION FOR SEQ ID NO:13:

( i ) SEQUENCE CHARACTERISTICS:
( A ) LENGTH: 135 amino acids
( B ) TYPE: amino acid
( D ) TOPOLOGY: linear ( i i ) MOLECULE TYPE: protein ( v i i ) IMMEDIATE SOURCE:
( B ) CLONE: tol.07

( i x ) FEATURE:
( A ) NAME/KEY: Protein
( B ) LOCATION: 1..135
( D ) OTHER INFORMATION: /label=UL139

( x i ) SEQUENCE DESCRIPTION: SEQ ID NO:13:

Met Leu Trp Ile Leu Val Leu Phe Ala Leu Ala Ala Ser Ala Ser Glu
1 5 10 15

Thr Thr Thr Gly Thr Ser Ser Asn Ser Ser Gln Ser Thr Ser Ala Thr
20 25 30

Ala Asn Thr Thr Val Ser Thr Cys Ile Asn Ala Ser Asn Gly Ser Ser
35 40 45

Trp Thr Val Pro Gln Leu Ala Leu Leu Ala Ala Ser Gly Trp Thr Leu
50 55 60

Ser Gly Leu Leu Leu Leu Phe Thr Cys Cys Phe Cys Cys Phe Trp Leu
65 70 75 80

Val Arg Lys Ile Cys Ser Cys Cys Gly Asn Ser Ser Glu Ser Glu Ser
85 90 95

Lys Thr Thr His Ala Tyr Thr Asn Ala Ala Phe Thr Ser Ser Asp Ala
100 105 110

Thr Leu Pro Met Gly Thr Thr Gly Ser Tyr Thr Pro Pro Gln Asp Gly
115 120 125

Ser Phe Pro Pro Pro Pro Arg
130 135

( 2 ) INFORMATION FOR SEQ ID NO:14:

( i ) SEQUENCE CHARACTERISTICS:
( A ) LENGTH: 114 amino acids
( B ) TYPE: amino acid
( D ) TOPOLOGY: linear ( i i ) MOLECULE TYPE: protein ( v i i ) IMMEDIATE SOURCE:
( B ) CLONE: tol.08

( i x ) FEATURE:
( A ) NAME/KEY: Protein
( B ) LOCATION: 1..114
( D ) OTHER INFORMATION: /label=UL140

( x i ) SEQUENCE DESCRIPTION: SEQ ID NO:14:

Met Thr Pro Ala Gln Thr Asn Ala Thr Thr Thr Val His Pro His Asp
1 5 10 15

Ala Lys Asn Gly Ser Gly Gly Ser Ala Leu Pro Thr Leu Val Val Phe
20 25 30

Gly Phe Ile Val Thr Leu Leu Phe Phe Leu Phe Met Leu Tyr Phe Trp
35 40 45

Asn Asn Asp Val Phe Arg Lys Leu Leu Arg Ala Leu Gly Ser Ser Ala
50 55 60

Val Ala Thr Ala Ser Thr Arg Gly Lys Thr Arg Ser Ser Thr Val Val
65 70 75 80

```
His His Val Val Pro Arg Ala Thr Thr Arg Val Val Leu Thr Ala Cys
                85                  90                  95

His Arg Thr Phe Phe Tyr His Pro Arg Pro Met Ala Val Leu Thr Thr
            100                 105                 110

Arg His
```

( 2 ) INFORMATION FOR SEQ ID NO:15:

( i ) SEQUENCE CHARACTERISTICS:
( A ) LENGTH: 425 amino acids
( B ) TYPE: amino acid
( D ) TOPOLOGY: linear ( i i ) MOLECULE TYPE: protein ( v i i ) IMMEDIATE SOURCE:
( B ) CLONE: tol.09

( i x ) FEATURE:
( A ) NAME/KEY: Protein
( B ) LOCATION: 1..425
( D ) OTHER INFORMATION: /label=UL141

( x i ) SEQUENCE DESCRIPTION: SEQ ID NO:15:

```
Met Arg Gln Val Ala Tyr Arg Arg Arg Arg Glu Ser Ser Cys Ala Val
1               5                   10                  15

Leu Val His His Val Gly Arg Asp Gly Asp Gly Glu Gly Glu Ala Ala
            20                  25                  30

Lys Lys Thr Cys Lys Lys Thr Gly Arg Ser Val Ala Gly Ile Pro Gly
        35                  40                  45

Glu Lys Leu Arg Arg Thr Val Val Thr Thr Thr Pro Ala Arg Arg Leu
    50                  55                  60

Ser Gly Arg His Thr Glu Gln Glu Gln Ala Gly Met Arg Leu Cys Glu
65                  70                  75                  80

Lys Gly Lys Lys Arg Ile Ile Met Cys Arg Arg Glu Ser Leu Arg Thr
                85                  90                  95

Leu Pro Trp Leu Phe Trp Val Leu Leu Ser Cys Pro Arg Leu Leu Glu
            100                 105                 110

Tyr Ser Ser Ser Ser Phe Pro Phe Ala Thr Ala Asp Ile Ala Glu Lys
        115                 120                 125

Met Trp Ala Glu Asn Tyr Glu Thr Thr Ser Pro Ala Pro Val Leu Val
    130                 135                 140

Ala Glu Gly Glu Gln Val Thr Ile Pro Cys Thr Val Met Thr His Ser
145                 150                 155                 160

Trp Pro Met Val Ser Ile Arg Ala Arg Phe Cys Arg Ser His Asp Gly
                165                 170                 175

Ser Asp Glu Leu Ile Leu Asp Ala Val Lys Gly His Arg Leu Met Asn
            180                 185                 190

Gly Leu Gln Tyr Arg Leu Pro Tyr Ala Thr Trp Asn Phe Ser Gln Leu
        195                 200                 205

His Leu Gly Gln Ile Phe Ser Leu Thr Phe Asn Val Ser Met Asp Thr
    210                 215                 220

Ala Gly Met Tyr Glu Cys Val Leu Arg Asn Tyr Ser His Gly Leu Ile
225                 230                 235                 240

Met Gln Arg Phe Val Ile Leu Thr Gln Leu Glu Thr Leu Ser Arg Pro
                245                 250                 255

Asp Glu Pro Cys Cys Thr Pro Ala Leu Gly Arg Tyr Ser Leu Gly Asp
            260                 265                 270

Gln Ile Trp Ser Pro Thr Pro Trp Arg Leu Arg Asn His Asp Cys Gly
```

-continued 275 280 285

Thr Tyr Arg Gly Phe Gln Arg Asn Tyr Phe Tyr Ile Gly Arg Ala Asp
290 295 300

Ala Glu Asp Cys Trp Lys Pro Ala Cys Pro Asp Glu Glu Pro Asp Arg
305 310 315 320

Cys Trp Thr Val Ile Gln Arg Tyr Arg Leu Pro Gly Asp Cys Tyr Arg
325 330 335

Ser Gln Pro His Pro Pro Lys Phe Leu Pro Val Thr Pro Ala Pro Pro
340 345 350

Ala Asp Ile Asp Thr Gly Met Ser Pro Trp Ala Thr Arg Gly Ile Ala
355 360 365

Ala Phe Leu Gly Phe Trp Ser Ile Phe Thr Val Cys Phe Leu Cys Tyr
370 375 380

Leu Cys Tyr Leu Gln Cys Cys Gly Arg Trp Cys Pro Thr Pro Gly Arg
385 390 395 400

Gly Arg Arg Gly Gly Glu Gly Tyr Arg Arg Leu Pro Thr Tyr Asp Ser
405 410 415

Tyr Pro Gly Val Arg Lys Met Lys Arg
420 425

( 2 ) INFORMATION FOR SEQ ID NO:16:

( i ) SEQUENCE CHARACTERISTICS:
( A ) LENGTH: 306 amino acids
( B ) TYPE: amino acid
( D ) TOPOLOGY: linear ( i i ) MOLECULE TYPE: protein ( v i i ) IMMEDIATE SOURCE:
( B ) CLONE: tol.10

( i x ) FEATURE:
( A ) NAME/KEY: Protein
( B ) LOCATION: 1..306
( D ) OTHER INFORMATION: /label=UL142

( x i ) SEQUENCE DESCRIPTION: SEQ ID NO:16:

Met Arg Ile Glu Trp Val Trp Trp Leu Phe Gly Tyr Phe Val Ser Ser
1 5 10 15

Val Gly Ser Glu Arg Ser Leu Ser Tyr Arg Tyr His Leu Glu Ser Asn
20 25 30

Ser Ser Thr Asn Val Val Cys Asn Gly Asn Ile Ser Val Phe Val Asn
35 40 45

Gly Thr Leu Gly Val Arg Tyr Asn Ile Thr Val Gly Ile Ser Ser Ser
50 55 60

Leu Leu Ile Gly His Leu Thr Ile Gln Val Leu Glu Ser Trp Phe Thr
65 70 75 80

Pro Trp Val Gln Asn Lys Ser Tyr Asn Lys Gln Pro Leu Gly Asp Thr
85 90 95

Glu Thr Leu Tyr Asn Ile Asp Ser Glu Asn Ile His Arg Val Ser Gln
100 105 110

Tyr Phe His Thr Arg Trp Ile Lys Ser Leu Gln Glu Asn His Thr Cys
115 120 125

Asp Leu Thr Asn Ser Thr Pro Thr Tyr Thr Tyr Gln Val Asn Val Asn
130 135 140

Asn Thr Asn Tyr Leu Thr Leu Thr Ser Ser Gly Trp Gln Asp Arg Leu
145 150 155 160

Asn Tyr Thr Val Ile Asn Ser Thr His Phe Asn Leu Thr Glu Ser Asn

-continued 165 170 175

Ile Thr Ser Ile Gln Lys Tyr Leu Asn Thr Thr Cys Ile Glu Arg Leu
180 185 190

Arg Asn Tyr Thr Leu Glu Ser Val Tyr Thr Thr Thr Val Pro Gln Asn
195 200 205

Ile Thr Thr Ser Gln His Ala Thr Thr Thr Met His Thr Ile Pro Pro
210 215 220

Asn Thr Ile Thr Ile Gln Asn Thr Thr Gln Ser His Thr Val Gln Thr
225 230 235 240

Pro Ser Phe Asn Asp Thr His Asn Val Thr Lys His Thr Leu Asn Ile
245 250 255

Ser Tyr Val Leu Ser Gln Lys Thr Asn Asn Thr Thr Ser Pro Trp Ile
260 265 270

Tyr Ala Ile Pro Met Gly Ala Thr Ala Thr Ile Gly Ala Gly Leu Tyr
275 280 285

Ile Gly Lys His Phe Thr Pro Val Lys Phe Val Tyr Glu Val Trp Arg
290 295 300

Gly Gln
305

( 2 ) INFORMATION FOR SEQ ID NO:17:

( i ) SEQUENCE CHARACTERISTICS:
( A ) LENGTH: 92 amino acids
( B ) TYPE: amino acid
( D ) TOPOLOGY: linear ( i i ) MOLECULE TYPE: protein ( v i i ) IMMEDIATE SOURCE:
( B ) CLONE: tol.11

( i x ) FEATURE:
( A ) NAME/KEY: Protein
( B ) LOCATION: 1..92
( D ) OTHER INFORMATION: /label=UL143

( x i ) SEQUENCE DESCRIPTION: SEQ ID NO:17:

Met Ala Arg Ser Val Lys Thr Ile Arg Ile Gln His Ile Tyr Ser Pro
1 5 10 15

Arg Ser Ser Asn Thr Leu Gln His Met Ser Lys Lys Gln Glu Ser Ile
20 25 30

Ala Thr Ile Thr Phe Gly Arg Ile Thr Cys Cys His Pro Leu Ala Ser
35 40 45

Ile Asn Leu Met Phe Asn Gly Ser Cys Thr Val Thr Val Lys Ile Ser
50 55 60

Met Gly Ile Asn Gly Ser Thr Asn Val His Gln Leu Val Ile Val Leu
65 70 75 80

His Leu Gly Asn Arg Cys Gln Pro Trp Arg Gln Val
85 90

( 2 ) INFORMATION FOR SEQ ID NO:18:

( i ) SEQUENCE CHARACTERISTICS:
( A ) LENGTH: 176 amino acids
( B ) TYPE: amino acid
( D ) TOPOLOGY: linear ( i i ) MOLECULE TYPE: protein ( v i i ) IMMEDIATE SOURCE:
( B ) CLONE: tol.12

( i x ) FEATURE:
( A ) NAME/KEY: Protein
( B ) LOCATION: 1..176
( D ) OTHER INFORMATION: /label=UL144

( x i ) SEQUENCE DESCRIPTION: SEQ ID NO:18:

```
Met Lys Pro Leu Ile Met Leu Ile Cys Phe Ala Val Ile Leu Leu Gln
1               5                   10                  15

Leu Gly Val Thr Lys Val Cys Gln His Asn Glu Val Gln Leu Gly Asn
            20                  25                  30

Glu Cys Cys Pro Pro Cys Gly Ser Gly Gln Arg Val Thr Lys Val Cys
        35                  40                  45

Thr Asp Tyr Thr Ser Val Thr Cys Thr Pro Cys Pro Asn Gly Thr Tyr
    50                  55                  60

Val Ser Gly Leu Tyr Asn Cys Thr Asp Cys Thr Gln Cys Asn Val Thr
65                  70                  75                  80

Gln Val Met Ile Arg Asn Cys Thr Ser Thr Asn Asn Thr Val Cys Ala
                85                  90                  95

Pro Lys Asn His Thr Tyr Phe Ser Thr Pro Gly Val Gln His His Lys
            100                 105                 110

Gln Arg Gln Gln Asn His Thr Ala His Ile Thr Val Lys Gln Gly Lys
        115                 120                 125

Ser Gly Arg His Thr Leu Ala Trp Leu Ser Leu Phe Ile Phe Leu Val
    130                 135                 140

Gly Ile Ile Leu Leu Ile Leu Tyr Leu Ile Ala Ala Tyr Arg Ser Glu
145                 150                 155                 160

Arg Cys Gln Gln Cys Cys Ser Ile Gly Lys Ile Phe Tyr Arg Thr Leu
                165                 170                 175
```

( 2 ) INFORMATION FOR SEQ ID NO:19:

( i ) SEQUENCE CHARACTERISTICS:
( A ) LENGTH: 100 amino acids
( B ) TYPE: amino acid
( D ) TOPOLOGY: linear ( i i ) MOLECULE TYPE: protein ( v i i ) IMMEDIATE SOURCE:
( B ) CLONE: tol.13

( i x ) FEATURE:
( A ) NAME/KEY: Protein
( B ) LOCATION: 1..100
( D ) OTHER INFORMATION: /label=UL145

( x i ) SEQUENCE DESCRIPTION: SEQ ID NO:19:

```
Met Cys Thr Asp Pro Arg Arg Thr Ala Gly Trp Glu Arg Leu Thr His
1               5                   10                  15

His Ala Ser Tyr His Ala Asn Tyr Gly Ala Tyr Ala Val Leu Met Ala
            20                  25                  30

Thr Ser Gln Arg Lys Ser Leu Val Leu His Arg Tyr Ser Ala Val Thr
        35                  40                  45

Ala Val Ala Leu Gln Leu Met Pro Val Glu Ile Val Arg Lys Leu Asp
    50                  55                  60

Gln Ser Asp Trp Val Arg Gly Ala Trp Ile Val Ser Glu Thr Phe Pro
65                  70                  75                  80

Thr Ser Asp Pro Lys Gly Val Trp Ser Asp Asp Asp Ser Ser Met Gly
                85                  90                  95

Gly Ser Asp Asp
            100
```

( 2 ) INFORMATION FOR SEQ ID NO:20:

( i ) SEQUENCE CHARACTERISTICS:
( A ) LENGTH: 117 amino acids
( B ) TYPE: amino acid
( D ) TOPOLOGY: linear ( i i ) MOLECULE TYPE: protein ( v i i ) IMMEDIATE SOURCE:
( B ) CLONE: tol.14

( i x ) FEATURE:
( A ) NAME/KEY: Protein
( B ) LOCATION: 1..117
( D ) OTHER INFORMATION: /label=UL146

( x i ) SEQUENCE DESCRIPTION: SEQ ID NO:20:

```
Met Arg Leu Ile Phe Gly Ala Leu Ile Ile Phe Leu Ala Tyr Val Tyr
1               5                   10                  15

His Tyr Glu Val Asn Gly Thr Glu Leu Arg Cys Arg Cys Leu His Arg
            20                  25                  30

Lys Trp Pro Pro Asn Lys Ile Ile Leu Gly Asn Tyr Trp Leu His Arg
        35                  40                  45

Asp Pro Arg Gly Pro Gly Cys Asp Lys Asn Glu His Leu Leu Tyr Pro
    50                  55                  60

Asp Gly Arg Lys Pro Pro Gly Pro Gly Val Cys Leu Ser Pro Asp His
65                  70                  75                  80

Leu Phe Ser Lys Trp Leu Asp Lys His Asn Asp Asn Arg Trp Tyr Asn
                85                  90                  95

Val Asn Ile Thr Lys Ser Pro Gly Pro Arg Arg Ile Asn Ile Thr Leu
            100                 105                 110

Ile Gly Val Arg Gly
        115
```

( 2 ) INFORMATION FOR SEQ ID NO:21:

( i ) SEQUENCE CHARACTERISTICS:
( A ) LENGTH: 159 amino acids
( B ) TYPE: amino acid
( D ) TOPOLOGY: linear ( i i ) MOLECULE TYPE: protein ( v i i ) IMMEDIATE SOURCE:
( B ) CLONE: tol.15

( i x ) FEATURE:
( A ) NAME/KEY: Protein
( B ) LOCATION: 1..159
( D ) OTHER INFORMATION: /label=UL147

( x i ) SEQUENCE DESCRIPTION: SEQ ID NO:21:

```
Met Val Leu Thr Trp Leu His His Pro Val Ser Asn Ser His Ile Asn
1               5                   10                  15

Leu Leu Ser Val Arg His Leu Ser Leu Ile Ala Tyr Met Leu Leu Thr
            20                  25                  30

Ile Cys Pro Leu Ala Val His Val Leu Glu Leu Glu Asp Tyr Asp Arg
        35                  40                  45

Arg Cys Arg Cys Asn Asn Gln Ile Leu Leu Asn Thr Leu Pro Val Gly
    50                  55                  60

Thr Glu Leu Leu Lys Pro Ile Ala Ala Ser Glu Ser Cys Asn Arg Gln
65                  70                  75                  80
```

Glu Val Leu Ala Ile Leu Lys Asp Lys Gly Thr Lys Cys Leu Asn Pro
85 90 95

Asn Ala Gln Ala Val Arg Arg His Ile Asn Arg Leu Phe Phe Arg Leu
100 105 110

Ile Leu Asp Glu Glu Gln Arg Ile Tyr Asp Val Val Ser Thr Asn Ile
115 120 125

Glu Phe Gly Ala Trp Pro Val Pro Thr Ala Tyr Lys Ala Phe Leu Trp
130 135 140

Lys Tyr Ala Lys Arg Leu Asn Tyr His His Phe Arg Leu Arg Trp
145 150 155

( 2 ) INFORMATION FOR SEQ ID NO:22:

( i ) SEQUENCE CHARACTERISTICS:
( A ) LENGTH: 316 amino acids
( B ) TYPE: amino acid
( D ) TOPOLOGY: linear ( i i ) MOLECULE TYPE: protein ( v i i ) IMMEDIATE SOURCE:
( B ) CLONE: tol.16

( i x ) FEATURE:
( A ) NAME/KEY: Protein
( B ) LOCATION: 1..316
( D ) OTHER INFORMATION: /label=UL148

( x i ) SEQUENCE DESCRIPTION: SEQ ID NO:22:

Met Leu Arg Leu Leu Phe Thr Leu Val Leu Leu Ala Leu His Gly Gln
1 5 10 15

Ser Val Gly Ala Ser Arg Asp Tyr Val His Val Arg Leu Leu Ser Tyr
20 25 30

Arg Gly Asp Pro Leu Val Phe Lys His Thr Phe Ser Gly Val Arg Arg
35 40 45

Pro Phe Thr Glu Leu Gly Trp Ala Ala Cys Arg Asp Trp Asp Ser Met
50 55 60

His Cys Thr Pro Phe Trp Ser Thr Asp Leu Glu Gln Met Thr Asp Ser
65 70 75 80

Val Arg Arg Tyr Ser Thr Val Ser Pro Gly Lys Glu Val Thr Leu Gln
85 90 95

Leu His Gly Asn Gln Thr Val Gln Pro Ser Phe Leu Ser Phe Thr Cys
100 105 110

Arg Leu Gln Leu Glu Pro Val Val Glu Asn Val Gly Leu Tyr Val Ala
115 120 125

Tyr Val Val Asn Asp Gly Glu Arg Pro Gln Gln Phe Phe Thr Pro Gln
130 135 140

Val Asp Val Val Arg Phe Ala Leu Tyr Leu Glu Thr Leu Ser Arg Ile
145 150 155 160

Val Glu Pro Leu Glu Ser Gly Arg Leu Ala Val Glu Phe Asp Thr Pro
165 170 175

Asp Leu Ala Leu Ala Pro Asp Leu Val Ser Ser Leu Phe Val Ala Gly
180 185 190

His Gly Glu Thr Asp Phe Tyr Met Asn Trp Thr Leu Arg Arg Ser Gln
195 200 205

Thr His Tyr Leu Glu Glu Met Ala Leu Gln Val Glu Ile Leu Lys Pro
210 215 220

Arg Gly Val Arg His Arg Ala Ile Ile His His Pro Lys Leu Gln Pro
225 230 235 240

Gly Val Gly Leu Trp Ile Asp Phe Cys Val Tyr Arg Tyr Asn Ala Arg
245 250 255

Leu Thr Arg Gly Tyr Val Arg Tyr Thr Leu Ser Pro Lys Ala Arg Leu
260 265 270

Pro Ala Lys Ala Glu Gly Trp Leu Val Ser Leu Asp Arg Phe Ile Val
275 280 285

Gln Tyr Leu Asn Thr Leu Leu Ile Thr Met Met Ala Ala Ile Trp Ala
290 295 300

Arg Val Leu Ile Thr Tyr Leu Val Ser Arg Arg Arg
305 310 315

( 2 ) INFORMATION FOR SEQ ID NO:23:

( i ) SEQUENCE CHARACTERISTICS:
( A ) LENGTH: 214 amino acids
( B ) TYPE: amino acid
( D ) TOPOLOGY: linear ( i i ) MOLECULE TYPE: protein ( v i i ) IMMEDIATE SOURCE:
( B ) CLONE: tol.19

( i x ) FEATURE:
( A ) NAME/KEY: Protein
( B ) LOCATION: 1..214
( D ) OTHER INFORMATION: /label=UL130

( x i ) SEQUENCE DESCRIPTION: SEQ ID NO:23:

Met Leu Arg Leu Leu Leu Arg His His Phe His Cys Leu Leu Leu Cys
1 5 10 15

Ala Val Trp Ala Thr Pro Cys Leu Ala Ser Pro Trp Ser Thr Leu Thr
20 25 30

Ala Asn Gln Asn Pro Ser Pro Pro Trp Ser Lys Leu Thr Tyr Ser Lys
35 40 45

Pro His Asp Ala Ala Thr Phe Tyr Cys Pro Phe Leu Tyr Pro Ser Pro
50 55 60

Pro Arg Ser Pro Leu Gln Phe Ser Gly Phe Gln Gln Val Ser Thr Gly
65 70 75 80

Pro Glu Cys Arg Asn Glu Thr Leu Tyr Leu Leu Tyr Asn Arg Glu Gly
85 90 95

Gln Thr Leu Val Glu Arg Ser Ser Thr Trp Val Lys Lys Val Ile Trp
100 105 110

Tyr Leu Ser Gly Arg Asn Gln Thr Ile Leu Gln Arg Met Pro Gln Thr
115 120 125

Ala Ser Lys Pro Ser Asp Gly Asn Val Gln Ile Ser Val Glu Asp Ala
130 135 140

Lys Ile Phe Gly Ala His Met Val Pro Lys Gln Thr Lys Leu Leu Arg
145 150 155 160

Phe Val Val Asn Asp Gly Thr Arg Tyr Gln Met Cys Val Met Lys Leu
165 170 175

Glu Ser Trp Ala His Val Phe Arg Asp Tyr Ser Val Ser Phe Gln Val
180 185 190

Arg Leu Thr Phe Thr Glu Ala Asn Asn Gln Thr Tyr Thr Phe Cys Thr
195 200 205

His Pro Asn Leu Ile Ile
210

( 2 ) INFORMATION FOR SEQ ID NO:24:

(i) SEQUENCE CHARACTERISTICS:
(A) LENGTH: 122 amino acids
(B) TYPE: amino acid
(D) TOPOLOGY: linear (ii) MOLECULE TYPE: protein (vii) IMMEDIATE SOURCE:
(B) CLONE: tol.20

(ix) FEATURE:
(A) NAME/KEY: Protein
(B) LOCATION: 1..122
(D) OTHER INFORMATION: /label=UL149

(xi) SEQUENCE DESCRIPTION: SEQ ID NO:24:

```
Met Val Asp Gln Cys Cys Tyr Arg His Leu His Arg Ser Leu Ser Gly
1               5                   10                  15

Gly Pro Asp Val Leu Tyr Ala Ala Ala Gly Thr Gln Arg Glu Gln Gln
            20                  25                  30

Arg Leu Asp Lys Ser Leu Ala Ala Thr Ala Pro Ser Ala Val Ala Gly
        35                  40                  45

Pro Pro Ala Asp Arg Asp Val Val Asp His Arg Thr Glu Thr His Ala
    50                  55                  60

Tyr Glu Thr Pro Arg Tyr Ala Thr Arg Cys Leu Thr Arg Tyr Thr Thr
65                  70                  75                  80

Pro Val Arg Ser Ala Val Arg Arg Thr Thr Cys Gly Lys Arg Val Ala
                85                  90                  95

Ser Gln Ser Pro Pro Arg Ser Cys Leu Val Ala Pro Gln Ser Ser Pro
            100                 105                 110

Ala His Pro Pro Arg His Pro Glu Gly Gly
        115                 120
```

(2) INFORMATION FOR SEQ ID NO:25:

(i) SEQUENCE CHARACTERISTICS:
(A) LENGTH: 642 amino acids
(B) TYPE: amino acid
(D) TOPOLOGY: linear (ii) MOLECULE TYPE: protein (vii) IMMEDIATE SOURCE:
(B) CLONE: tol.21

(ix) FEATURE:
(A) NAME/KEY: Protein
(B) LOCATION: 1..642
(D) OTHER INFORMATION: /label=UL150

(xi) SEQUENCE DESCRIPTION: SEQ ID NO:25:

```
Met Gln Leu Cys Ser His Ser Ile Ser Ser Gln Arg His Val Ala Ser
1               5                   10                  15

Ser Met His Cys Arg Ser Arg His Gln Arg Thr Pro Pro Ser Ala Thr
            20                  25                  30

Thr His Gly Pro Cys Ala Pro Thr Ser Arg Ile Leu Arg Arg Leu Leu
        35                  40                  45

Thr Thr Arg Arg Phe Leu Pro Arg Thr Pro Ser Pro Ser Asn Thr Val
    50                  55                  60

Cys Cys Ile Arg Arg Arg Leu His Glu Arg Thr Ile Arg His Ser Met
65                  70                  75                  80

Arg Cys Arg Arg Arg Asp Met Ala Ser Ser Ala Ser Thr Pro Val Ser
                85                  90                  95

His Thr Gln Pro Leu Ala Ala Asn His Arg Arg Ser Arg Ile Thr Tyr
```

-continued 100 105 110

Ala Thr Thr Asp Pro Thr Asn Ser Pro Thr Ala Ser Pro Ala Lys Ser
115 120 125

Asp Lys Leu Glu Ala Asp Ala Asp Pro Ala Leu His Arg Arg Pro Ala
130 135 140

Ser Leu Leu Arg His Leu Phe Gln Pro Cys His Ala Gln Arg Gly Thr
145 150 155 160

Ser Asn Arg Ala Thr Ser Gln Arg Ala Ser Leu Asn Ala Val His His
165 170 175

Lys Leu Cys Gly Ala Met Ile Ser Ser Ser Cys Ser Thr Thr Cys Thr
180 185 190

Pro Leu Ile Met Asp Leu Pro Ser Leu Ser Val Glu Leu Ser Ala Gly
195 200 205

His Lys Lys Lys Glu Thr Pro Thr Glu Gly Gly Trp Gly Gly Glu Glu
210 215 220

Gly Glu Asp Asp Val Leu Ala Thr Ile Arg Asn Thr Leu Ser Ala Pro
225 230 235 240

Thr Ser Pro Ala Ala Ala Thr Thr His Arg Leu Ser Phe Pro Gly Glu
245 250 255

Ser Thr Phe Cys Leu Thr Ala Val Ser Glu Cys Ser Gln Arg Arg Thr
260 265 270

Ser Thr Ala Ala Leu Thr Pro Pro Pro Pro Ala Val Ala Ala Ala Phe
275 280 285

Ser Phe Ser Ser Thr Val Ser Glu Thr Gly Thr Phe Pro Gln Ser Thr
290 295 300

Thr Gly Arg Thr Arg Val Asp Asp Thr Ala Val Val Thr Ala Gly Asp
305 310 315 320

Pro Arg Ser Pro Val Thr His Val Thr Leu Leu Gln Ile Phe Arg Leu
325 330 335

Arg Ser Ser Leu Leu Thr Ser Arg Ser Gly Gly Ala Leu Arg Gly Gly
340 345 350

Glu His Glu Ala Ile Pro Lys Val Ala Ser Leu Phe Trp Thr Leu Leu
355 360 365

Lys Ala Thr Gln Ile Val Glu Met Thr His Lys Thr Pro Ser Ala Asp
370 375 380

Ser His Arg Asn Pro Gln Lys Tyr Thr Asp Arg Pro Gln Arg Leu Leu
385 390 395 400

Leu Thr Ala Leu Ala Ile Trp Gln Arg Thr Tyr Asn Asp Thr Arg Ala
405 410 415

Ala His Ala Pro Gln Val Arg Leu Leu Gly Asp Ile Leu Thr Tyr Arg
420 425 430

Arg Pro Gln Thr Ala Thr Ala Ser Thr Lys Ala His Thr Gln Gln Gln
435 440 445

Pro Glu Glu Pro Lys Gly Gln Gln Ile Trp Thr Gln Thr Ala Gly Gln
450 455 460

Ala Ala Pro His Gly Asp Glu Pro His Ser Asp Gly Glu Leu Arg Arg
465 470 475 480

Glu Ser His Ser Ala Pro Pro Thr Ser Arg Thr Leu Pro Asp Thr Ile
485 490 495

Leu Ala Val Lys Arg Arg Ser Val Ala Gln Arg Ser His Val Arg Leu
500 505 510

Asp Ala Lys Pro Gly Leu Asn Glu Arg Asp Gly Phe Arg Gln Arg Leu
515 520 525

-continued

Leu Leu Pro Leu Ser Gly Tyr Phe Arg Ala Asn Glu Leu Arg Asn Gln
530 535 540

Gln Phe Met Gly Tyr Gly Thr Lys Asn Gly Leu Lys Asn Thr Trp Leu
545 550 555 560

Thr Arg Pro Leu Gly Val Ala Gly Gly Val Arg Glu Thr Ile Gly Glu
565 570 575

Arg Gln Asp Arg Asn Val Ala Asp Ser Ala Thr Gln Arg Val Phe His
580 585 590

Thr Leu Tyr Ala Ala Leu Gln Thr Val Arg Val Trp Tyr Thr Ala Leu
595 600 605

Gly Thr Ala Trp Arg Thr Ser Gly Ser Arg Thr Arg Glu Ser Leu Phe
610 615 620

Asp Gly Pro Arg Arg Arg Asp Arg Gln Ala Ala Arg Leu Arg Arg Leu
625 630 635 640

Glu Leu ( 2 ) INFORMATION FOR SEQ ID NO:26:

( i ) SEQUENCE CHARACTERISTICS:
( A ) LENGTH: 336 amino acids
( B ) TYPE: amino acid
( D ) TOPOLOGY: linear ( i i ) MOLECULE TYPE: protein ( v i i ) IMMEDIATE SOURCE:
( B ) CLONE: tol.22

( i x ) FEATURE:
( A ) NAME/KEY: Protein
( B ) LOCATION: 1..336
( D ) OTHER INFORMATION: /label=UL151

( x i ) SEQUENCE DESCRIPTION: SEQ ID NO:26:

Met Val Phe Val Ser Gly Thr Ala Leu Gly Thr Gly Phe His Arg Ala
1 5 10 15

Glu Gly Ser Phe Cys Gly Cys Glu Gly Arg Ser Phe Phe Arg Thr Leu
20 25 30

Gly Thr Gly Leu Gly Asp Gly Gly Cys Ala Gly Arg Arg Trp Xaa Arg
35 40 45

Xaa Val Ala Gly Thr Gly Ile Thr Leu Gly Thr Gly Thr Arg Gly Pro
50 55 60

Gly Leu Arg Asp Gly Gly Asp Gly Gly Val Cys Gly Glu Asp Gly Gly
65 70 75 80

Leu Leu Arg Arg Gly Arg Gly Leu Ala Gly Pro Ala Val Ala Gly Val
85 90 95

Cys Gly Asp Gly Gly Leu Leu Gln Arg Arg Gly Leu Arg Gly Gln Glu
100 105 110

Cys Ala Xaa Pro Gly Gly Phe Ala Gly Gly His Gly Thr Gly Gly Gly
115 120 125

Gly Asp Ser Thr Asn His Thr His Thr Gln Leu Thr Ser Ala Val Ala
130 135 140

Leu Ser Glu Pro Pro Leu Phe Phe Ile Asn Val Leu Ile Pro Pro Ala
145 150 155 160

Tyr Thr Arg Asn Ala Ala Cys Ser Tyr Ala His Thr Leu Ser Leu His
165 170 175

Ser Asp Met Leu Leu Arg Leu Cys Thr Ala Ala Ala Asp Thr Ser Gly
180 185 190

His Arg His Leu Pro Pro His Met Ala His Val Leu Arg Arg Pro Ala

-continued 195 200 205

Ser Tyr Val Val Cys Ser Gln His Gly Ala Phe Phe Pro Ala Arg His
210 215 220

Leu His Arg Thr Pro Ser Ala Ala Phe Ala Val Ala Ser Thr Arg Glu
225 230 235 240

Gln Tyr Ala Thr Ala Cys Ala Val Ala Ala Ala Thr Trp Pro Pro Arg
245 250 255

Leu Pro His Leu Phe Arg Thr Pro Asn Leu Trp Leu Pro Thr Thr Asp
260 265 270

Val Gln Gly Ser Arg Thr Arg Arg Pro Ile Pro Pro Ile Leu Gln Arg
275 280 285

Pro Arg Pro Pro Ser Gln Thr Ser Trp Lys Pro Thr Gln Thr Gln His
290 295 300

Ser Ile Asp Ala Arg Pro Arg Cys Cys Ala Thr Ser Ser Ser Pro Ala
305 310 315 320

Thr Pro Asn Ala Ala Leu Pro Thr Glu Pro His Pro Arg Gly Leu Pro
325 330 335

( 2 ) INFORMATION FOR SEQ ID NO:27:

( i ) SEQUENCE CHARACTERISTICS:
( A ) LENGTH: 270 amino acids
( B ) TYPE: amino acid
( D ) TOPOLOGY: linear ( i i ) MOLECULE TYPE: protein ( v i i ) IMMEDIATE SOURCE:
( B ) CLONE: tol.23

( i x ) FEATURE:
( A ) NAME/KEY: Protein
( B ) LOCATION: 1..270
( D ) OTHER INFORMATION: /label=UL132

( x i ) SEQUENCE DESCRIPTION: SEQ ID NO:27:

Met Pro Ala Leu Arg Gly Pro Leu Arg Ala Thr Phe Leu Ala Leu Val
1 5 10 15

Ala Phe Gly Leu Leu Leu Gln Ile Asp Leu Ser Asp Ala Thr Asn Val
20 25 30

Thr Ser Ser Thr Lys Val Pro Thr Ser Thr Ser Asn Arg Asn Asn Val
35 40 45

Asp Asn Ala Thr Ser Ser Gly Pro Thr Thr Gly Ile Asn Met Thr Thr
50 55 60

Thr His Glu Ser Ser Val His Asn Val Arg Asn Asn Glu Ile Met Lys
65 70 75 80

Val Leu Ala Ile Leu Phe Tyr Ile Val Thr Gly Thr Ser Ile Phe Ser
85 90 95

Phe Ile Ala Val Leu Ile Ala Val Val Tyr Ser Ser Cys Cys Lys His
100 105 110

Pro Gly Arg Phe Arg Phe Ala Asp Glu Glu Ala Val Asn Leu Leu Asp
115 120 125

Asp Thr Asp Asp Ser Gly Gly Ser Ser Pro Phe Gly Ser Gly Ser Arg
130 135 140

Arg Gly Ser Gln Ile Pro Ala Gly Phe Cys Ser Ser Ser Pro Tyr Gln
145 150 155 160

Arg Leu Glu Thr Arg Asp Trp Asp Glu Glu Glu Glu Ala Ser Ala Ala
165 170 175

Arg Glu Arg Met Lys His Asp Pro Glu Asn Val Ile Tyr Phe Arg Lys

-continued

| | | | | | | | | | | | | | | | |
|---|---|---|---|---|---|---|---|---|---|---|---|---|---|---|---|
| | | | 180 | | | | | 185 | | | | | 190 | | |
| Asp | Gly | Asn | Leu | Asp | Thr | Ser | Phe | Val | Asn | Pro | Asn | Tyr | Gly | Arg | Gly |
| | | 195 | | | | | 200 | | | | | 205 | | | |
| Ser | Pro | Leu | Thr | Ile | Glu | Ser | His | Leu | Ser | Asp | Asn | Glu | Glu | Asp | Pro |
| | 210 | | | | | 215 | | | | | 220 | | | | |
| Ile | Arg | Tyr | Tyr | Val | Ser | Val | Tyr | Asp | Glu | Leu | Thr | Ala | Ser | Glu | Met |
| 225 | | | | | 230 | | | | | 235 | | | | | 240 |
| Glu | Glu | Pro | Ser | Asn | Ser | Thr | Ser | Trp | Gln | Ile | Pro | Lys | Leu | Met | Lys |
| | | | | 245 | | | | | 250 | | | | | 255 | |
| Val | Ala | Met | Gln | Pro | Val | Ser | Leu | Arg | Asp | Pro | Glu | Tyr | Asp | | |
| | | | 260 | | | | | 265 | | | | | 270 | | |